(12) United States Patent
Bichon et al.

(10) Patent No.: US 6,710,042 B2
(45) Date of Patent: Mar. 23, 2004

(54) HUMAN NK₃ RECEPTOR-SELECTIVE ANTAGONIST COMPOUNDS, METHOD FOR OBTAINING THEM AND PHARMACEUTICAL COMPOSITIONS CONTAINING THEM

(75) Inventors: Daniel Bichon, Montpellier (FR); Xavier Edmonds-Alt, Combaillaux (FR); Patrick Gueule, Teyran (FR); Vincenzo Proietto, Saint Georges d'Orques (FR); Didier Van Broeck, Murviel les Montpellier (FR)

(73) Assignee: Sanofi-Synthelabo, Paris (FR)

( * ) Notice: Subject to any disclaimer, the term of this patent is extended or adjusted under 35 U.S.C. 154(b) by 117 days.

(21) Appl. No.: 09/954,862

(22) Filed: Sep. 18, 2001

(65) Prior Publication Data

US 2002/0049329 A1 Apr. 25, 2002

Related U.S. Application Data

(62) Division of application No. 09/437,203, filed on Nov. 9, 1999, now Pat. No. 6,291,672, which is a division of application No. 09/043,247, filed as application No. PCT/FR96/01416 on Sep. 13, 1996, now Pat. No. 6,028,082.

(30) Foreign Application Priority Data

Sep. 14, 1995 (FR) ............................................. 95 10776

(51) Int. Cl.⁷ .................. A61K 31/55; C07D 401/06
(52) U.S. Cl. .................. 514/212; 540/597; 540/598
(58) Field of Search .................. 514/212; 540/597, 540/598

(56) References Cited

U.S. PATENT DOCUMENTS

| | | | | |
|---|---|---|---|---|
| 5,340,822 A | * | 8/1994 | Emonds-Alt et al. | 514/316 |
| 5,563,133 A | * | 10/1996 | Hipskind | 514/212 |
| 6,291,672 B1 | * | 9/2001 | Bichon et al. | 540/597 |

* cited by examiner

*Primary Examiner*—C. S. Aulakh
(74) *Attorney, Agent, or Firm*—Paul E. Dupont; Michael D. Alexander

(57) ABSTRACT

Compounds of formula (I)

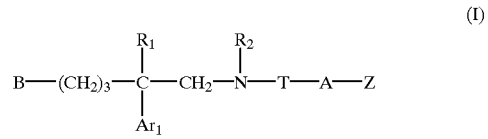

are useful as human NK₃ receptor antagonists.

12 Claims, No Drawings

HUMAN NK₃ RECEPTOR-SELECTIVE ANTAGONIST COMPOUNDS, METHOD FOR OBTAINING THEM AND PHARMACEUTICAL COMPOSITIONS CONTAINING THEM

CROSS REFERENCE TO RELATED APPLICATION

This application is a divisional of U.S. application Ser. No. 09/437,203 filed Nov. 9, 1999, now U.S. Pat. No. 6,291,672, which is a divisional of U.S. application Ser. No. 09/043,247 filed Mar. 12, 1998, now U.S. Pat. No. 6,028,082, which in turn is a 35 U.S.C. §371 application of PCT International Application No. PCT/FR$^{96/01416}$ filed Sep. 13, 1996, which claims priority of French Application No. 9510776 filed Sep. 14, 1995.

The present invention relates to novel selective human $NK_3$ receptor antagonist compounds for the preparation of drugs useful in the treatment of psychiatric diseases, diseases of psychosomatic origin, hypertension and, in general, any central or peripheral pathological condition in which neurokinin B and the $NK_3$ receptor are involved in the interneuronal regulatory processes, to a method of obtaining said compounds and to the pharmaceutical compositions in which they are present as the active principle.

Diseases of psychosomatic origin are understood as meaning diseases which originate in the central nervous system (CNS) and have pathological consequences on the peripheral nervous system.

In recent years, numerous research studies have been carried out on tachykinins and their receptors. Tachykinins are distributed throughout both the central nervous system and the peripheral nervous system. The tachykinin receptors have been recognized and are classified into three types: $NK_1$, $NK_2$, $NK_3$. Substance P (SP) is the endogenous ligand of the $NK_1$ receptors, neurokinin A ($NK_A$) that of the $NK_2$ receptors and neurokinin B ($NK_B$) that of the $NK_3$ receptors.

The $NK_1$, $NK_2$ and $NK_3$ receptors have been identified in different species. Thus the $NK_3$ receptors have been identified in the guinea-pig, the rat and the monkey (Br. J. Pharmacol., 1990, 99, 767–773); Neurochem. Int., 1991, 18 149–165); they have also been identified in man (FEBS Letters, 1992, 299 (1), 90–95).

A review by C. A. Maggi et al. looks at the tachykinin receptors and their antagonists and gives an account of the pharmacological studies and the applications in human therapeutics (J. Autonomic Pharmacol., 1993, 13, 23–93).

The following non-peptide compounds may be mentioned among the specific $NK_1$ receptor antagonists: CP-96345 (J. Med. Chem., 1992, 35, 2591–2600), RP-68651 (Proc. Natl. Acad. Sci. USA, 1991, 88, 10208–10212) and SR 140333 (Curr. J. Pharmacol., 1993, 250, 403–413).

In the case of the $NK_2$ receptor, the non-peptide selective antagonist SR 48968 has been described in detail (Life Sci., 1992, 50, PL101–PL106).

As far as the human $NK_3$ receptor is concerned, the non-peptide selective antagonist (+)-N-[1-[3-[1-benzoyl-3-(3,4-dichlorophenyl)piperid-3-yl]propyl]-4-phenylpiperid-4-yl]-N-methylacetamide hydrochloride, or SR 142801, has been described (EP-A-0 673 928; Peptides and their antagonists in tissue injury, Montreal, Canada, Jul. 31, 1994–Aug. 3, 1994. Canadian J. Physiol. Pharmacol., 1994, 72 (suppl. 2), 25, Abst. III. 0.9; Life Sci., 1994, 56 (1), 27–32; British Pharmacol. Society, Canterbury, Apr. 6–8, 1995; Eur. J. Pharmacol., 1995, 278 (1), 17–25; 1st Eur. Congress Pharmacol., Milan, Jun. 16–19, 1995).

Patent applications EP 474 561 and EP 512 901 describe neurokinin antagonists, more particularly $NK_1$ or $NK_2$ receptor antagonists. Pharmacological studies of peptide and non-peptide $NK_1$ and $NK_2$ receptor antagonists have shown that their affinities for these receptors, and their pharmacological activities, are very dependent on the species; this is very probably the result of small differences in the amino acid sequences, inducing very slight structural variations in these receptors from one species to another (J. Autonomic Pharmacol., 1993, 13 23–93). Some experimental data, confirmed by pharmacological characterization of the compounds forming the subject of the present invention, seem to indicate that a comparable situation exists for the $NK_3$ receptor. In particular, the human $NK_3$ receptor differs from the $NK_3$ receptor of the rat.

Non-peptide compounds have now been found which have a very strong affinity for the human $NK_3$ receptor and a high specificity for said receptor. These compounds can be used for the preparation of drugs useful in the treatment of psychiatric diseases, diseases of psychosomatic origin and any central or peripheral diseases in which neurokinin B and the $NK_3$ receptor are involved in the interneuronal regulatory processes.

Very strong affinity for the human $NK_3$ receptor is understood as meaning an affinity characterized by an inhibition constant Ki which is generally less than $5.10^{-9}$ M.

In ligand binding studies, the inhibition constant Ki is defined by the Cheng-Prusoff relationship (in Receptor Binding in Drug Research, eds. R. A. O'BRIEN. Marcel Dekker, New York, 1986):

$$Ki = \frac{IC_{50}}{1 + \frac{[L]}{Kd}}$$

[L]: concentration of the ligand,

Kd: dissociation constant of the ligand, $IC_{50}$: concentration which inhibits ligand binding by 50%.

High specificity for the human $NK_3$ receptor is understood as meaning that the inhibition constant (Ki) for the human $NK_3$ receptor is generally at least 100 times lower than the inhibition constant (Ki) for the $NK_2$ receptor or the inhibition constant for the $NK_1$ receptor of different species.

Thus, according to one of its aspects, the present invention relates to compounds of the formula (I)

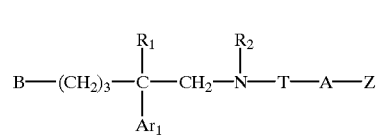

in which:

$R_1$ is hydrogen;

$R_2$ is the methyl group;

or $R_1$ and $R_2$ together form a group —$(CH_2)_3$— or —$(CH_2)_4$—;

$Ar_1$ is a phenyl which is unsubstituted or monosubstituted or polysubstituted by a substituent selected from a halogen atom, a hydroxyl, a $(C_1-C_4)$alkoxy, a $(C_1-C_4)$ alkyl, a trifluoromethyl and a methylenedioxy, said substituents being identical or different; a thienyl which is unsubstituted or substituted by a halogen atom; a benzothienyl which is unsubstituted or substituted by a halogen atom; a naphthyl which is unsubstituted or substituted by a halogen atom; an indolyl which is unsubstituted or N-substituted by a ($C_1$–$C_4$)alkyl or a benzyl; an imidazolyl which is unsubstituted or substituted by a halogen atom; a pyridyl which is unsubstituted or substituted by a halogen atom; or a biphenyl;

T is a group —$CH_2$—; a group —CO—; a group —COO—; or a group —$CONR_3$— in which $R_3$ is a hydrogen or a ($C_1$–$C_4$)alkyl;

A is a direct bond; a group —$(CH_2)_t$—, in which t is one, two or three; or a vinylene group;

or —T—A— is the group —$SO_2$—;

Z is an optionally substituted, mono-, di- or tri-cyclic aromatic or heteroaromatic group; and B is:
i—either a group $B_1$ of the formula

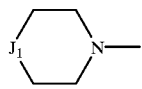

in which $J_1$ is:

$i_1$ either a group

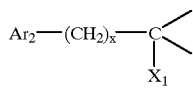

in which:

x is zero or one;

$Ar_2$ is a phenyl which is unsubstituted or monosubstituted or polysubstituted by a substituent selected from a halogen atom, a nitro, a hydroxyl, a trifluoromethyl, a ($C_1$–$C_4$)alkyl, a ($C_1$–$C_4$)alkoxy and a methylenedioxy, said substituents being identical or different; a pyridyl; a thienyl; a pyrimidyl; or an imidazolyl which is unsubstituted or substituted by a ($C_1$–$C_4$)alkyl; and $X_1$ is a group selected from:
(1) hydrogen;
(2) ($C_1$–$C_7$)alkyl;
(3) formyl;
(4) ($C_1$–$C_7$)alkylcarbonyl;
(5) —$(CH_2)_m$—$OR_4$;
(6) —$(CH_2)_m$—$OCOR_5$;
(7) —$(CH_2)_m$—OCONH—($C_1$–$C_7$)alkyl;
(8) —O—$CH_2CH_2$—$OR_6$;
(9) —$(CH_2)_n$—$SR_7$;
(10) —$CH_2$—$S(O)_j$—($C_1$–$C_7$)alkyl;
(11) —$NR_8R_9$;
(12) —$(CH_2)_p$—$NR_{10}R_{11}$;
(13) —$NR_{12}COR_{13}$;
(14) —$NR_4COCOR_{15}$;
(15) —$(CH_2)_p$—$NR_{14}C(=W_1)R_{16}$;
(16) —$(CH_2)_m$—$NR_{14}COOR_{17}$;
(17) —$(CH_2)_m$—$NR_{14}SO_2R_{18}$;
(18) —$(CH_2)_m$—$NR_{14}C(=W_1)NR_{19}R_{20}$;
(19) —$(CH_2)_n$—$COOR_{21}$;
(20) —$(CH_2)_n$—$C(=W_1)NR_{19}R_{20}$;
(21) —CO—$NR_{22}$—$NR_{23}R_{24}$;
(22) —CN;

(23)

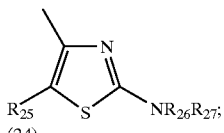

(24)

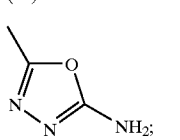

or $X_1$ forms a double bond between the carbon atom to which it is bonded and the adjacent carbon atom of the piperidine ring;

in which groups:

m is zero, one or two;
n is zero or one;
p is one or two;
j is one or two;
$W_1$ is an oxygen atom or a sulfur atom;
$R_4$ is a hydrogen or a ($C_1$–$C_7$)alkyl;
$R_5$ is a hydrogen; a ($C_1$–$C_7$)alkyl; a ($C_3$–$C_7$)cycloalkyl which is unsubstituted or substituted by one or more methyls; a phenyl; or a pyridyl;
$R_6$ is a hydrogen; a ($C_1$–$C_7$)alkyl; a formyl; or a ($C_1$–$C_7$) alkylcarbonyl;
$R_7$ is a hydrogen or a ($C_1$–$C_7$)alkyl;
$R_8$ and $R_9$ are each independently a hydrogen or a ($C_1$–$C_7$)alkyl; $R_9$ can also be a ($C_3$–$C_7$) cycloalkylmethyl, a benzyl or a phenyl;
or $R_8$ and $R_9$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a ($C_1$–$C_4$)alkyl;
$R_{10}$ and $R_{11}$ are each independently a hydrogen or a ($C_3$–$C_7$)alkyl; $R_{11}$ can also be a ($C_3$–$C_7$) cycloalkylmethyl or a benzyl;
$R_{12}$ is a hydrogen or a ($C_1$–$C_7$)alkyl;
$R_{13}$ is a hydrogen; a ($C_1$–$C_7$)alkyl; a ($C_3$–$C_7$)cycloalkyl which is unsubstituted or substituted by one or more methyls; a phenyl; a benzyl; a vinyl; a pyridyl; a furyl; a thienyl; a pyrrolyl; or an imidazolyl;
or $R_{12}$ and $R_{13}$ together are a group —$(CH_2)_u$—, in which u is three or four;
$R_{14}$ is a hydrogen or a ($C_1$–$C_7$)alkyl;
$R_{15}$ is a ($C_1$–$C_4$)alkoxy;
$R_{16}$ is a hydrogen; a ($C_1$–$C_7$)alkyl; a ($C_3$–$C_7$)cycloalkyl which is unsubstituted or substituted by one or more methyls; a phenyl; a benzyl; a vinyl; a pyridyl; a furyl; a thienyl; a pyrrolyl; or an imidazolyl;
$R_{17}$ is a ($C_1$–$C_7$)alkyl or a phenyl;
$R_{18}$ is a ($C_1$–$C_7$)alkyl; an amino which is free or substituted by one or two ($C_1$–$C_7$)alkyls; or a phenyl which is unsubstituted or monosubstituted or poly-substituted by a substituent selected from a halogen atom, a ($C_1$–$C_7$)alkyl, a trifluoromethyl, a hydroxyl, a ($C_1$–$C_7$) alkoxy, a carboxyl, a ($C_1$–$C_7$)alkoxycarbonyl, a ($C_1$–$C_7$)alkylcarbonyloxy, a cyano, a nitro and an amino which is free or substituted by one or two ($C_1$–$C_7$)alkyls, said substituents being identical or different;

$R_{19}$ and $R_{20}$ are each independently a hydrogen or a ($C_1$–$C_7$)alkyl; $R_{20}$ can also be a ($C_3$–$C_7$)cycloalkyl; a ($C_3$–$C_7$)cycloalkylmethyl; a hydroxyl; a ($C_1$–$C_4$)alkoxy; a benzyl; a phenyl; or a ($C_1$–$C_7$)alkyl substituted by a hydroxyl, a ($C_1$–$C_3$)alkoxy, a phenyl, a carboxyl, a ($C_1$–$C_3$)alkoxycarbonyl or a carbamoyl which is unsubstituted or substituted by one or two ($C_1$–$C_7$)alkyls;

or $R_{19}$ and $R_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a ($C_1$–$C_4$)alkyl;

$R_{21}$ is a hydrogen or a ($C_1$–$C_7$)alkyl;

$R_{22}$ is a hydrogen or a ($C_1$–$C_7$)alkyl;

$R_{23}$ and $R_{24}$ are each independently a hydrogen or a ($C_1$–$C_7$)alkyl;

$R_{25}$ is a hydrogen or a ($C_1$–$C_7$)alkyl; and $R_{26}$ and $R_{27}$ are each independently a hydrogen or a ($C_1$–$C_7$)alkyl; $R_{27}$ can also be a formyl or a ($C_1$–$C_7$)alkylcarbonyl;

$i_2$- or a group 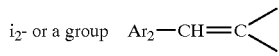

in which $Ar_2$ is as defined above;

$i_3$- or a group 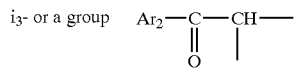

in which $Ar_2$ is as defined above;

$i_4$- or a group 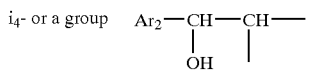

in which $Ar_2$ is as defined above;

$i_5$- or a group 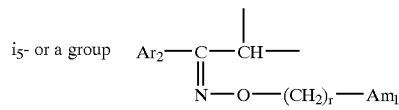

in which:
$Ar_2$ is as defined above;
$Am_1$ is an amino group substituted by two ($C_1$–$C_4$)alkyls; and
r is two or three;

$i_6$- or a group 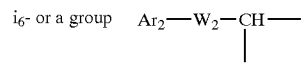

in which:
$Ar_2$ is as defined above;
$W_2$ is an oxygen atom; a sulfur atom; a sulfinyl; a sulfonyl; or a group —$NL_1$—;
$L_1$ is a hydrogen; a ($C_1$–$C_4$)alkyl; a ($C_1$–$C_4$)alkylcarbonyl; or a group —$(CH_2)_v$—$Am_2$;

v is one, two or three; and $Am_2$ is an amino group which is unsubstituted or monosubstituted or disubstituted by a ($C_1$–$C_4$)alkyl; $Am_2$ can also be a pyrrolidino, piperidino or morpholino group;

ii—or a group $B_2$ of the formula

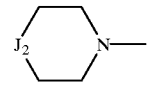

in which $J_2$ is:

$ii_1$- either a group 

$ii_2$- or a group 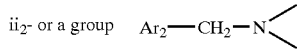

$ii_3$- or a group 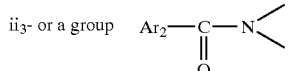

$ii_4$- or a group 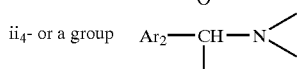

$ii_5$- or a group 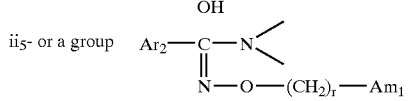

in which:
$Ar_2$ is as defined above;
r is two or three; and
$Am_1$ is as defined above;

iii—or a group $B_3$ of the formula

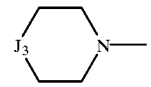

in which $J_3$ is:

a group: 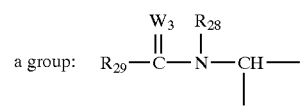

in which:
$W_3$ is an oxygen atom; a sulfur atom; or a group $NR_{30}$, in which $R_{30}$ is a hydrogen or a ($C_1$–$C_3$)alkyl;

$R_{28}$ is a hydrogen; a ($C_1$–$C_6$)alkyl; a ($C_3$–$C_6$)alkenyl in which one vinylic carbon atom is not bonded to the nitrogen atom; a 2-hydroxyethyl; a ($C_3$–$C_7$)cycloalkyl; a phenyl which is unsubstituted or monosubstituted or polysubstituted by a substituent selected from a halogen atom, a trifluoromethyl, a ($C_1$–$C_4$)alkyl, a ($C_1$–$C_4$)alkoxy, a nitro, an amino and a hydroxyl, said substituents being identical or different; or a 6-membered heteroaryl containing one or two nitrogen atoms as heteroatoms, said heteroaryl being unsubstituted or monosubstituted or polysubstituted by a substituent selected from a halogen atom, a trifluoromethyl, a ($C_1$–$C_4$)alkyl, a ($C_1$–$C_4$)alkoxy, a nitro, an amino and a hydroxyl, said substituents being identical or different;

$R_{29}$ is a hydrogen; a ($C_1$–$C_6$)alkyl which is unsubstituted or substituted by a hydroxyl and/or by one, two or three fluorine atoms; a ($C_3$–$C_6$)cycloalkyl; a ($C_1$–$C_5$)alkoxy (only when $W_3$ is an oxygen atom); a $(C_3-C_6)$ cycloalkoxy (only when $W_3$ is an oxygen atom); or a group —$NR_{31}R_{32}$ containing from zero to seven carbon atoms, $R_{29}$ being other than an unsubstituted $(C_1-C_4)$ alkyl when simultaneously $W_3$ is an oxygen and $R_{28}$ is a phenyl which is unsubstituted or monosubstituted or polysubstituted by a substituent selected from a halogen atom, a nitro, a hydroxyl, a trifluoromethyl, a $(C_1-C_4)$alkyl and a $(C_1-C_4)$alkoxy, said substituents being identical or different; a pyridyl; or a pyrimidyl;

or $R_{28}$ and $R_{29}$ together form a divalent hydrocarbon group $L_2$, in which the 1-position is bonded to the carbon atom carrying the substituent $W_3$, the divalent hydrocarbon group $L_2$ being selected from a trimethylene, a cis-propenylene, a tetramethylene, a cis-butenylene, a cis,cis-butadienylene, a pentamethylene and a cis-pentenylene, said divalent hydrocarbon group $L_2$ being unsubstituted or substituted by one or two methyls; and $R_{31}$ and $R_{32}$ are each independently a hydrogen, a $(C_1-C_5)$alkyl or a $(C_3-C_6)$cycloalkyl; or $R_{31}$ and $R_{32}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a $(C_1-C_4)$alkyl;

iv—or a group $B_4$ of the formula

in which:

$W_4$ is a $(C_1-C_8)$alkyl or a $(C_3-C_8)$cycloalkyl, said alkyl and cycloalkyl groups being unsubstituted or substituted by one or more substituents selected from a halogen atom; a $(C_3-C_6)$cycloalkyl; a cyano; a nitro; a hydroxyl; a $(C_1-C_4)$alkoxy; a formyloxy; a $(C_1-C_4)$ alkylcarbonytoxy; an arylcarbonyl; a heteroarylcarbonyl; an oxo; an imino which is unsubstituted or substituted on the nitrogen atom by a $(C_1-C_6)$alkyl, a $(C_3-C_6)$cycloalkyl, a formyl, a $(C_1-C_4)$alkylcarbonyl or an arylcarbonyl; a hydroxyimino which is unsubstituted or substituted on the oxygen atom by a $(C_1-C_4)$ alkyl or a phenyl; a group —$NR_{33}R_{34}$ containing from zero to seven carbon atoms; a group —$NR_{35}R_{36}$; a group —$C(=NR_{37})NR_{38}R_{39}$, in which the group —$NR_{38}R_{39}$ contains from zero to seven carbon atoms; and a group —$CON(OR_{40})R_{41}$, said substituents being identical or different;

$R_{33}$ and $R_{34}$ are each independently a hydrogen, a $(C_1-C_5)$alkyl or a $(C_3-C_6)$cycloalkyl; or $R_{33}$ and $R_{34}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a $(C_1-C_4)$alkyl;

$R_{35}$ is a hydrogen or a $(C_1-C_4)$alkyl;

$R_{36}$ is a formyl; a $(C_1-C_4)$alkylcarbonyl; an arylcarbonyl; a heteroarylcarbonyl; or a group —$C(=W_5)NR_{38}R_{39}$, in which the group —$NR_{38}R_{39}$ contains from zero to seven carbon atoms;

$W_5$ is an oxygen atom; a sulfur atom; a group $NR_{37}$; or a group $CHR_{42}$;

$R_{37}$ is a hydrogen or a $(C_1-C_4)$alkyl; or $R_{37}$ and $R_{39}$ together form an ethylene group or a trimethylene group;

$R_{38}$ and $R_{39}$ are each independently a hydrogen, a $(C_1-C_5)$alkyl or a $(C_3-C_6)$cycloalkyl; or $R_{38}$ and $R_{39}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a $(C_1-C_4)$alkyl; or $R_{38}$ is a hydrogen or a $(C_1-C_4)$alkyl and $R_{39}$ and $R_{37}$ together form an ethylene group or a trimethylene group;

$R_{40}$ and $R_{41}$ are each independently a $(C_1-C_3)$alkyl;

$R_{42}$ is a cyano; a nitro; or a group $SO_2R_{43}$, $R_{43}$ is a $(C_1-C_4)$alkyl or a phenyl; and when $W_4$ is a cyclic group or when a substituent of $W_4$ is a cyclic group or contains a cyclic group, said cyclic groups can also be substituted on a carbon atom by one or more $(C_1-C_3)$ alkyls; and when a substituent of $W_4$ contains an aryl group or a heteroaryl group, said aryl or heteroaryl groups can also be monosubstituted or polysubstituted by a substituent selected from a halogen atom, a $(C_1-C_4)$alkyl, a $(C_1-C_4)$alkoxy, a cyano, a trifluoromethyl and a nitro, said substituents being identical or different;

v—or a group $B_5$ of the formula

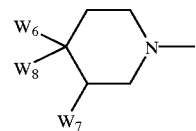

in which:

$W_6$ and $W_7$ are each a hydrogen; or $W_6$ is a hydrogen and $W_7$ is a hydroxyl;

$W_8$ is an aryl or a heteroaryl which are unsubstituted or substituted by an aryl, an arylcarbonyl, a heteroaryl or a heteroarylcarbonyl; said aryl or heteroaryl groups can also be monosubstituted or polysubstituted on the aromatic or heteroaromatic moiety and on a carbon atom by a substituent selected from a halogen atom; a cyano; a trifluoromethyl; a nitro; a hydroxyl; a $(C_1-C_5)$alkoxy; a formyloxy; a $(C_1-C_4)$alkylcarbonyloxy; a group —$NR_{33}R_{34}$ containing from zero to seven carbon atoms; a group —$NR_{35}R_{36}$; a group —$C(=NR_{37})$ $NR_{38}R_{39}$, in which the group —$NR_{38}R_{39}$ contains from zero to seven carbon atoms; a group —$COOR_{44}$; a group —$CONR_{45}R_{46}$, in which the group $NR_{45}R_{46}$ contains from zero to seven carbon atoms; a mercapto; a group —$S(O)_sR_{47}$; a $(C_1-C_5)$alkyl; a formyl; and a $(C_1-C_4)$alkylcarbonyl, said substituents being identical or different; when $W_6$ and $W_7$ are each a hydrogen, $W_8$ is other than a phenyl which is unsubstituted or monosubstituted or polysubstituted by a substituent selected from a halogen atom, a nitro, a hydroxyl, a trifluoromethyl and a $(C_1-C_4)$alkoxy, said substituents being identical or different; a pyridyl; a thienyl; a pyrimidyl; or an imidazolyl which is unsubstituted or substituted by a $(C_1-C_4)$alkyl;

or $W_7$ is a hydrogen and $W_6$ and $W_8$, together with a diradical $W_9$ and the piperidine carbon atom to which they are bonded, form a spiro ring in which $W_8$ is a phenyl substituted in the ortho position by a diradical $W_9$, which is itself joined to $W_6$, said phenyl being unsubstituted or substituted by a substituent selected from a halogen atom, a $(C_1-C_3)$alkyl, a $(C_1-C_3)$alkoxy, a hydroxyl, a $(C_1-C_3)$alkylthio, a $(C_1-C_3)$alkylsulfinyl and a $(C_1-C_3)$alkylsulfonyl; the diradical $W_9$ is a methylene, a carbonyl or a sulfonyl; and $W_6$ is an oxygen atom or a group —$NR_{48}$—, in which $R_{48}$ is a hydrogen or a $(C_1-C_3)$alkyl;

$R_{33}$, $R_{34}$, $R_{35}$, $R_{36}$, $R_{37}$, $R_{38}$ and $R_{39}$ are as defined above for the group $B_4$;

$R_{44}$ is a hydrogen; a $(C_1-C_5)$alkyl; an aryl; a heteroaryl; an arylmethyl; or a heteroarylmethyl;

$R_{45}$ and $R_{46}$ are each independently a hydrogen, a $(C_1-C_5)$alkyl or a $(C_3-C_6)$cycloalkyl; or $R_{45}$ and $R_{46}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a $(C_1-C_4)$alkyl;

s is zero, one or two;

$R_{47}$ is a $(C_1-C_6)$alkyl; a $(C_3-C_6)$cycloalkyl; an aryl; or a heteroaryl; and when $W_8$ or a substituent of $W_8$ contains a cyclic group, said cyclic group can also be substituted by one or more methyls; and when a heteroaryl group forming part of $W_8$ or of a substituent of $W_8$ contains a nitrogen atom as the heteroatom, said nitrogen atom can also be substituted by a $(C_1-C_5)$ alkyl; and when $W_8$ or a substituent of $W_8$ contains a $(C_1-C_5)$alkyl, $(C_1-C_5)$alkoxy, formyl or $(C_1-C_4)$-alkylcarbonyl group, said $(C_1-C_5)$alkyl, $(C_1-C_5)$ alkoxy, formyl or $(C_1-C_4)$alkylcarbonyl groups can also be substituted by a hydroxyl, a $(C_1-C_3)$alkoxy or one or more halogen atoms, with the proviso that a carbon atom bonded to a nitrogen atom or to an oxygen atom is not substituted by a hydroxyl or an alkoxy group, and with the proviso that a carbon atom in the α-position of a $(C_1-C_4)$alkylcarbonyl group is not substituted by a chlorine, bromine or iodine atom;

vi—or a group $B_6$ of the formula

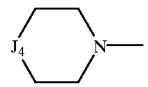

in which $J_4$ is:

vi$_1$- either a group 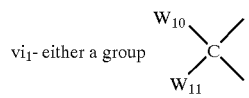

in which:

$W_{10}$ is a phenyl which is unsubstituted or monosubstituted to trisubstituted by a substituent selected from a halogen atom, a $(C_1-C_6)$alkoxy, a $(C_1-C_6)$alkyl and a trifluoromethyl, said substituents being identical or different; a benzyl which is unsubstituted or monosubstituted to trisubstituted by a substituent selected from a halogen atom, a $(C_1-C_6)$alkoxy, a $(C_1-C_6)$alkyl and a trifluoromethyl, said substituents being identical or different; a naphthyl which is unsubstituted or monosubstituted to trisubstituted by a substituent selected from a halogen atom, a $(C_1-C_6)$alkoxy, a $(C_1-C_6)$alkyl and a trifluoromethyl, said substituents being identical or different; a pyridyl which is unsubstituted or monosubstituted or disubstituted by a substituent selected from a halogen atom, a $(C_1-C_6)$alkyl and a $(C_1-C_6)$ alkoxy, said substituents being identical or different; a thienyl; a pyrimidyl; or an imidazolyl; and $W_{11}$ is a group —$CONHR_{49}$;

$R_{49}$ is a group $CH_3$—$CHOH$—$CH$—$COO$—$(C_1-C_6)$alkyl;

a group $(C_1-C_6)$alkyl—$OCO$—$CH_2$—$CH_2$—$CH$—$COO$—$(C_1-C_6)$alkyl;

a group —$CH_2CH_2N(CH_3)_2$;

vi$_2$- or a group:

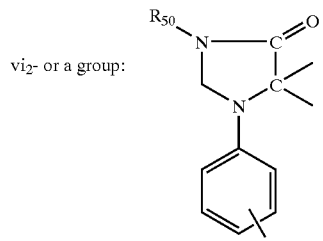

vi$_3$- or a group:

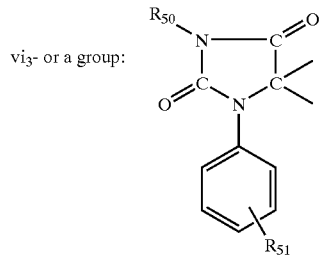

vi$_4$- or a group:

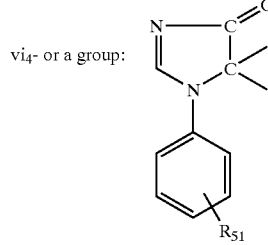

in which:

$R_{50}$ is a hydrogen, a $(C_1-C_6)$alkyl or a benzyl; and $R_{51}$ is from one to three substituents selected from a hydrogen, a halogen atom, a trifluoromethyl, a $(C_1-C_6)$ alkyl and a $(C_1-C_6)$alkoxy, said substituents being identical or different;

vii—or a group $B_7$ of the formula

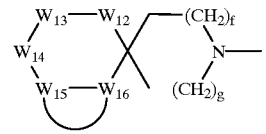

in which:

f and g are each independently zero, one, two, three, four or five, with the proviso that f+g is equal to one, two, three, four or five;

$W_{12}$ is a direct bond; a $(C_1-C_3)$alkylene which is unsubstituted or substituted by an oxo, a group $OR_{52}$, a halogen, a trifluoromethyl or a phenyl which is itself unsubstituted or mono-, di- or tri-substituted by a substituent selected from a hydroxyl, a cyano, a halogen and a trifluoromethyl; a group —$S(O)_k$—; a group $(C_1-C_3)$alkylene-$S(O)_k$—; a group —$S(O)_k$—$(C_1-C_2)$ alkylene; a group —$S(O)_k$—$NH$—; a group —$S(O)_j$— $NR_{52}$—; a group —$S(O)_j$—$NR_{52}$—$(C_1-C_2)$alkylene; a group —$CONR_{52}$—; a group —$CONR_{52}$—$(C_1-C_2)$ alkylene; a group —COO—; or a group —COO—$(C_1-C_2)$alkylene;

$W_{13}$ is a group —$NR_{53}$—; an oxygen atom; a sulfur atom; a sulfinyl; or a sulfonyl, with the proviso that when $W_{12}$ is a direct bond and when $W_{14}$ is a $(C_1-C_3)$alkylene, $W_{13}$ is a group —$NR_{53}$—;

$W_{14}$ is a direct bond; a $(C_1-C_3)$alkylene which is unsubstituted or substituted by an oxo, a group $OR_{52}$, a halogen, a trifluoromethyl or a phenyl which is itself unsubstituted or mono-, di- or tri-substituted by a substituent selected from a group $OR_{52}$, a halogen and a trifluoromethyl; a group —$S(O)_k$—; a group $(C_1-C_3)$alkylene-$S(O)_k$—; a group —$S(O)_k$—$(C_1-C_2)$alkylene; a group —$NHS(O)_j$—; a group —NH—$(C_1-C_2)$alkylene-$S(O)_j$—; a group —$S(O)_jNR_{52}$—; a group —$S(O)_j$—$NR_{52}$—$(C_1-C_2)$alkylene; a group —NHCO—$(C_1-C_2)$alkylene; a group —$NR_{52}$—CO—; a group —$NR_{52}$—$(C_1-C_2)$alkylene-CO—; a group —OCO—; or a group $(C_1-C_2)$alkylene-OCO—;

$W_{15}$–$W_{16}$ together form two adjacent atoms of a cyclic radical of the formula

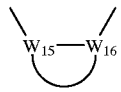

said cyclic radical being a phenyl, a naphthyl or a heteroaryl group selected from a benzimidazolyl, a benzofuranyl, a benzoxazolyl, a furanyl, an imidazolyl, an indolyl, an isoxazolyl, an isothiazolyl, an oxadiazolyl, an oxazolyl, a pyrazinyl, a pyrazolyl, a pyridyl, a pyrimidyl, a pyrrolyl, a quinolyl, a tetrazolyl, a thiadiazolyl, a thiazolyl, a thienyl and a triazolyl, and said phenyl, naphthyl or heteroaryl cyclic radical being unsubstituted or mono-, di- or tri-substituted by $R_{54}$;

k is zero, one or two;

j is one or two;

$R_{52}$ is a hydrogen; a $(C_1-C_6)$alkyl which is unsubstituted or monosubstituted or disubstituted by a substituent selected independently from a hydroxyl, an oxo, a cyano, a halogen atom, a trifluoromethyl and a phenyl which is itself unsubstituted or substituted by a hydroxyl, a $(C_1-C_3)$alkyl, a cyano, a halogen, a trifluoromethyl or a $(C_1-C_4)$alkoxy; a phenyl, a pyridyl or a thiophene, said phenyl, pyridyl or thiophene being unsubstituted or mono-, di- or tri-substituted by a substituent selected independently from a hydroxyl, a $(C_1-C_4)$alkyl, a cyano, a halogen atom and a trifluoromethyl; or a $(C_1-C_3)$alkoxy;

$R_{53}$ is a hydrogen; a $(C_1-C_8)$alkyl which is unsubstituted or monosubstituted or polysubstituted by a substituent selected from a group —$OR_{52}$, an oxo, a group —$NHCOR_{52}$, a group —$NR_{55}R_{56}$, a cyano, a halogen atom, a trifluoromethyl and a phenyl which is itself unsubstituted or substituted by a hydroxyl, a cyano, a halogen atom or a trifluoromethyl; a group —$S(O)R_{57}$; a group —$CO_2R_{57}$; a group —$SO_2R_{57}$; a group —$COR_{57}$; or a group —$CONR_{56}R_{57}$;

$R_{54}$ is a hydrogen; a $(C_1-C_6)$alkyl which is unsubstituted or monosubstituted or disubstituted by a hydrogen or a hydroxyl; an oxo; a group —$OR_{52}$; a halogen atom; a trifluoromethyl; a nitro; a cyano; a group —$NR_{55}R_{56}$; a group —$NR_{55}COR_{56}$; a group —$NR_{55}CO_2R_{56}$; a group —$NHS(O)_jR_{52}$; a group —$NR55S(O)_jR_{56}$; a group —$CONR_{55}R_{56}$; a group —$COR_{52}$; a group —$CO_2R_{52}$; a group —$S(O)_jR_{52}$; or a heteroaryl group, said heteroaryl being selected from a benzimidazolyl, a benzofuranyl, a benzoxazolyl, a furanyl, an imidazolyl, an indolyl, an isoxazolyl, an isothiazolyl, an oxadiazolyl, an oxazolyl, a pyrazinyl, a pyrazolyl, a pyridyl, a pyrimidinyl, a pyrrolyl, a quinolyl, a tetrazolyl, a thiadiazolyl, a thiazolyl, a thienyl and a triazolyl, and said heteroaryl being unsubstituted or monosubstituted or disubstituted by $R_{58}$;

$R_{55}$ is $R_{52}$;

$R_{56}$ is $R_{52}$;

or $R_{55}$ and $R_{56}$, together with the atoms to which they are bonded, form a five-, six- or seven-membered, saturated monocyclic heterocycle containing one or two heteroatoms, said heteroatoms being selected independently from a nitrogen atom, an oxygen atom and a sulfur atom, said heterocycle being unsubstituted or monosubstituted or disubstituted by a substituent selected from a hydroxyl, an oxo, a cyano, a halogen atom and a trifluoromethyl;

$R_{57}$ is a $(C_1-C_6)$alkyl which is unsubstituted or mono-, di- or tri-substituted by a substituent selected from a hydroxyl, an oxo, a cyano, a group —$OR_{52}$, a group —$NR_{55}R_{56}$, a group —$NR_{55}COR_{56}$, a halogen atom, a trifluoromethyl and a phenyl which is itself unsubstituted or mono-, di- or tri-substituted by a substituent selected from a hydroxyl, an oxo, a cyano, a group —$NHR_{52}$, a group —$NR_{55}R_{56}$, a group —$NR_{55}COR_{56}$, a halogen atom, a trifluoromethyl and a $(C_1-C_3)$alkyl;

$R_{58}$ is a hydrogen; a $(C_1-C_6)$alkyl which is unsubstituted or monosubstituted or disubstituted by a hydrogen or a hydroxyl; an oxo; a group —$OR_{52}$; a trifluoromethyl; a nitro; a cyano; a group —$NR_{55}R_{56}$; a group —$NR_{55}COR_{56}$; a group —$NR_{55}CO_2R_{56}$; a group —$NHS(O)_jR_{52}$; a group —$NR_{55}S(O)_jR_{56}$; a group —$CONR_{55}R_{56}$; a group —$COR_{52}$; a group —$CO_2R_{52}$; a group —$S(O)_jR_{52}$; or a phenyl, and the group $B_7$ being other than the group $B_5$ when $W_7$ is a hydrogen and $W_6$ and $W_8$, together with a diradical $W_9$ and the piperidine carbon atom to which they are bonded, form a spiro ring;

viii—or a group $B_8$ of the formula

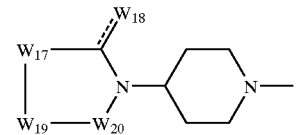

in which:

$W_{17}$ is a direct bond; a double bond; or a divalent hydrocarbon radical;

$W_{18}$ is a radical which is joined to the carbon atom of the heterocycle either by a single bond when $W_{17}$ is a double bond, or by a double bond in the other cases;

$W_{19}$ is an unsubstituted or optionally substituted heteroatom;

$W_{20}$ is a hydrocarbon radical of which the 1-position is joined to $W_{19}$; and the meanings of $W_{17}$, $W_{18}$, $W_{19}$ and $W_{20}$ are selected from:

(a) $W_{17}$ is a direct bond; $W_{18}$ is an oxo or thioxo group; $W_{19}$ is an oxy or thio group or a group $NR_{59}$; and $W_{20}$ is a hydrocarbon radical $L_3$; or (b) $W_{17}$ is a direct bond; $W_{18}$ is a group $NR_{60}$; $W_{19}$ is a group $NR_{61}$; and $W_{20}$ is a hydrocarbon radical $L_3$; or (c) $W_{17}$ is a double bond; $W_{18}$ is a group $OR_{61}$, $SR_{61}$ or $NR_{62}R_{63}$; $W_{19}$ is a nitrogen atom; and $W_{20}$ is a hydrocarbon radical $L_3$; or (d) $W_{17}$ is a methylene which is unsubstituted or substituted by one or two methyl groups; $W_{18}$ is an oxo or thioxo group or a group $NR_{64}$; $W_{19}$ is an oxy, thio, sulfinyl or sulfonyl group or a group $NR_{61}$; and $W_{20}$ is a hydrocarbon radical $L_4$; or (e) $W_{17}$ is a direct bond; $W_{18}$ is an oxo or thioxo group or a group $NR_{64}$; $W_{19}$ is a nitrogen atom; and $W_{20}$ is a hydrocarbon radical $L_5$; or (f) $W_{17}$ is a methine group which is unsubstituted or substituted by one or two methyl groups; $W_{19}$ is an oxo or thioxo group or a group $NR_{64}$; $W_{19}$ is a nitrogen atom; and $W_{20}$ is a hydrocarbon radical $L_6$; and (g) $W_{17}$ is a cis-vinylene group which is unsubstituted or substituted by one or two methyl groups; $W_{18}$ is an oxo or thioxo group or a group $NR_{64}$; $W_{19}$ is a nitrogen atom; and $W_{20}$ is a hydrocarbon radical $L_7$;

$R_{59}$ is a hydrogen; a $(C_1-C_3)$alkyl; a group —$CH_2COOR_{65}$; or a group —$CH_2CONR_{66}R_{67}$, $R_{60}$ is a hydrogen; a $(C_1-C_3)$alkyl; a cyano; a nitro; or a $(C_1-C_3)$alkylsulfonyl group;

$R_{61}$ is a hydrogen or a $(C_1-C_3)$alkyl;

$R_{62}$ and $R_{63}$ are each independently a hydrogen or a $(C_1-C_3)$alkyl;

or $R_{62}$ and $R_{63}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a $(C_1-C_4)$alkyl;

$R_{64}$ is a hydrogen or a $(C_1-C_3)$alkyl;

$R_{65}$ is a hydrogen or a $(C_1-C_3)$alkyl;

$R_{66}$ and $R_{67}$ are each independently a hydrogen; a $(C_1-C_3)$alkyl; a phenyl; or a benzyl;

$L_3$ is an ethylene, a cis-vinylene, a trimethylene or a tetramethylene, said hydrocarbon radical $L_3$ being unsubstituted or substituted by one or two methyl groups;

$L_4$ is an ethylene or a trimethylene, said hydrocarbon radical $L_4$ being unsubstituted or substituted by one or two methyl groups;

$L_5$ is a prop-2-en-1-yliden-3-yl which is unsubstituted or substituted by one or two methyl groups;

$L_6$ is a cis-vinylene which is unsubstituted or substituted by one or two methyl groups; and $L_7$ is a methine which is unsubstituted or substituted by a $(C_1-C_3)$alkyl;

ix—or a group $B_9$ of the formula

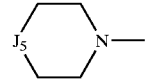

in which $J_5$ is:

a group

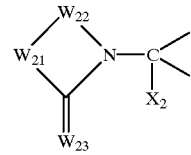

in which:

$X_2$ is a $(C_1-C_6)$alkyl; a group —$CH_2$—$OR_{68}$; a group —$CH_2$—$SR_{68}$; a group —$CH_2$—$S(O)R_{69}$; a group —$CH_2$—$SO_2R_{69}$; a group —$COOR_{68}$; a group —$C(=W_{24})NR_{70}R_{71}$; a group —$C(R_{68})(OR_{72})(OR_{73})$; a group —$CH_2NR_{68}C(=W_{24})R_{74}$; a group —$CH_2$—$NR_{68}COOR_{74}$; or a group —$CH_2NR_{68}C(=W_{24})NR_{70}R_{71}$;

$W_{21}$ is a direct bond and $W_{22}$ is a hydrocarbon radical of which the 1-position is joined to $W_{21}$, the hydrocarbon radical $W_{22}$ being selected from a trimethylene, a tetramethylene, a cis-1-butenylene and a cis,cis-butadienylene;

or $W_{21}$ is a group $NR_{75}$ and $W_{22}$ is a hydrocarbon radical selected from an ethylene, a trimethylene and a cis-vinylene;

or $W_{21}$ is a nitrogen atom and $W_{22}$ is a cis,cis-prop-2-en-1-yliden-3-yl radical of which the 1-position is joined to $W_{21}$;

$W_{23}$ is an oxygen atom or a sulfur atom;

$W_{24}$ is an oxygen atom or a sulfur atom;

$R_{68}$ is a hydrogen or a $(C_1-C_6)$alkyl;

$R_{69}$ is a $(C_1-C_6)$alkyl;

$R_{70}$ and $R_{71}$, are each independently a hydrogen; a $(C_1-C_6)$alkyl which is unsubstituted or substituted by a hydroxyl or a $(C_1-C_3)$alkoxy; an ω—HO—$(C_1-C_6)$alkyl; an ω-$(C_1-C_3)$alkoxy-$(C_1-C_6)$alkyl; an ωphenyl-$(C_1-C_6)$alkyl; an ω—$R_{76}$OOC—$(C_1-C_6)$alkyl; or an ω—$R_{77}R_{78}$NCO—$(C_1-C_6)$alkyl;

or $R_{70}$ and $R_{71}$, together with the nitrogen atom to which they are bonded, form a heterocycle selected from pyrrolidine, piperidine, morpholine, thiomorpholine (or its S-oxide) and piperazine which is unsubstituted or substituted in the 4-position by a methyl group or an ethyl group;

$R_{72}$ and $R_{73}$ are each independently a $(C_1-C_3)$alkyl;

or $R_{72}$ and $R_{73}$ together form a divalent hydrocarbon radical selected from an ethylene and a trimethylene;

$R_{74}$ is a hydrogen or a $(C_1-C_6)$alkyl;

$R_{75}$ is a hydrogen or a $(C_1-C_6)$alkyl;

$R_{76}$ is a hydrogen or a $(C_1-C_3)$alkyl; and $R_{77}$ and $R_{78}$ are each independently a hydrogen or a $(C_1-C_3)$alkyl;

x—or a group $B_{10}$ of the formula

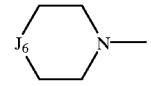

in which $J_6$ is:
a group

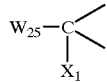

in which:
$X_1$ is as defined above for the group $B_1$, $X_1$ being other than hydrogen when $W_{25}$ is a $(C_1-C_7)$alkyl or a $(C_3-C_7)$cycloalkyl;
$W_{25}$ is a $(C_1-C_7)$alkyl or a $(C_3-C_7)$cycloalkyl; $W_{25}$ can also be a group —$NR_{79}R_{80}$ when $X_1$ is a hydrogen, a cyano, a carboxyl, a $(C_1-C_7)$alkoxycarbonyl or a group —$CONR_{19}R_{20}$; and
$R_{79}$ and $R_{80}$ are each independently a $(C_1-C_7)$alkyl;
or $R_{79}$ and $R_{80}$, together with the nitrogen atom to which they are bonded, form a heterocycle selected from azetidine, pyrrolidine, piperidine, morpholine, thiomorpholine and perhydroazepine,
with the proviso that:
1/when simultaneously:
$R_2$ is a methyl group or $R_1$ and $R_2$ together form a group —$(CH_2)_3$—;
$Ar_1$ is a 3,4-dichlorophenyl;
T is a group —$CH_2$—; a group —CO—; a group —COO—; or a group —$CONR_3$;
A is a direct bond; a group —$(CH_2)_t$— in which t is one, two or three; or a vinylene group;
or —T—A— is the group —$SO_2$—; and
Z is a phenyl which is unsubstituted or monosubstituted or polysubstituted by a halogen, a $(C_1-C_4)$alkyl, a $(C_1-C_4)$alkoxy or a nitro,
B is a group $B_1$ of the formula

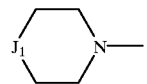

in which $J_1$ is a group

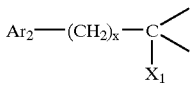

in which:
x is zero;
$Ar_2$ is a pyrid-2-yl or a phenyl which is unsubstituted or substituted by a halogen, a methyl or a $(C_1-C_4)$alkoxy; and
$X_1$ is other than a group selected from:
formyl;
$(C_1-C_6)$alkylcarbonyl;
—$(CH_2)_m$—$OR_4$ in which m is zero or one and $R_4$ is a hydrogen or a $(C_1-C_7)$alkyl;
—$(CH_2)_m$—$OCOR_5$ in which m is zero or one and $R_5$ is a hydrogen or a $(C_1-C_6)$alkyl;
—$(CH_2)_m$—$OCONH(C_1-C_7)$alkyl in which m is one;
—$NR_8R_9$ in which $R_8$ and $R_9$ are each independently a hydrogen or a $(C_1-C_7)$alkyl;
$R_9$ can also be a $(C_3-C_7)$cycloalkylmethyl, a benzyl or a phenyl; or $R_8$ and $R_9$, together with the nitrogen atom to which they are bonded, form a heterocycle selected from azetidine, pyrrolidine, piperidine, morpholine, thiomorpholine and perhydroazepine;
—$(CH_2)_p$—$NR_{10}R_{11}$ in which p is one and $R_{10}$ and $R_{11}$ are each independently a hydrogen or a $(C_1-C_7)$alkyl; $R_{11}$ can also be a $(C_3-C_7)$cycloalkylmethyl or a benzyl;
—$NR_{12}COR_{13}$ in which $R_{12}$ is a hydrogen or a $(C_1-C_4)$alkyl and $R_{13}$ is a hydrogen, a $(C_1-C_7)$alkyl, a phenyl, a benzyl, a pyridyl or a $(C_3-C_7)$cycloalkyl which is unsubstituted or substituted by one or more methyls; or $R_{12}$ and $R_{13}$ together are a group —$(CH_2)_u$— in which u is three or four;
—$(CH_2)_p$—$NR_{14}C(=W_1)R_{16}$ in which p is one, $W_1$ is an oxygen atom, $R_{14}$ is a hydrogen or a $(C_1-C_4)$alkyl and $R_{16}$ is a hydrogen, a $(C_1-C_7)$alkyl, a phenyl, a benzyl, a pyridyl or a $(C_3-C_7)$cycloalkyl which is unsubstituted or substituted by one or more methyls;
—$(CH_2)_m$—$NR_{14}COOR_{17}$ in which m is zero or one, $R_{14}$ is a hydrogen or a $(C_1-C_4)$alkyl and $R_{17}$ is a $(C_1-C_7)$alkyl or a phenyl;
—$(CH_2)_m$—$NR_{14}SO_2R_{18}$ in which m is zero or one, $R_{14}$ is a hydrogen or a $(C_1-C_4)$alkyl and $R_{18}$ is a $(C_1-C_7)$alkyl, an amino which is free or substituted by one or two $(C_1-C_7)$alkyls, or a phenyl which is unsubstituted or monosubstituted or polysubstituted by a substituent selected from a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$alkylcarbonyloxy, a cyano, a nitro and an amino which is free or substituted by one or two $(C_1-C_7)$alkyls, said substituents being identical or different;
—$(CH_2)_m$—$NR_{14}C(=W_1)NR_{19}R_{20}$ in which m is zero or one, $W_1$ is an oxygen atom, $R_{14}$ is a hydrogen or a $(C_1-C_4)$alkyl and $R_{19}$ and $R_{20}$ are each independently a hydrogen or a $(C_1-C_7)$alkyl; $R_{20}$ can also be a $(C_3-C_7)$cycloalkyl, a $(C_3-C_7)$cycloalkylmethyl, a hydroxyl, a $(C_1-C_4)$alkoxy, a benzyl or a phenyl; or $R_{19}$ and $R_{20}$, together with the nitrogen atom to which they are bonded, form a heterocycle selected from azetidine, pyrrolidine, piperidine, morpholine, thiomorpholine and perhydroazepine;
—$(CH_2)_n$—$COOR_2$, in which n is zero and $R_{21}$ is a $(C_1-C_7)$alkyl;
—$(CH_2)_n$—$C(=W_1)NR_{19}R_{20}$ in which n is zero, $W_1$ is an oxygen atom and $R_{19}$ and $R_{20}$ are as defined above; and —CN;
or $X_1$ does not form a double bond between the carbon atom to which it is bonded and the adjacent carbon atom of the piperidine ring;
or $Ar_2$ and $X_1$, together with the carbon atom to which they are bonded, are other than a group of the formula

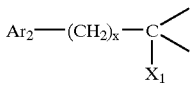

2/when $R_1$ is hydrogen, $R_2$ is the methyl group, $Ar_1$ is other than 3,4-dichlorophenyl group and T—A—Z is the thenoyl group, B is the group $B_1$ in which $J_1$ is the group

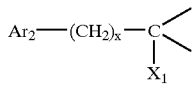

in which x is one, Ar$_2$ is the phenyl group and X$_1$ is other than hydrogen;

3/when R$_1$ is hydrogen, R$_2$ is the methyl group, Ar$_1$ is the 3,4-dichlorophenyl group and T—A—Z is the 2,4-dichlorobenzoyl group, B is the group B$_1$ in which J$_1$ is the group

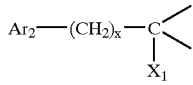

in which x is one, Ar$_2$ is the phenyl group and X$_1$ is other than hydrogen; or 4/when R$_1$ and R$_2$ together form a group —(CH$_2$)$_3$—, Ar$_1$ is the 3,4-dichlorophenyl group and T—A—Z is the 2-(3-methoxyphenyl)acetyl group, B is the group B$_1$ in which J$_1$ is the group

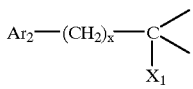

in which x is one, Ar$_2$ is phenyl and X$_1$ is other than hydrogen; and their salts, where appropriate, with mineral or organic acids.

The compounds of formula (I) according to the invention include the optically pure isomers as well as the racemates.

It is possible to form salts of the compounds of formula (I). These salts include those with mineral or organic acids which permit a suitable separation or crystallization of the compounds of formula (I), such as picric acid, oxalic acid or an optically active acid, for example a mandelic or campho-sulfonic acid, as well as those with mineral or organic acids which form pharmaceutically acceptable salts such as the hydrochloride, hydrobromide, sulfate, hydrogensulfate, dihydrogenphosphate, methanesulfonate, methylsulfate, maleate, fumarate, naphthalene-2-sulfonate, glycolate, gluconate, citrate, isethionate, benzenesulfonate and para-toluenesulfonate.

More particularly, the radical Z can be a phenyl group, which can be unsubstituted or may contain one or more substituents.

When Z is a phenyl group, it can be monosubstituted or disubstituted, especially in the 2,4-position but also, for example, in the 2,3-, 4,5-, 3,4- or 3,5-position; it can also be trisubstituted, especially in the 2,4,6-position but also, for example, in the 2,3,4-, 2,3,5-, 2,4,5- or 3,4,5-position, tetrasubstituted, for example in the 2,3,4,5-position, or pentasubstituted.

The radical Z can also be a bicyclic aromatic group such as 1- or 2-naphthyl or 1-, 2-, 3-, 4-, 5-, 6- or 7-indenyl, in which one or more bonds can be hydrogenated, it being possible for said groups to be unsubstituted or optionally to contain one or more substituents such as alkyl, phenyl, cyano, hydroxyalkyl, hydroxyl, oxo, alkylcarbonylamino, alkoxycarbonyl, thioalkyl, halogen, alkoxy and trifluoromethyl groups, in which the alkyls are C$_1$–C$_4$.

The radical Z can also be a group Z' selected from pyridyl, thiadiazolyl, indolyl, indazolyl, imidazolyl, benzimidazolyl, benzotriazolyl, benzofuranyl, benzothienyl, benzothiazolyl, benzisothiazolyl, quinolyl, isoquinolyl, benzoxazolyl, benzisoxazolyl, benzoxazinyl, benzodioxinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl and chromanyl, in which one or more double bonds can be hydrogenated, it being possible for said groups to be unsubstituted or optionally to contain one or more substituents such as alkyl, phenyl, cyano, hydroxyalkyl, hydroxyl, alkylcarbonylamino, alkoxycarbonyl and thioalkyl groups, in which the alkyl and alkoxy groups are C$_1$–C$_4$.

In the present description the alkyl or alkoxy groups are linear or branched; halogen atom is understood as meaning a chlorine, bromine, fluorine or iodine atom.

In the present description, when B is a group B$_4$ or B$_5$, aryl is understood as meaning a phenyl radical or a C$_9$–C$_{10}$ ortho-fused bicyclic carbocyclic radical in which at least one of the rings is aromatic; heteroaryl is understood as meaning either a five- or six-membered monocyclic aromatic heterocycle containing from one to four heteroatoms, said heteroatoms being selected from an oxygen atom, a sulfur atom and a nitrogen atom, and said heterocycle being bonded by a carbon atom of the ring, or an eight- to ten-membered ortho-fused bicyclic aromatic heterocycle containing from one to four heteroatoms as defined above.

In the substituents of the group Z=phenyl, (C$_1$–C$_{10}$)alkyl is understood as meaning for example a methyl, an ethyl, an n-propyl, an isopropyl, an n-butyl, an isobutyl, a sec-butyl, a tert-butyl, a pentyl or n-pentyl, a hexyl or n-hexyl, a heptyl or n-heptyl, an octyl or n-octyl, a nonyl or n-nonyl or a decyl or n-decyl; (C$_3$–C$_8$)-cycloalkyl optionally substituted by a methyl is understood as meaning for example a cyclopropyl, a cyclobutyl, a cyclopentyl, a 1-, 2- or 3-methylcyclopentyl, a cyclohexyl, a 1-, 2-, 3- or 4-methylcyclohexyl, a cycloheptyl or a cyclooctyl; (C$_1$–C$_{10}$)alkoxy is understood as meaning for example a methoxy, an ethoxy, an n-propoxy, an isopropoxy, an n-butoxy, an isobutoxy, a sec-butoxy, a tert-butoxy, a pentoxy, a hexyloxy, a heptyloxy, an octyloxy, a nonyloxy or a decyloxy; (C$_3$–C$_8$)cycloalkoxy optionally substituted by a methyl is understood as meaning for example a cyclopropoxy, a cyclobutoxy, a cyclopentoxy, a 1-, 2- or 3-methylcyclopentoxy, a cyclohexyloxy, a 1-, 2-, 3- or 4-methylcyclohexyloxy, a cycloheptyloxy or a cyclooctyloxy; (C$_1$–C$_{10}$)alkylthio is understood as meaning for example a methylthio, an ethylthio, an n-propylthio, an isopropylthio, an n-butylthio, an isobutylthio, a sec-butylthio, a tert-butylthio, a pentylthio, a hexylthio, a heptylthio, an octylthio, a nonylthio or a decylthio; (C$_1$–C$_6$) alkylcarbonyloxy is understood as meaning for example an acetoxy, a propionyloxy, a butyryloxy, a valeryloxy, a caproyloxy or a heptanoyloxy; (C$_1$–C$_6$)alkylcarbonylamino is understood as meaning for example an acetylamino, a propionylamino, a butyrylamino, an isobutyrylamino, a valerylamino, a caproylamino or an heptanoylamino; (C$_1$–C$_4$)alkoxycarbonyl is understood as meaning for example a methoxycarbonyl, an ethoxycarbonyl, an n-propoxycarbonyl, an isopropoxycarbonyl, an n-butoxycarbonyl, an isobutoxycarbonyl, a sec-butoxycarbonyl or a tert-butoxycarbonyl; and (C$_3$–C$_7$) cycloalkoxycarbonyl is understood as meaning for example a cyclopropoxycarbonyl, a cyclobutoxycarbonyl, a cyclopentoxycarbonyl, a cyclohexyloxycarbonyl or a cycloheptyloxycarbonyl.

The invention relates particularly to compounds of formula (I) in which:

Z is Z˙ as defined above;
R₁ and R₂ together form a group —(CH₂)₃—;
Ar₁ is a 3,4-dichlorophenyl;
T is a group —CO—;
A is a direct bond; and
B is as defined for a compound of formula (I), and their salts, where appropriate, with mineral or organic acids.

Among these compounds, those of the formula

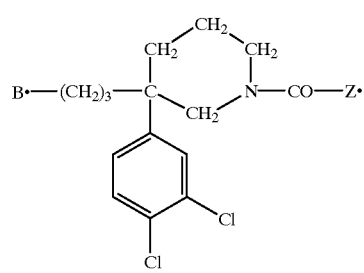

(I•)

in which:
Z˙ is as defined above; and
B˙ is a group of the formula

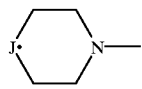

in which J˙ is:
i˙—either a group of the structure

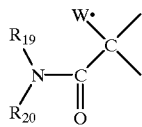

in which:
W˙ is a phenyl or a benzyl and R₁₉ and R₂₀ are as defined for a compound of formula (J);
or W˙ is a group —NR₇₉R₈₀ in which R₇₉ and R₈₀ are as defined for (I) and Rk₁₉ and R₂₀ are each hydrogen;
i˙˙—or a group of the structure

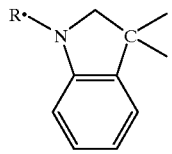

in which:
R˙ is hydrogen, a methyl group, an acetyl group, a methoxycarbonyl group, a dimethylaminocarbonyl group or a methanesulfonyl group,
and their salts, especially pharmaceutically acceptable salts, are advantageous.

Among these compounds, those of the formula

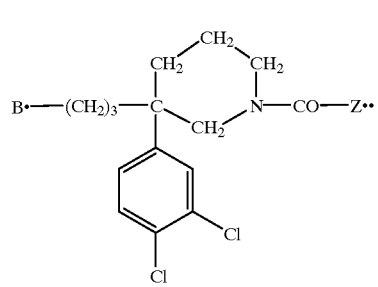

(I••)

in which:
B˙ is as defied for a compound of formula (I˙); and
Z˙˙ is a pyridyl, for example a 4-pyridyl, a 2-thienyl, a 3-thienyl, a 2-furyl or a 3-furyl,
and their salts, especially pharmaceutically acceptable salts, are particularly advantageous.

Among, these compounds, those of the formula

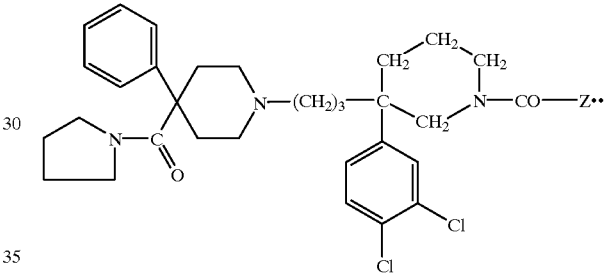

(I••a)

in which:
Z˙˙ is as defined for a compound of formula (I˙˙), and their salts, especially pharmaceutically acceptable salts, are of very great interest.

Advantageously the radical Z is a phenyl which is unsubstituted or monosubstituted or polysubstituted by a halogen atom, more particularly a chlorine, fluorine or iodine atom, a trifluoromethyl, a $(C_1-C_4)$alkyl, a hydroxyl or a $(C_1-C_4)$alkoxy; a naphthyl which is unsubstituted or monosubstituted or polysubstituted by a halogen, a trifluoromethyl, a $(C_1-C_4)$alkyl, a hydroxyl or a $(C_1-C_4)$alkoxy; a pyridyl; a thienyl; an indolyl; a quinolyl; a benzothienyl; or an imidazolyl.

The invention relates particularly to compounds of formula (I) in which:
Z is Z' and is:
a phenyl which is unsubstituted or monosubstituted or polysubstituted by a substituent selected from a halogen atom; a trifluoromethyl; a cyano; a hydroxyl; a nitro; an amino which is unsubstituted or monosubstituted or disubstituted by a $(C_1-C_4)$alkyl; a benzylamino; a carboxyl; a $(C_1-C_{10})$alkyl; a $(C_3-C_8)$cycloalkyl which is unsubstituted or monosubstituted or polysubstituted by a methyl; a $(C_1-C_{10})$alkoxy; a $(C_3-C_8)$cycloalkoxy which is unsubstituted or monosubstituted or polysubstituted by a methyl; a mercapto; a $(C_1-C_{10})$alkylthio; a formyloxy; a $(C_1-C_6)$alkylcarbonyloxy; a formylamino; a $(C_1-C_6)$alkylcarbonylamino; a benzoylamino; a $(C_1-C_4)$alkoxycarbonyl; a $(C_3-C_7)$ cycloalkoxycarbonyl; a carbamoyl which is unsubstituted or monosubstituted or disubstituted by a ($C_1$–$C_4$)alkyl; a ureido which is unsubstituted or monosubstituted or disubstituted in the 3-position by a ($C_1$–$C_4$)alkyl or a ($C_3$–$C_7$)cycloalkyl; and a (pyrrolidin-1-yl)-carbonylamino, said substituents being identical or different;

a naphthyl which is unsubstituted or monosubstituted or polysubstituted by a halogen, a trifluoromethyl, a ($C_1$–$C_4$)alkyl, a hydroxyl or a ($C_1$–$C_4$)alkoxy; or a pyridyl; a thienyl; an indolyl; a quinolyl; a benzothienyl; or an imidazolyl, and their salts with mineral or organic acids.

The substituent $Ar_1$ is preferably a phenyl group which is advantageously substituted by two chlorine atoms, more particularly in the 3- and 4-positions.

According to the present invention, the preferred compounds are those in which simultaneously:

Z is Z';

$Ar_1$ is a 3,4-dichlorophenyl;

$R_1$ and $R_2$ together form a group —$(CH_2)_3$— or —$(CH_2)_4$—; and

B, T and A are as defined for a compound of formula (I), and their salts, especially pharmaceutically acceptable salts.

When B is a group $B_3$, $W_3$ is advantageously an oxygen or sulfur atom, $R_{28}$ is hydrogen, a ($C_1$–$C_6$)alkyl, a ($C_3$–$C_7$)cycloalkyl, preferably cyclohexyl, or a ($C_3$–$C_4$)alk-2-en-1-yl, preferably allyl, and $R_{29}$ is hydrogen, a ($C_1$–$C_6$)alkyl, a trifluoromethyl or a ($C_1$–$C_4$)alkylamino, preferably methylamino, or, only when $R_{28}$ is other than hydrogen, $R_{29}$ is a di($C_1$–$C_5$)alkylamino, preferably dimethylamino, or $R_{28}$ and $R_{29}$ together are a 1,3-propylene, 1,4-butylene or cis,cis-1,4-butadienylene group. Consequently the compounds of formula (I) in which B is $B_3$ and $W_3$, $R_{28}$ and $R_{29}$ are as just defined, and their salts, especially pharmaceutically acceptable salts, are advantageous products.

The compounds of this subclass of formula (I) in which simultaneously:

B is a group $B_3$ in which:
   either $W_3$ is oxygen, $R_{29}$ is a ($C_1$–$C_4$)alkyl or a trifluoromethyl and $R_{28}$ is a ($C_1$–$C_6$)alkyl, especially an ethyl;
   or $W_3$ is oxygen, $R_{28}$ is an allyl or a cyclohexyl and $R_{29}$ is a methyl;
   or $W_3$ is oxygen, $R_{28}$ is an ethyl and $R_{29}$ is a methylamino or a dimethylamino;
   or $W_3$ is oxygen and $R_{28}$ and $R_{29}$ together form a 1,3-propylene, 1,4-butylene or cis,cis-1,4-butadienyl group;
   or $W_3$ is sulfur and $R_{28}$ and $R_{29}$ together form a 1,4-butylene group;

$R^1$ and $R_2$ together form a group —$(CH_2)_3$— or —$(CH_2)_4$—;

$Ar_1$ is a 3,4-dichlorophenyl;

Z=Z'; and

T and A are as defined above for a compound of formula (I), and their salts, especially pharmaceutically acceptable salts, are particularly preferred.

When B is a group $B_4$, $W_4$ is advantageously a ($C_1$–$C_8$) alkyl group substituted by a hydroxyl, oxo, hydroxyimino, ($C_1$–$C_4$)alkoxyimino, ($C_1$–$C_4$)alkanoyloxy, ($C_1$–$C_4$) alkanoylamino or ($C_1$–$C_4$)alkoxy group or at the same time by an oxo group and a hydroxyl or ($C_1$–$C_4$)alkoxy group or a group —$NR_{33}R_{34}$. Consequently the compounds of formula (I) in which B is a group $B_4$ and $W_4$ is an alkyl group substituted by a hydroxyl, oxo, hydroxyimino, ($C_1$–$C_4$) alkoxyimino, ($C_1$–$C_4$)alkanoyloxy, ($C_1$–$C_4$)alkanoylamino or ($C_1$–$C_4$)alkoxy group or at the same time by an oxo group and a hydroxyl or ($C_1$–$C_4$)alkoxy group or a group —$NR_{33}R_{34}$, and their salts, especially pharmaceutically acceptable salts, are advantageous products.

The compounds of this subclass of formula (I) in which simultaneously:

B is $B_4$ in which: $W_4$ is 1-hydroxypropyl, 1-hydroxyethyl, 1-hydroxybutyl, 2-hydroxybut-2-yl, 4-hydroxyhept-4-yl, 2-hydroxyethyl, 1-hydroxyiminopropyl (syn or anti), 1-methoxyiminopropyl (syn or anti), 2-acetoxyethyl, 2-acetamidoethyl, carboxyl, ethoxycarbonyl or pyrrolidin-1-ylcarbonyl;

$R_1$ and $R_2$ together form a group —$(CH_2)_3$— or —$(CH_2)_4$—;

$Ar_1$ is a 3,4-dichlorophenyl;

Z=Z'; and

T and A are as defined above for a compound of formula (I), and their salts, especially pharmaceutically acceptable salts, are particularly preferred.

When B is a group $B_5$, $W_6$ is advantageously a hydrogen, $W_7$ is a hydroxyl and $W_8$ is a phenyl which is unsubstituted or substituted by a methoxy, a hydroxyl, a methylthio or a methylsulfinyl; or $W_6$ and $W_7$ are hydrogen and $W_8$ is a pyridyl, pyrimidyl or thienyl group substituted by a halogen, especially chlorine or fluorine, or by one of the following groups: cyano, trifluoromethyl, hydroxyl, ($C_1$–$C_5$)alkoxy, especially methoxy or ethoxy, formyloxy, ($C_1$–$C_4$) alkylcarbonyloxy, especially acetoxy, amino, methylamino, dimethylamino, acetamido, imidazolin-2-yl, carboxyl, methoxycarbonyl, benzyloxycarbonyl, ethoxycarbonyl, carbamoyl, N,N-dimethylcarbamoyl, pyrrolidinocarbonyl, N-methylcarbamoyl, methylthio, methylsulfinyl, methylsulfonyl, ($C_1$–$C_4$)alkyl, especially methyl, ethyl, propyl, butyl, isopropyl, 2-methylpropyl or tert-butyl, formyl or ($C_1$–$C_4$)alkylcarbonyl, especially acetyl or propionyl; an indenyl, naphthyl, furyl, pyrrolyl, 1,3,4-oxadiazol-2-yl or benz[d]isoxazol-3-yl group which is unsubstituted or substituted by one of the substituents mentioned above for the pyridyl, pyrimidyl or thienyl groups; an imidazol-2-yl substituted by one of the substituents mentioned above for the pyridyl, pyrimidyl or thienyl groups, except for a ($C_1$–$C_4$)alkyl; or a phenyl group substituted by one of the substituents mentioned above for the pyridyl, pyrimidyl or thienyl groups, except for halogens and hydroxyl, trifluoromethyl, ($C_1$–$C_4$)alkyl and ($C_1$–$C_4$)alkoxy groups; or $W_7$ is hydrogen and $W_6$ and $W_8$, together with a diradical $W_9$ and the piperidine carbon atom to which they are bonded, form a spiro ring in which $W_8$ is a phenyl substituted in the ortho position by the diradical $W_9$, which is itself joined to $W_6$, said phenyl being unsubstituted or substituted by a methoxy, a hydroxyl, a methylthio or a methylsulfinyl; the diradical $W_9$ is a methylene or a carbonyl; and $W_6$ is an oxy group. Consequently the compounds of formula (I) in which B is $B_5$ and $W_6$, $W_7$ and $W_8$ are as just defined, and their salts, especially pharmaceutically acceptable salts, are advantageous products.

The compounds of this subclass of formula (I) in which simultaneously:

B is a group $B_5$ in which: $W_7$ is a hydroxyl, $W_6$ is a hydrogen and $W_8$ is a phenyl; or $W_6$ and $W_7$ are hydrogen and $W_8$ is selected from the following groups; 5-methyl-1,3,4-oxadiazol-2-yl, 4-ethoxycarbonylimidazol-2-yl, 2-fluoropyrid-3-yl, 2-methylthiophenyl, 4-methylthiophenyl, 2-methylsulfinylphenyl, 4-methylsulfinylphenyl and 4-(N-methylcarbamoyl)phenyl; or $W_7$ is hydrogen and $W_6$ and $W_8$, together with the piperidine to which they are bonded, form a spiro[isobenzofuran-1(3H),4'-piperid]-1'-yl group or a 3-oxospiro[isobenzofuran-1(3H),4'-piperid]-1'-yl group;

$R_1$ and $R_2$ together form a group —$(CH_2)_3$— or —$(CH_2)_4$—;

$Ar_1$ is a 3,4-dichlorophenyl;

$Z=Z'$; and

T and A are as defined above for a compound of formula (I), and their salts, especially pharmaceutically acceptable salts, are particularly preferred.

Another group of preferred compounds of the invention consists of the compounds of formula (I) in which $R_1$, $R_2$, $Ar_1$, T, A and Z are as defined above for (J) and B is the group $B_6$.

The particularly preferred compounds of formula (I) are those in which simultaneously:

B is a group $B_6$;

$R_1$ and $R_2$ together form a group —$(CH_2)_3$— or —$(CH_2)_4$—;

$Ar_1$ is a 3,4-dichlorophenyl;

$Z=Z'$; and

T and A are as defined above for a compound of formula (I), and their salts, especially pharmaceutically acceptable salts.

When B is a group $B_7$, f is advantageously one and g is two, or f is one and g is one and $W_{12}$, $W_{13}$, $W_{14}$, $W_{15}$ and $W_{16}$, together with the carbon atom to which they are bonded, form one of the structures 1 to 201 described below, optionally substituted by a halogen, a $(C_1-C_7)$alkyl or a $(C_1-C_7)$alkoxy:

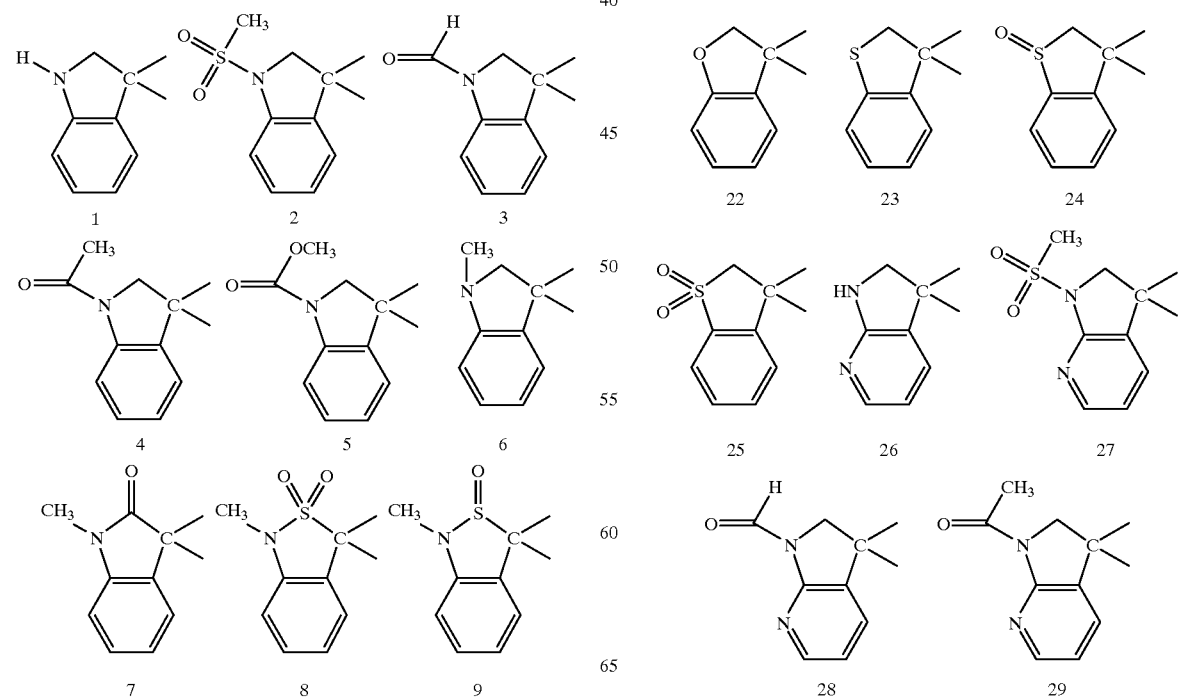

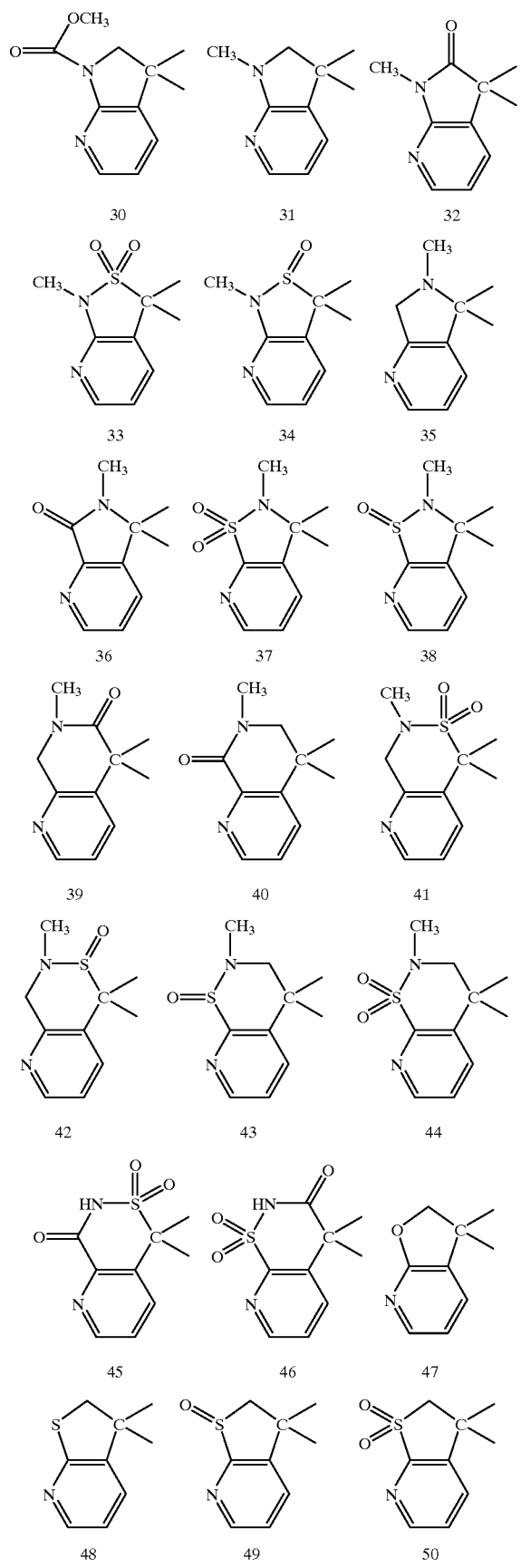
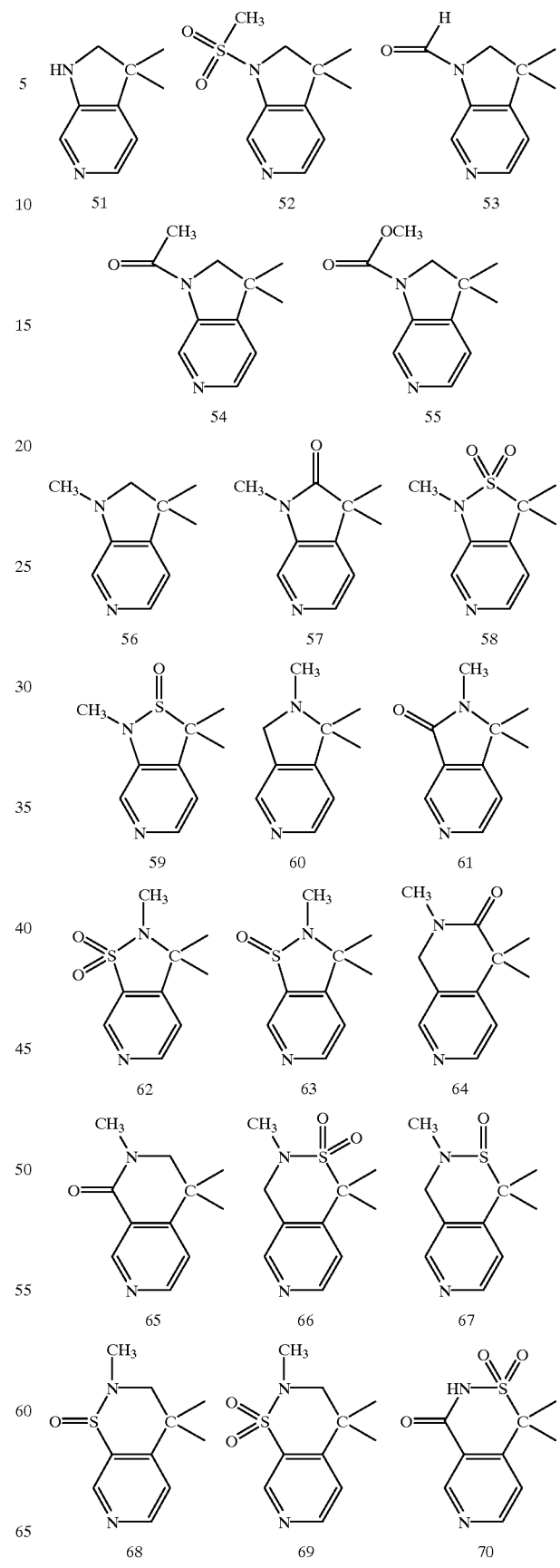

-continued
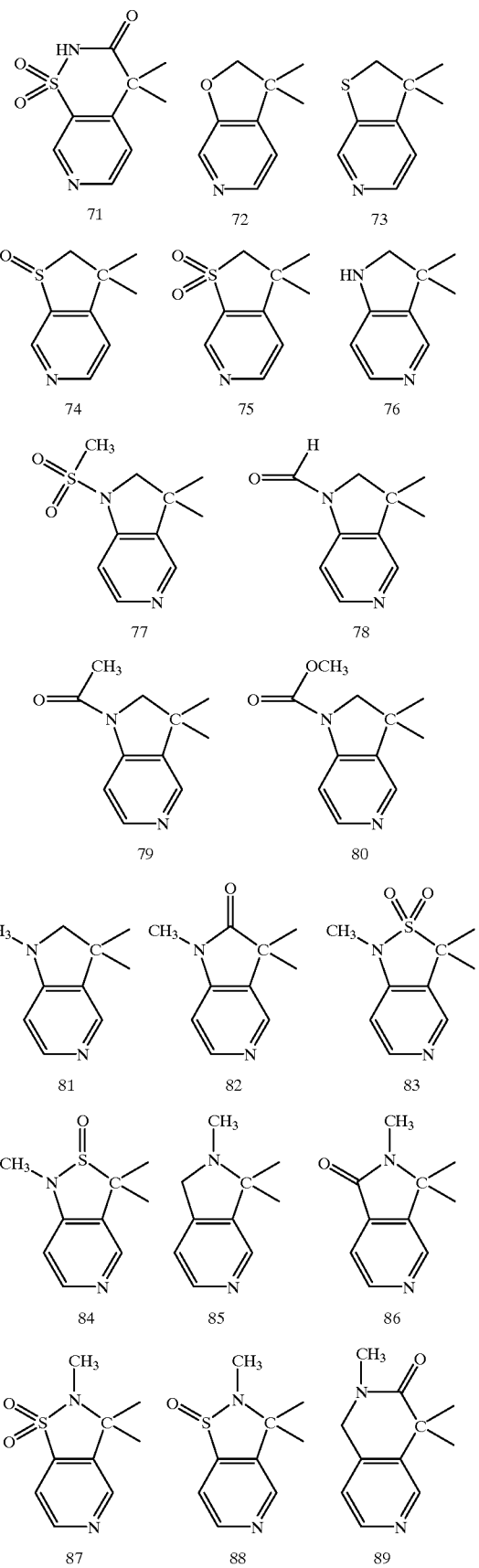
-continued
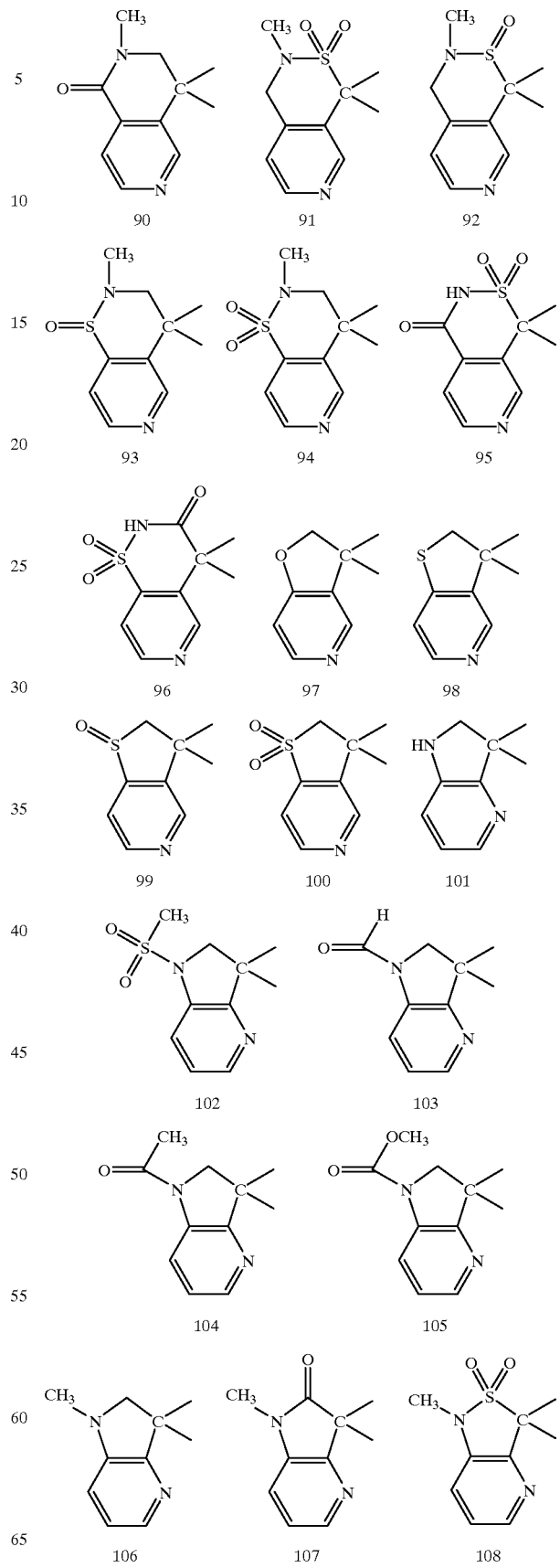

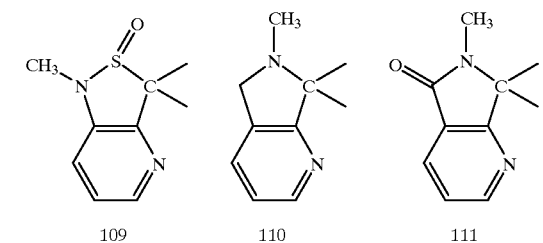
109  110  111
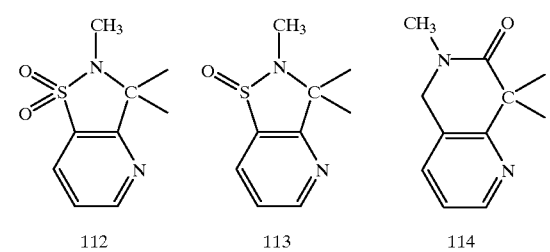
112  113  114
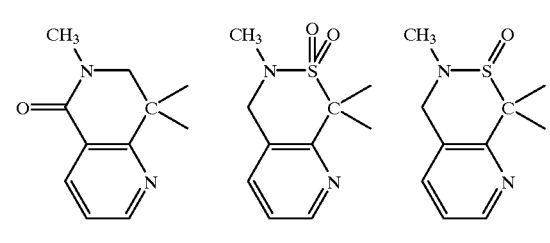
115  116  117
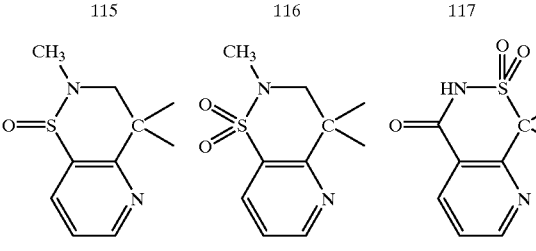
118  119  120
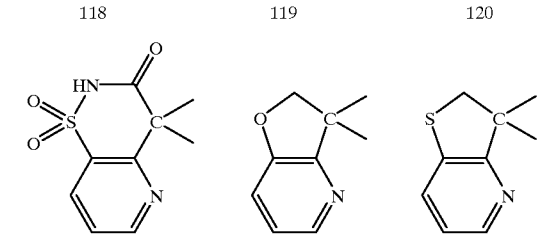
121  122  123
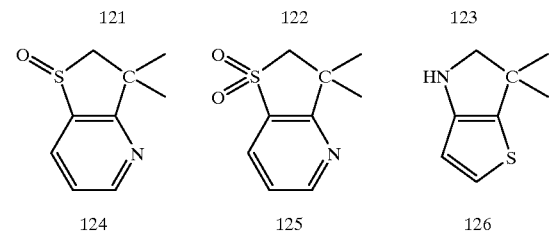
124  125  126
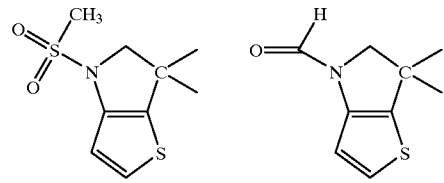
127  128
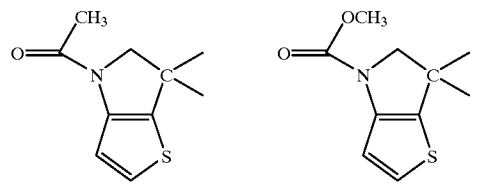
129  130
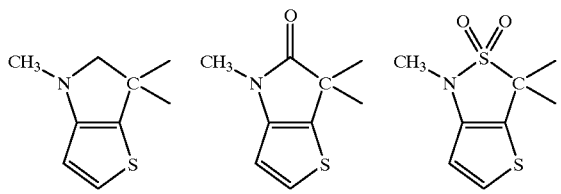
131  132  133
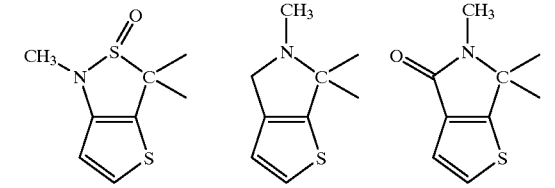
134  135  136
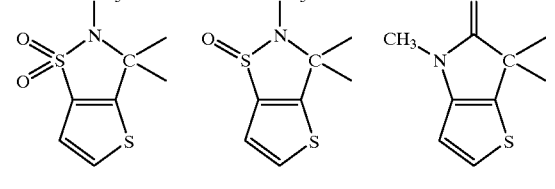
137  138  139
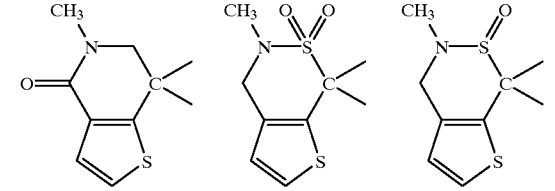
140  141  142
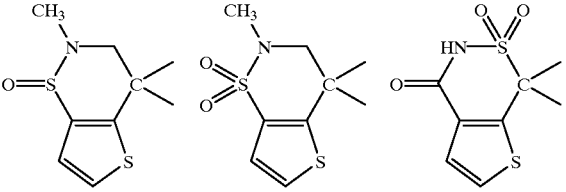
143  144  145
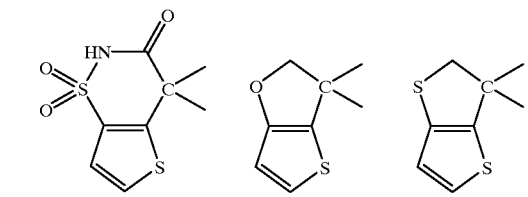
146  147  148

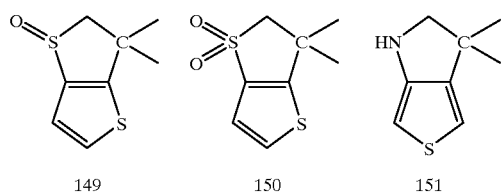
149 150 151
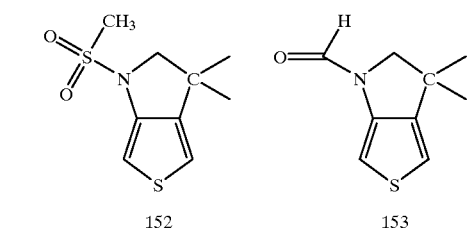
152 153
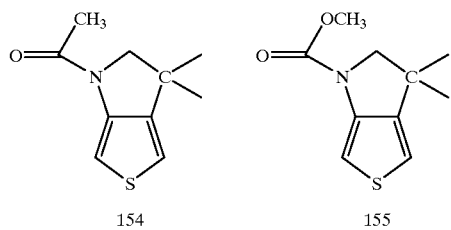
154 155
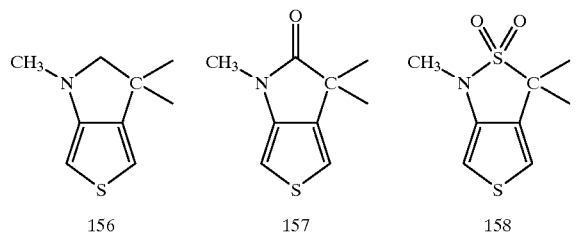
156 157 158
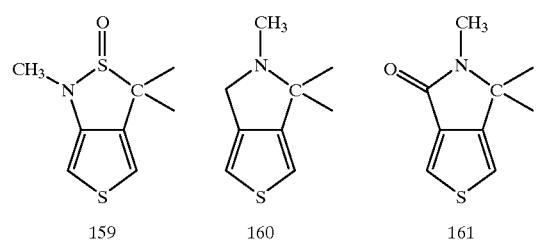
159 160 161
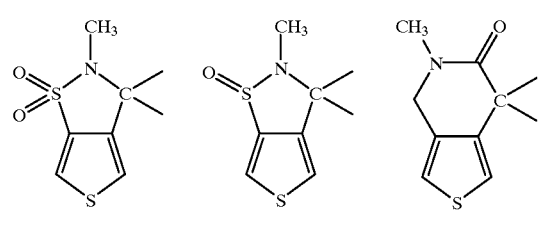
162 163 164
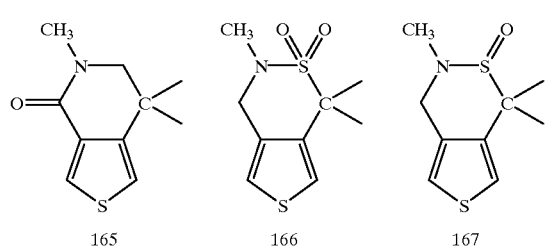
165 166 167
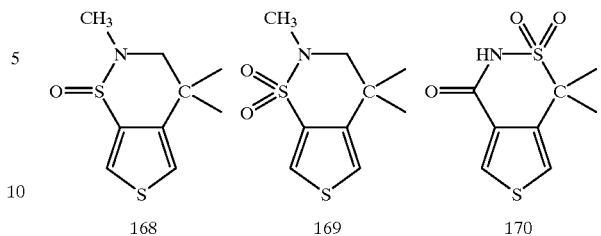
168 169 170
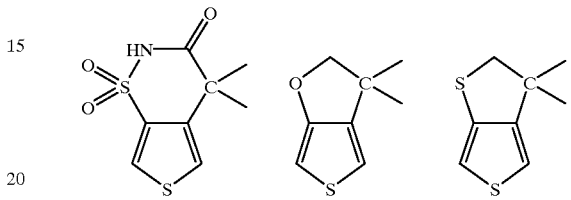
171 172 173
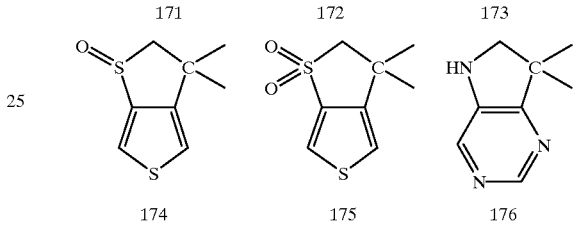
174 175 176
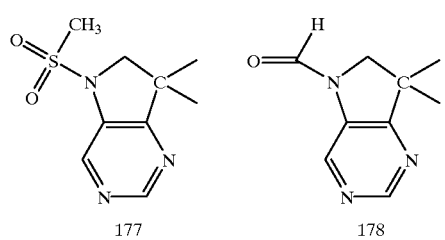
177 178
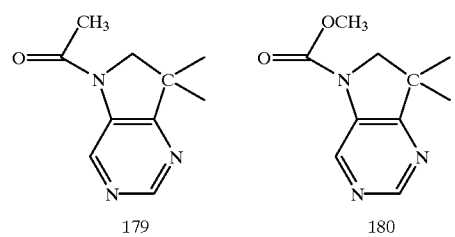
179 180
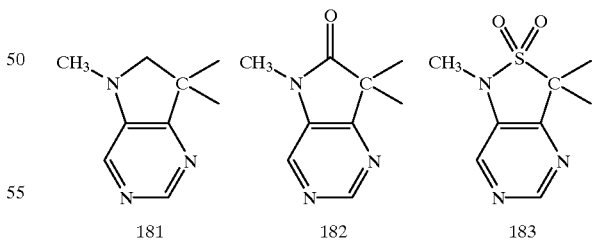
181 182 183
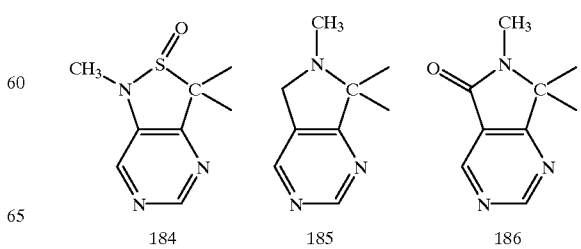
184 185 186

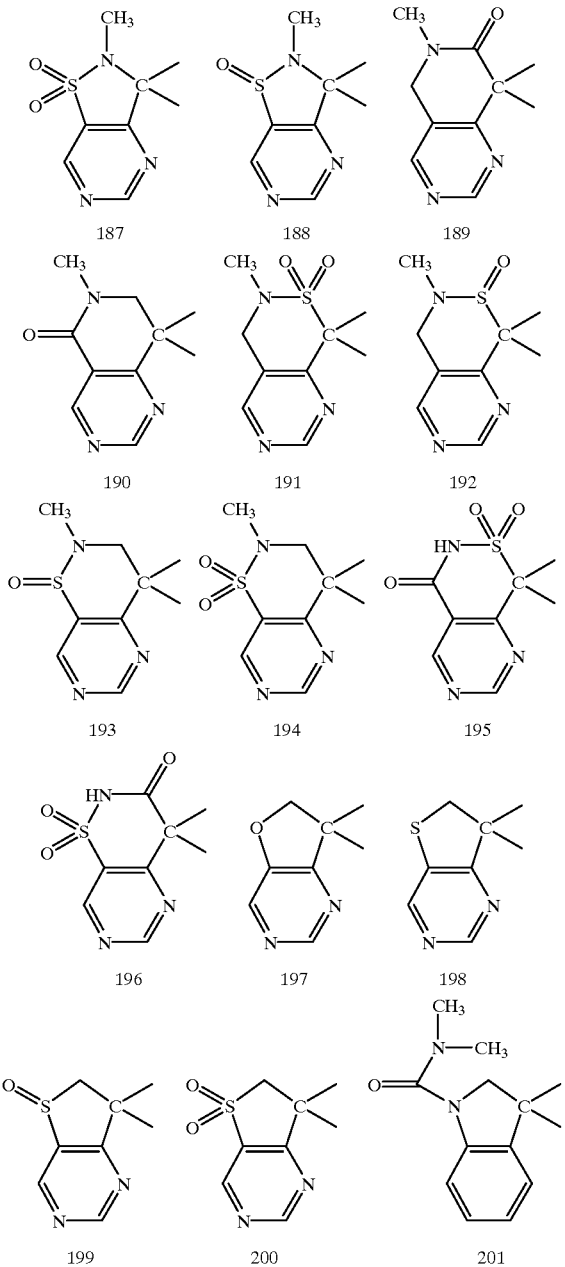

Consequently the compounds of formula (1) in which B is B$_7$ and g, f, W$_{12}$, W$_{13}$, W$_{14}$, W$_{15}$ and W$_{16}$ are as just defined, and their salts, especially pharmaceutically acceptable salts, are advantageous products.

The compounds of this subclass of formula (I) in which simultaneously:

B is a group B$_7$ selected from:
a) a 1-methanesulfonylspiro(indoline-3,4'-piperid-1'-yl)
b) a 1-benzyloxycarbonylspiro(indoline-3,4'-piperid-1'-yl)
c) a spiro(indoline-3,4'-piperid-1'-yl)
d) a 1-acetylspiro(indoline-3,4'-piperid-1'-yl)
e) a 1-propionylspiro(indoline-3,4'-piperid-1'-yl)
f) a 1-formylspiro(indoline-3,4'-piperid-1'-yl)
g) a 1-tert-butylcarbonylspiro(indoline-3,4'-piperid-1'-yl)
h) a 1-methylaminocarbonylspiro(indoline-3,4'-piperid-1'-yl)
i) a 1-ethoxycarbonylspiro(indoline-3,4'-piperid-1'-yl)
j) a 1-ethanesulfonylspiro(indoline-3,4'-piperid-1'-yl)
k) a 1-isopropanesulfonylspiro(indoline-3,4'-piperid-1'-yl)
l) a 1'-methyl-1-methanesulfonylspiro(indoline-3,4'-piperidinio-1') iodide
m) a 1-(2-aminoacetyl)spiro(indoline-3,4'-piperid-1'-yl)
n) a 1-methylspiro(indol-2-one-3,4'-piperid-1'-yl)
o) a 2-methylspiro(isoindol-1-one-3,4'-piperid-1'-yl)
p) a spiro(2-oxotetrahydroquinoline-4-4'-piperid-1'-yl)
q) a 1-methylspiro(2-oxotetrahydroquinoline-4,4'-piperid-1'-yl)
r) a spiro(2,3-dihydrobenzothiophene-3,4'-piperid-1'-yl)
s) a 5-fluorospiro(2,3-dihydrobenzofuran-3,4'-piperid-1'-yl)
t) a spiro(2,3-dihydrobenzofuran-3,4'-piperid-1'-yl)
u) a spiro(2,3-dihydrobenzothiophene-3,4'-piperid-1'-yl)1-oxide
v) a spiro(2,3-dihydrobenzothiophene-3,4'-piperid-1'-yl)1,1-dioxide
w) a 5-fluoro-1-methanesulfonylspiro(indoline-3,4'-piperid-1-yl)
x) a 1-methanesulfonyl-5-methoxyspiro(indoline-3,4'-piperid-1'-yl)
y) a 1-methanesulfonyl-5-methylspiro(indoline-3,4'-piperid-1'-yl)
z) a 5-chloro-1-methanesulfonylspiro(indoline-3,4'-piperid-1'-yl)
aa) a 7-fluoro-1-methanesulfonylspiro(indoline-3,4'-piperid-1'-yl)
ab) a 1-acetyl-5-fluorospiro(indoline-3,4'-piperid-1'-yl)
ac) a 1-acetyl-5-chlorospiro(indoline-3,4'-piperid-1'-yl)
ad) a 1-acetyl-5-methylspiro(indoline-3,4'-piperid-1'-yl)
ae) a 1-acetyl-6-fluorospiro(indoline-3,4'-piperid-1'-yl)
af) a 1-acetyl-4-fluorospiro(indoline-3,4'-piperid-1'-yl)
ag) a 1-(N,N-dimethylcarbamoyl)spiro(indoline-3,4'-piperid-1'-yl);

R$_1$ and R$_2$ together form a group —(CH$_2$)$_3$— or —(CH$_2$)$_4$—;
Ar$_1$ is a 3,4-dichlorophenyl;
Z=Z'; and
T and A are as defined above for (I),
and their salts, especially pharmaceutically acceptable salts, are particularly preferred.

When B is a group B$_8$, W$_{17}$ is advantageously a direct bond or a methylene group, preferably a direct bond, W$_{18}$ is an oxo, thioxo, imino, methylimino or ethylimino group, preferably an oxo or thioxo group, W$_{19}$ is an oxy or thio group or a group NH, preferably an oxy group or a group NH, and W$_{20}$ is an ethylene, cis-vinylene or trimethylene group. Consequently the compounds of formula (I) in which B is B$_8$ and W$_{17}$, W$_{18}$, W$_{19}$ and W$_{20}$ are as just defined, and their salts, especially pharmaceutically acceptable salts, are advantageous products.

The compounds of this subclass of formula (I) in which simultaneously:

B is a group B$_8$ in which: W$_{17}$ is a direct bond, W$_{18}$ is an oxo or thioxo group, W$_{19}$ is an oxy group or a group NH and W$_{20}$ is an ethylene or trimethylene group;

R$_1$ and R$_2$ together form a group —(CH$_2$)$_3$— or —(CH$_2$)$_4$—;

Ar$_1$ is a 3,4-dichlorophenyl;

Z═Z';and

T and A are as defined above for (I), and their salts, especially pharmaceutically acceptable salts, are particularly preferred.

Another group of preferred compounds of the invention consists of the compounds of formula (I) in which R$_1$, R$_2$, Ar$_1$, T, A and Z are as defined above for (I) and B is the group B$_9$.

The particularly preferred compounds of formula (I) are those in which simultaneously:

B is a group B$_9$ in which: X$_2$ is a group —COOR$_{68}$ or a group —C(═W$_{24}$)NR$_{70}$R$_7$, and W$_{21}$, W$_{22}$ and W$_{23}$, together with the nitrogen atom, form a 2-oxopiperidino group or a 2-oxoperhydropyrimidin-1-yl group;

R$_1$ and R$_2$ together form a group —(CH$_2$)$_3$— or —(CH$_2$)$_4$—;

Ar$_1$ is a 3,4-dichlorophenyl;

Z═Z'; and

T and A are as defined above for (I), and their salts, especially pharmaceutically acceptable salts.

Another group of preferred compounds of the invention consists of the compounds of formula (I) in which R$_1$, R$_2$, Ar$_1$, T, A and Z are as defined above for (I) and B is the group B$_{10}$.

The particularly preferred compounds of formula (I) are those in which simultaneously:

B is a group B$_{10}$;

R$_1$ and R$_2$ together form a group —(CH$_2$)$_3$— or —(CH$_2$)$_4$—;

Ar$_1$ is a 3,4-dichlorophenyl;

Z═Z'; and

T and A are as defined above for (I), and their salts, especially pharmaceutically acceptable salts.

The more particularly preferred compounds of formula (I) are those in which simultaneously:

B is a group B$_{10}$ in which J$_6$ is a group

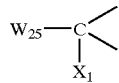

in which:

W$_{25}$ is a piperid-1-yl and X$_1$ is a hydrogen, or W$_{25}$ is an azetidin-1-yl, a pyrrolidin-1-yl, a pirerid-1-yl, a morpholin-4-yl, a thiomorpholin-4-yl or a perhydroazepin-1-yl and X$_1$ is a carbamoyl;

R$_1$ and R$_2$ together form a group —(CH$_2$)$_3$—;

Ar$_1$ is a 3,4-dichlorophenyl;

Z═Z';

T is a group —CO—; and

A is a direct bond, and their salts, especially pharmaceutically acceptable salts.

Another group of preferred compounds of the invention are those of the formula

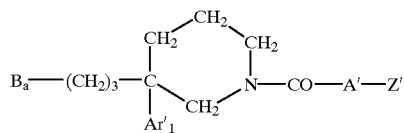

(Ia)

in which:

Ar'$_1$ is a phenyl which is unsubstituted or monosubstituted or polysubstituted by a substituent selected from a halogen atom, a hydroxyl, a (C$_1$–C$_4$)alkoxy, a (C$_1$–C$_4$)-alkyl, a trifluoromethyl and a methylenedioxy, said substituents being identical or different;

A' is a direct bond or a group —CH$_2$—;

Z' is as defined above; and

B$_a$ is a group B$_{1a}$ of the formula

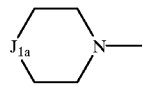

in which J$_{1a}$ is a group

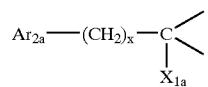

in which:

x is zero;

Ar$_{2a}$ is a phenyl which is unsubstituted or monosubstituted or polysubstituted by a substituent selected from a halogen atom, a hydroxyl, a (C$_1$–C$_4$)alkoxy, a (C$_1$–C$_4$)alkyl, a trifluoromethyl and a methylenedioxy, said substituents being identical or different; and X$_{1a}$ is a group selected from:

hydrogen;

(C$_1$–C$_7$)alkyl;

—(CH$_2$)$_m$—OR$_4$ in which m is two and R$_4$ is a hydrogen or a (C$_1$–C$_7$)alkyl;

—(CH$_2$)$_m$—OCOR$_5$ in which:

m is two and R$_5$ is a hydrogen; a (C$_1$–C$_7$)alkyl; a (C$_3$–C$_7$)cycloalkyl which is unsubstituted or substituted by one or more methyls; a phenyl; or a pyridyl; or m is zero or one and R$_5$ is a (C$_3$–C$_7$) cycloalkyl which is unsubstituted or substituted by one or more methyls; a phenyl; or a pyridyl;

—(CH$_2$)$_m$—OCONH(C$_1$–C$_7$)alkyl in which m is zero or two;

—O—CH$_2$—CH$_2$—OR$_6$ in which R$_6$ is a hydrogen; a (C$_1$–C$_7$)alkyl; a formyl; or a (C$_1$–C$_7$)alkylcarbonyl;

—(CH$_2$)$_n$—SR$_7$ in which n is zero or one and R$_7$ is a hydrogen or a (C$_1$–C$_7$)alkyl;

—CH$_2$—S(O)$_j$—(C$_1$–C$_7$)alkyl in which j is one or two;

—NR$_8$R$_9$ in which R$_8$ and R$_9$, together with the nitrogen atom to which they are bonded, form a piperazine heterocycle which is unsubstituted or substituted in the 4-position by a (C$_1$–C$_4$)alkyl;

—(CH$_2$)$_p$—NR$_{10}$R$_{11}$ in which p is two and R$_{10}$ and R$_{11}$ are each independently a hydrogen or a (C$_1$–C$_7$) alkyl; R$_{11}$ can also be a (C$_3$–C$_7$)cycloalkylmethyl or a benzyl;

—NR$_{12}$COR$_{13}$ in which R$_{12}$ is a hydrogen or a (C$_1$–C$_7$) alkyl and R$_{13}$ is a vinyl, a furyl, a thienyl, a pyrrolyl or an imidazolyl;

—$NR_{14}COCOR_{15}$ in which $R_{14}$ is a hydrogen or a ($C_1$–$C_7$)alkyl and $R_{15}$ is a ($C_1$–$C_4$)alkoxy;

—$(CH_2)_p$—$NR_{14}C(=W_1)R_{16}$ in which p is two, $W_1$ is an oxygen atom or a sulfur atom, $R_{14}$ is a hydrogen or a ($C_1$–$C_7$)alkyl and $R_{16}$ is a hydrogen; a ($C_1$–$C_7$) alkyl; a ($C_3$–$C_7$)cycloalkyl which is unsubstituted or substituted by one or more methyls; a phenyl; a benzyl; a vinyl; a pyridyl; a furyl; a thienyl; a pyrrolyl; or an imidazolyl; and p is one, $W_1$ is a sulfur atom and $R_{14}$ and $R_{16}$ are as just defined, or $W_1$ is an oxygen atom, $R_{14}$ is as just defined and $R_{16}$ is a vinyl, a furyl, a thienyl, a pyrrolyl or an imidazolyl;

—$(CH_2)_m$—$NR_{14}COOR_{17}$ in which m is two, $R_{14}$ is a hydrogen or a ($C_1$–$C_7$)alkyl and $R_{17}$ is a ($C_1$–$C_7$) alkyl or a phenyl;

—$(CH_2)_m$—$NR_{14}SO_2R_{18}$ in which m is two, $R_{14}$ is a hydrogen or a ($C_1$–$C_7$)alkyl and $R_{18}$ is a ($C_1$–$C_7$) alkyl; an amino which is free or substituted by one or two ($C_1$–$C_7$)alkyls; or a phenyl which is unsubstituted or monosubstituted or polysubstituted by a substituent selected from a halogen atom, a ($C_1$–$C_7$) alkyl, a trifluoromethyl, a hydroxyl, a ($C_1$–$C_7$) alkoxy, a carboxyl, a ($C_1$–$C_7$)alkylcarbonyloxy, a cyano, a nitro and an amino which is free or substituted by one or two ($C_1$–$C_7$)alkyls, said substituents being identical or different;

—$(CH_2)_m$—$NR_{14}C(=W_1)NR_{19}R_{20}$ in which m is two, $W_1$ is an oxygen atom or a sulfur atom, $R_{14}$ is a hydrogen or a ($C_1$–$C_7$)alkyl and $R_{19}$ and $R_{20}$ are each independently a hydrogen or a ($C_1$–$C_7$)alkyl; $R_{20}$ can also be a ($C_3$–$C_7$)cycloalkyl; a ($C_3$–$C_7$) cycloalkylmethyl; a hydroxyl; a ($C_1$–$C_4$)alkoxy; a benzyl; a phenyl; or a ($C_1$–$C_7$)alkyl substituted by a hydroxyl, a ($C_1$–$C_3$)alkoxy, a phenyl, a carboxyl, a ($C_1$–$C_3$)alkoxycarbonyl or a carbamoyl which is unsubstituted or substituted by one or two ($C_1$–$C_7$) alkyls; or $R_{19}$ and $R_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a ($C_1$–$C_4$)alkyl; and m is zero or one, $W_1$ is a sulfur atom and $R_{14}$, $R_{19}$ and $R_{20}$ are as just defined, or $W_1$ is an oxygen atom, $R_{14}$ and $R_{19}$ are each independently a hydrogen or a ($C_1$–$C_7$)alkyl and $R_{20}$ is a ($C_1$–$C_7$)alkyl substituted by a hydroxyl, a ($C_1$–$C_3$)alkoxy, a phenyl, a carboxyl, a ($C_1$–$C_3$) alkoxycarbonyl or a carbamoyl which is unsubstituted or substituted by one or two ($C_1$–$C_7$)alkyls; or $R_{19}$ and $R_{20}$, together with the nitrogen atom to which they are bonded, form a piperazine heterocycle which is unsubstituted or substituted in the 4-position by a ($C_1$–$C_4$)alkyl;

—$(CH_2)_n$—$COOR_{21}$ in which n is one and $R_{21}$ is a hydrogen or a ($C_1$–$C_7$)alkyl; and n is zero and $R_{21}$ is a hydrogen;

—$(CH_2)_n$—$C(=W_1)NR_{19}R_{20}$ in which n is one, $W_1$ is an oxygen atom or a sulfur atom and $R_{19}$ and $R_{20}$ are each independently a hydrogen or a ($C_1$–$C_7$)alkyl; $R_{20}$ can also be a ($C_3$–$C_7$)cycloalkyl; a ($C_3$–$C_7$) cycloalkylmethyl; a hydroxyl; a ($C_1$–$C_4$)alkoxy; a benzyl; a phenyl; or a ($C_1$–$C_7$)alkyl substituted by a hydroxyl, a ($C_1$–$C_3$)alkoxy, a phenyl, a carboxyl, a ($C_1$–$C_3$)alkoxycarbonyl or a carbamoyl which is unsubstituted or substituted by one or two ($C_1$–$C_7$) alkyls; or $R_{19}$ and $R_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a ($C_1$–$C_4$)alkyl; and n is zero, $W_1$ is a sulfur atom and $R_{19}$ and $R_{20}$ are as just defined, or $W_1$ is an oxygen atom, $R_{19}$ is a hydrogen or a ($C_1$–$C_7$)alkyl and $R_{20}$ is a ($C_1$–$C_7$)alkyl substituted by a hydroxyl, a ($C_1$–$C_3$)alkoxy, a phenyl, a carboxyl, a ($C_1$–$C_3$)alkoxycarbonyl or a carbamoyl which is unsubstituted or substituted by one or two ($C_1$–$C_7$)alkyls; or $R_{19}$ and $R_{20}$, together with the nitrogen atom to which they are bonded, form a piperazine heterocycle which is unsubstituted or substituted in the 4-position by a ($C_1$–$C_4$)alkyl;

—$CO$—$NR_{22}NR_{23}R_{24}$ in which $R_{22}$ is a hydrogen or a ($C_1$–$C_7$)alkyl and $R_{23}$ and $R_{24}$ are each independently a hydrogen or a ($C_1$–$C_7$)alkyl;

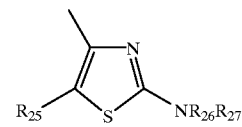

in which $R_{25}$ is a hydrogen or a ($C_1$–$C_7$)alkyl and $R_{26}$ and $R_{27}$ are each independently a hydrogen or a ($C_1$–$C_7$)alkyl; $R_{27}$ can also be a formyl or a ($C_1$–$C_7$)alkylcarbonyl; and

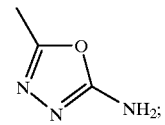

and their salts, especially pharmaceutically acceptable salts.

Among these compounds, those of the formula (I'a)

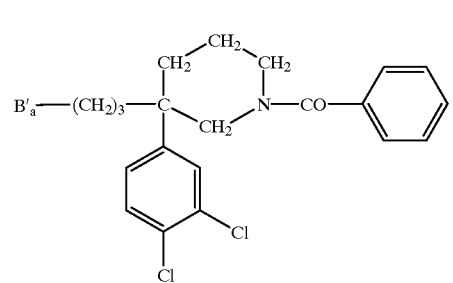

in which:

$B'_a$ is a group $B'_{1a}$ of the formula

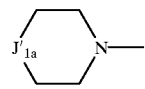

in which $J'_{1a}$ is a group

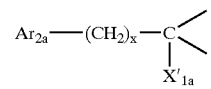

in which:
x is zero;
Ar$_{2a}$ is as defined for a compound of formula (Ia); and
X'$_{1a}$ is a group selected from:
- —O—CH$_2$—CH$_2$—OR$_6$ in which R$_6$ is a hydrogen; a (C$_1$–C$_7$)alkyl; a formyl; or a (C$_1$–C$_7$)alkylcarbonyl;
- —NR$_{12}$COR$_{13}$ in which R$_{12}$ is a hydrogen or a (C$_1$–C$_7$)alkyl and R$_{13}$ is a vinyl, a furyl, a thienyl, a pyrrolyl or an imidazolyl;
- —NR$_{14}$COCOR$_{15}$ in which R$_{14}$ is a hydrogen or a (C$_1$–C$_7$)alkyl and R$_{15}$ is a (C$_1$–C$_4$)alkoxy;
- —(CH$_2$)$_p$—NR$_{14}$C(=W$_1$)R$_{16}$ in which p is one, W$_1$ is an oxygen atom, R$_{14}$ is a hydrogen or a (C$_1$–C$_7$)alkyl and R$_{16}$ is a vinyl, a furyl, a thienyl, a pyrrolyl or an imidazolyl;
- —(CH$_2$)$_m$—NR$_{14}$C(=W$_1$)NR$_{19}$R$_{20}$ in which m is zero, W$_1$ is an oxygen atom, R$_{14}$ is a hydrogen or a (C$_1$–C$_7$)alkyl, R$_{19}$ is a hydrogen or a (C$_1$–C$_7$)alkyl and R$_{20}$ is a (C$_1$–C$_7$)alkyl substituted by a hydroxyl, a (C$_1$–C$_3$)alkoxy, a phenyl, a carboxyl, a (C$_1$–C$_3$) alkoxycarbonyl or a carbamoyl which is unsubstituted or substituted by one or two (C$_1$–C$_7$)alkyls;
- —CO—NR$_{22}$—NR$_{23}$R$_{24}$ in which R$_{22}$ is a hydrogen or a (C$_1$–C$_7$)alkyl and R$_{23}$ and R$_{24}$ are each independently a hydrogen or a (C$_1$–C$_7$)alkyl;

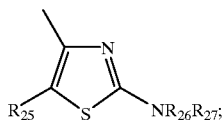

in which R$_{25}$ is a hydrogen or a (C$_1$–C$_7$)alkyl and R$_{26}$ and R$_{27}$ are each independently a hydrogen or a (C$_1$–C$_7$)alkyl; R$_{27}$ can also be a formyl or a (C$_1$–C$_7$)alkylcarbonyl; and

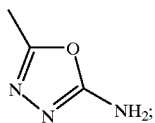

and their salts, especially pharmaceutically acceptable salts, are particularly preferred.

Among these compounds, those of the formula (I"a)

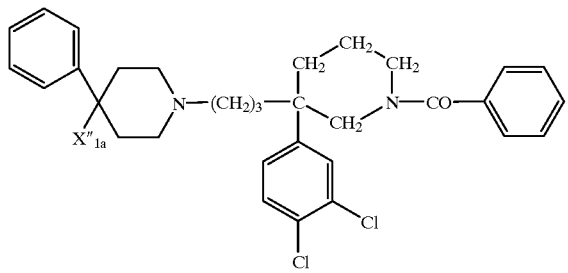

in which:
X"$_{1a}$ is a group selected from:
- —O—CH$_2$—CH$_2$—OR$_6$ in which R$_6$ is a hydrogen; a (C$_1$–C$_7$)alkyl; a formyl; or a (C$_1$–C$_7$)alkylcarbonyl, preferably a hydrogen or an acetyl;
- —NR$_{12}$COR$_{13}$ in which R$_{12}$ is a hydrogen or a (C$_1$–C$_7$) alkyl, preferably a hydrogen, and R$_{13}$ is a vinyl, a furyl, a thienyl, a pyrrolyl or an imidazolyl, preferably a furyl or a thienyl;
- —NR$_{14}$COCOR$_{15}$ in which R$_{14}$ is a hydrogen or a (C$_1$–C$_7$)alkyl, preferably a hydrogen, and R$_{15}$ is a (C$_1$–C$_4$)alkoxy, preferably an ethoxy; and

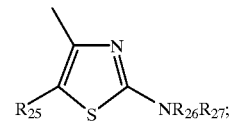

in which R$_{25}$ is a hydrogen or a (C$_1$–C$_7$)alkyl, preferably a hydrogen, and R$_{26}$ and R$_{27}$ are each independently a hydrogen or a (C$_1$–C$_7$)alkyl; R$_{27}$ can also be a formyl or a (C$_1$–C$_7$)alkylcarbonyl; R$_{26}$ and R$_{27}$ are preferably a hydrogen; and

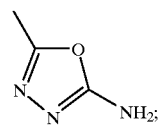

and their salts, especially pharmaceutically acceptable salts, are more particularly preferred.

Another group of preferred compounds of the invention are those of the formula (Ib)

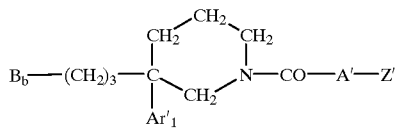

in which:
Ar'$_1$ is a phenyl which is unsubstituted or monosubstituted or polysubstituted by a substituent selected from a halogen atom, a hydroxyl, a (C$_1$–C$_4$)alkoxy, a (C$_1$–C$_4$)-alkyl, a trifluoromethyl and a methylenedioxy, said substituents being identical or different;
A' is a direct bond or a group —CH$_2$—;
Z' is as defined above; and
B$_b$ is a group B$_{1b}$ of the formula

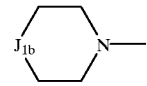

in which J$_{1b}$ is a group

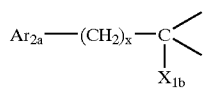

in which:
x is one;
Ar$_{2a}$ is a phenyl which is unsubstituted or monosubstituted or polysubstituted by a substituent selected from a halogen atom, a hydroxyl, a (C$_1$–C$_4$)alkoxy, a (C$_1$–C$_4$)alkyl, a trifluoromethyl and a methylenedioxy, said substituents being identical or different; and $X_{1b}$ is a group selected from:
hydrogen;
$(C_1-C_7)$alkyl;
formyl;
$(C_1-C_7)$alkylcarbonyl;
—$(CH_2)_m$—$OR_4$;
—$(CH_2)_m$—$OCOR_5$;
—$(CH_2)_m$—OCONH—$(C_1-C_7)$alkyl;
—O—$CH_2CH_2$—$OR_6$;
—$(CH_2)_n$—$SR_7$;
—$CH_2$—$S(O)_j$—$(C_1-C_7)$alkyl;
—$NR_8R_9$;
—$(CH_2)_p$—$NR_{10}R_{11}$;
—$NR_{12}COR_{13}$;
—$NR_{14}COCOR_{15}$;
—$(CH_2)_p$—$NR_{14}C(=W_1)R_{16}$;
—$(CH_2)_m$—$NR_{14}COOR_{17}$;
—$(CH_2)_m$—$NR_{14}SO_2R_{18}$;
—$(CH_2)_m$—$NR_{14}C(=W_1)NR_{19}R_{20}$;
—$(CH_2)_n$—$COOR_{21}$;
—$(CH_2)_n$—$C(=W_1)NR_{19}R_{20}$;
—CO—$NR_{22}$—$NR_{23}R_{24}$;
—CN;

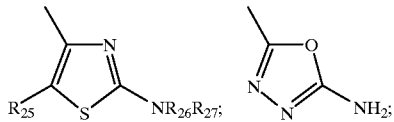

or $X_{1b}$ forms a double bond between the carbon atom to which it is bonded and the adjacent carbon atom of the piperidine ring,
in which groups:
m is zero, one or two;
n is zero or one;
p is one or two;
j is one or two;
$W_1$ is an oxygen atom or a sulfur atom;
$R_4$ is a hydrogen or a $(C_1-C_7)$alkyl;
$R_5$ is a hydrogen; a $(C_1-C_7)$alkyl; a $(C_3-C_7)$cycloalkyl which is unsubstituted or substituted by one or more methyls; a phenyl; or a pyridyl;
$R_6$ is a hydrogen; a $(C_1-C_7)$alkyl; a formyl; or a $(C_1-C_7)$alkylcarbonyl;
$R_7$ is a hydrogen or a $(C_1-C_7)$alkyl;
$R_8$ and $R_9$ are each independently a hydrogen or a $(C_1-C_7)$alkyl; $R_9$ can also be a $(C_3-C_7)$cycloalkylmethyl, a benzyl or a phenyl;
or $R_8$ and $R_9$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$alkyl;
$R_{10}$ and $R_{11}$ are each independently a hydrogen or a $(C_1-C_7)$alkyl; $R_{11}$ can also be a $(C_3-C_7)$cycloalkylmethyl or a benzyl;
$R_{12}$ is a hydrogen or a $(C_1-C_7)$alkyl;
$R_{13}$ is a hydrogen; a $(C_1-C_7)$alkyl; a $(C_3-C_7)$cycloalkyl which is unsubstituted or substituted by one or more methyls; a phenyl; a benzyl; a vinyl; a pyridyl; a furyl; a thienyl; a pyrrolyl; or an imidazolyl;
or $R_{12}$ and $R_{13}$ together are a group —$(CH_2)_u$— in which u is three or four;

$R_{14}$ is a hydrogen or a $(C_1-C_7)$alkyl;
$R_{15}$ is a $(C_1-C_4)$alkoxy;
$R_{16}$ is a hydrogen; a $(C_1-C_7)$alkyl; a $(C_3-C_7)$cycloalkyl which is unsubstituted or substituted by one or more methyls; a phenyl; a benzyl; a vinyl; a pyridyl; a furyl; a thienyl; a pyrrolyl; or an imidazolyl;
$R_{17}$ is a $(C_1-C_7)$alkyl or a phenyl;
$R_{18}$ is a $(C_1-C_7)$alkyl; an amino which is free or substituted by one or two $(C_1-C_7)$alkyls; or a phenyl which is unsubstituted or monosubstituted or polysubstituted by a substituent selected from a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$alkylcarbonyloxy, a cyano, a nitro and an amino which is free or substituted by one or two $(C_1-C_7)$alkyls, said substituents being identical or different;
$R_{19}$ and $R_{20}$ are each independently a hydrogen or a $(C_1-C_7)$alkyl; $R_{20}$ can also be a $(C_3-C_7)$cycloalkyl; a $(C_3-C_7)$cycloalkylmethyl; a hydroxyl; a $(C_1-C_4)$alkoxy; a benzyl; a phenyl; or a $(C_1-C_7)$alkyl substituted by a hydroxyl, a $(C_1-C_3)$alkoxy, a phenyl, a carboxyl, a $(C_1-C_3)$alkoxycarbonyl or a carbamoyl which is unsubstituted or substituted by one or two $(C_1-C_7)$alkyls;
or $R_{19}$ and $R_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$alkyl;
$R_{21}$ is a hydrogen or a $(C_1-C_7)$alkyl;
$R_{22}$ is a hydrogen or a $(C_1-C_7)$alkyl;
$R_{23}$ and $R_{24}$ are each independently a hydrogen or a $(C_1-C_7)$alkyl;
$R_{25}$ is a hydrogen or a $(C_1-C_7)$alkyl; and
$R_{26}$ and $R_{27}$ are each independently a hydrogen or a $(C_1-C_7)$alkyl; $R_{27}$ can also be a formyl or a $(C_1-C_7)$alkylcarbonyl, with the proviso that:

when $Ar'_1$ is the 3,4-dichlorophenyl group and —A'—Z' is the 3-methoxybenzyl group, $B_b$ is the group $B_{1b}$ of the formula

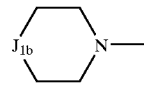

in which $J_{1b}$ is the group

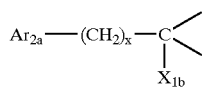

in which x is one, $Ar_{2a}$ is a phenyl group and $X_{1b}$ is other than hydrogen, and their salts, especially pharmaceutically acceptable salts.

Among these compounds, those of the formula

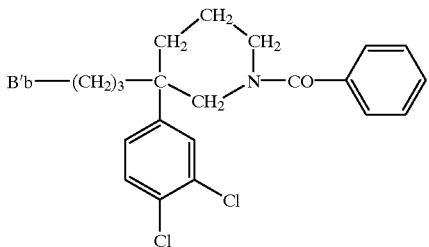

(I'b)

in which:

B'$_b$ is a group B'$_{1b}$ of the formula

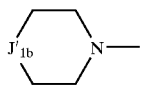

in which J'$_{1b}$ is a group

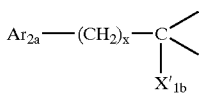

in which:

x is one;

Ar$_{2a}$ is as defined for a compound of formula (Ib); and

X'$_{1b}$ is as group s elected from:
- —(C$_1$–C$_7$)alkyl;
- —(CH$_2$)$_m$—OR$_4$ in which m is one or two and R$_4$ is a hydrogen or a (C$_1$–C$_7$)alkyl;
- —(CH$_2$)$_m$—OCOR$_5$ in which:
  - m is zero and R$_5$ is a (C$_3$–C$_7$)cycloalkyl which is unsubstituted or substituted by one or more methyls; a phenyl; or a pyridyl; or
  - m is one or two and R$_5$ is a hydrogen; a (C$_1$–C$_7$)alkyl; a (C$_3$–C$_7$)cycloalkyl which is unsubstituted or substituted by one or more methyls; a phenyl; or a pyridyl;
- —(CH$_2$)$_m$—OCONH—(C$_1$–C$_7$)alkyl in which m is zero, one or two;
- —O—CH$_2$—CH$_2$—OR$_6$ in which R$_6$ is a hydrogen; a (C$_1$–C$_7$)alkyl; a formyl; or a (C$_1$–C$_7$)alkylcarbonyl;
- —(CH$_2$)$_n$—SR$_7$ in which n is zero or one and R$_7$ is a hydrogen or a (C$_1$–C$_7$)alkyl;
- —CH$_2$—S(O)$_j$—(C$_1$–C$_7$)alkyl in which j is one or two;
- —NR$_8$R$_9$ in which R$_8$ is a hydrogen or a (C$_1$–C$_7$)alkyl and R$_9$ is a (C$_3$–C$_7$)cycloalkylmethyl or a benzyl; or R$_8$ and R$_9$, together with the nitrogen atom to which they are bonded, form a heterocycle selected from azetidine, thiomorpholine, perhydroazepine and piperazine which is unsubstituted or substituted in the 4-position by a (C$_1$–C$_4$)alkyl;
- —(CH$_2$)$_p$—NR$_{10}$R$_{11}$ in which p is one or two and R$_{10}$ and R$_{11}$ are each independently a hydrogen or a (C$_1$–C$_7$)alkyl; R$_{11}$ can also be a (C$_3$–C$_7$)cycloalkylmethyl or a benzyl;
- —NR$_{12}$COR$_{13}$ in which R$_{12}$ is a hydrogen or a (C$_1$–C$_7$)alkyl and R$_{13}$ is a (C$_3$–C$_7$)-cycloalkyl which is unsubstituted or substituted by one or more methyls; a phenyl; a benzyl; a vinyl; a pyridyl; a furyl; a thienyl; a pyrrolyl; or an imidazolyl; or R$_{12}$ and R$_{13}$ together are a group —(CH$_2$)$_u$— in which u is three or four;
- —NR$_{14}$COCOR$_{15}$ in which R$_{14}$ is a hydrogen or a (C$_1$–C$_7$)alkyl and R$_{15}$ is a (C$_1$–C$_4$)alkoxy;
- —(CH$_2$)$_p$—NR$_{14}$C(=W$_1$)R$_{16}$ in which p is one or two, W$_1$ is an oxygen atom or a sulfur atom, R$_{14}$ is a hydrogen or a (C$_1$–C$_7$)alkyl and R$_{16}$ is a hydrogen; a (C$_1$–C$_7$)alkyl; a (C$_3$–C$_7$)cycloalkyl which is unsubstituted or substituted by one or more methyls; a phenyl; a benzyl; a vinyl; a pyridyl; a furyl; a thienyl; a pyrrolyl; or an imidazolyl;
- —(CH$_2$)$_m$—NR$_{14}$COOR$_{17}$ in which m is zero, one or two, R$_{14}$ is a hydrogen or a (C$_1$–C$_7$)alkyl and R$_{17}$ is a (C$_1$–C$_7$)alkyl or a phenyl;
- —(CH$_2$)$_m$—NR$_{14}$SO$_2$R$_{18}$ in which m is zero, one or two, R$_{14}$ is a hydrogen or a (C$_1$–C$_7$)alkyl and R$_{18}$ is a (C$_1$–C$_7$)alkyl; an amino which is free or substituted by one or two (C$_1$–C$_7$)alkyls; or a phenyl which is unsubstituted or monosubstituted or polysubstituted by a substituent selected from a halogen atom, a (C$_1$–C$_7$)alkyl, a trifluoromethyl, a hydroxyl, a (C$_1$–C$_7$)alkoxy, a carboxyl, a (C$_1$–C$_7$)alkoxycarbonyl, a (C$_1$–C$_7$)alkylcarbonyloxy, a cyano, a nitro and an amino which is free or substituted by one or two (C$_1$–C$_7$)alkyls, said substituents being identical or different;
- —(CH$_2$)$_m$—NR$_{14}$C(=W$_1$)NR$_{19}$R$_{20}$ in which m is zero, one or two, W$_1$ is an oxygen atom or a sulfur atom, R$_{14}$ is a hydrogen or a (C$_1$–C$_7$)alkyl and R$_{19}$ and R$_{20}$ are each independently a hydrogen or a (C$_1$–C$_7$)alkyl; R$_{20}$ can also be a (C$_3$–C$_7$)-cycloalkyl; a (C$_3$–C$_7$)cycloalkylmethyl; a hydroxyl; a (C$_1$–C$_4$)alkoxy; a benzyl; a phenyl; or a (C$_1$–C$_7$)alkyl substituted by a hydroxyl, a (C$_1$–C$_3$)alkoxy, a phenyl, a carboxyl, a (C$_1$–C$_3$)alkoxycarbonyl or a carbamoyl which is unsubstituted or substituted by one or two (C$_1$–C$_7$)alkyls; or R$_{19}$ and R$_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a (C$_1$–C$_4$)alkyl;
- —(CH$_2$)$_n$—COOR$_{21}$ in which n is one and R$_{21}$ is a hydrogen or a (C$_1$–C$_7$)alkyl;
- —(CH$_2$)$_n$—C(=W$_1$)NR$_{19}$R$_{20}$ in which n is zero or one, W$_1$ is an oxygen atom or a sulfur atom and R$_{19}$ and R$_{20}$ are each independently a hydrogen or a (C$_1$–C$_7$)-alkyl; R$_{20}$ can also be a (C$_3$–C$_7$)cycloalkyl; a (C$_3$–C$_7$)cycloalkylmethyl; a hydroxyl; a (C$_1$–C$_4$)alkoxy; a benzyl; a phenyl; or a (C$_1$–C$_7$)alkyl substituted by a hydroxyl, a (C$_1$–C$_3$)alkoxy, a phenyl, a carboxyl, a (C$_1$–C$_3$)alkoxycarbonyl or a carbamoyl which is unsubstituted or substituted by one or two (C$_1$–C$_7$)alkyls; or R$_{19}$ and R$_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a (C$_1$–C$_4$)alkyl;
- —CO—NR$_{22}$—NR$_{23}$R$_{24}$ in which R$_{22}$ is a hydrogen or a (C$_1$–C$_7$)alkyl and R$_{23}$ and R$_{24}$ are each independently a hydrogen or a (C$_1$–C$_7$)alkyl;

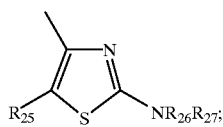

in which $R_{25}$ is a hydrogen or a $(C_1-C_7)$alkyl and $R_{26}$ and $R_{27}$ are each independently a hydrogen or a $(C_1-C_7)$alkyl; $R_{27}$ can also be a formyl or a $(C_1-C_7)$alkylcarbonyl; and

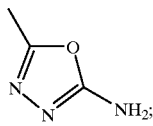

and their salts, especially pharmaceutically acceptable salts, are particularly preferred.

Among these compounds, those of the formula

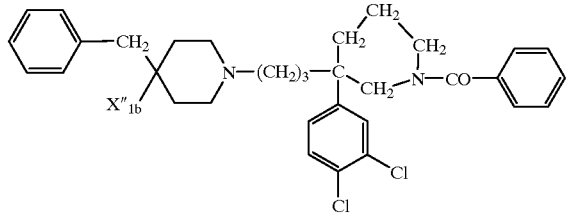

(I″b)

in which:

$X''_{1b}$ is a group selected from:
—$(CH_2)_p$—$NR_{10}R_{11}$ in which p is one and $R_{10}$ and $R_{11}$ are each a hydrogen;
—$(CH_2)_p$—$NR_{14}C(=W_1)R_{16}$ in which p is one, $W_1$ is an oxygen atom, $R_{14}$ is a hydrogen or a $(C_1-C_7)$alkyl and $R_{16}$ is a $(C_1-C_7)$alkyl, preferably an ethyl;
—$(CH_2)_m$—$NR_{14}COOR_{17}$ in which m is zero, $R_{14}$ is a hydrogen and $R_{17}$ is a $(C_1-C_7)$alkyl, preferably an ethyl; and
—$(CH_2)_m$—$C(=W_1)NR_{19}R_{20}$ in which n is zero, $W_1$ is an oxygen atom and $R_{19}$ and $R_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$alkyl, preferably pyrrolidine, and their salts, especially pharmaceutically acceptable salts, are more particularly preferred.

Another group of preferred compounds of the invention are those of the formula

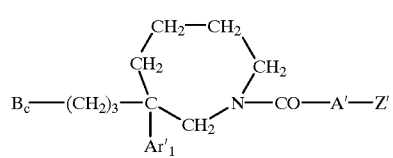

(Ic)

in which:

$Ar'_1$ is a phenyl which is unsubstituted or monosubstituted or polysubstituted by a substituent selected from a halogen atom, a hydroxyl, a $(C_1-C_4)$alkoxy, a $(C_1-C_4)$alkyl, a trifluoromethyl and a methylenedioxy, said substituents being identical or different;

A' is a direct bond or a group —$CH_2$—;

Z' is as defined above; and $B_c$ is a group $B_{1c}$ of the formula

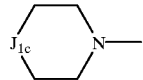

in which $J_{1c}$ is a group

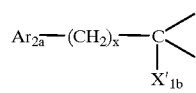

in which:

x is zero or one;

$Ar_{2a}$ is a phenyl which is unsubstituted or monosubstituted or polysubstituted by a substituent selected from a halogen atom, a hydroxyl, a $(C_1-C_4)$alkoxy, a $(C_1-C_4)$alkyl, a trifluoromethyl and a methylenedioxy, said substituents being identical or different; and $X_{1b}$ is as defined above for a compound of formula $(I_b)$, and their salts, especially pharmaceutically acceptable salts.

Among these compounds, those of the formula

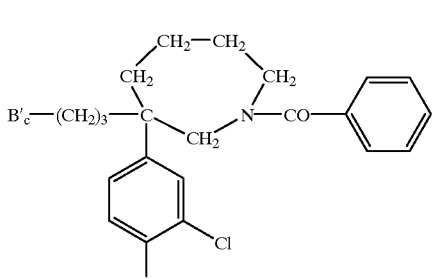

(I'c)

in which:

$B'_c$ is a group $B'_{1c}$ of the formula

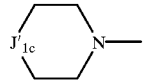

in which $J'_{1c}$ is a group

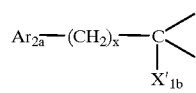

in which:

x is zero or one;

$Ar_{2a}$ is as defined for a compound of formula (Ic); and $X'_{1b}$ is a group selected from:
$(C_1-C_7)$alkyl;
—$(CH_2)_m$—$OR_4$ in which m is one or two and $R_4$ is a hydrogen or a $(C_1-C_7)$alkyl;
—$(CH_2)_m$—$OCOR_5$ in which m is zero and $R_5$ is a $(C_3-C_7)$cycloalkyl which is unsubstituted or substituted by one or more methyls; a phenyl; or a pyridyl; and m is one or two and $R_5$ is a hydrogen; a $(C_1-C_7)$alkyl; a $(C_3-C_7)$cycloalkyl which is unsubstituted or substituted by one or more methyls; a phenyl; or a pyridyl;

—$(CH_2)_m$—OCONH—$(C_1-C_7)$alkyl in which m is zero, one or two;

—O—$CH_2$—$CH_2$—$OR_6$ in which $R_6$ is a hydrogen; a $(C_1-C_7)$alkyl; a formyl; or a $(C_1-C_7)$alkylcarbonyl;

—$(CH_2)_n$—$SR_7$ in which n is zero or one and $R_7$ is a hydrogen or a $(C_1-C_7)$alkyl;

—$CH_2$—$S(O)_j$—$(C_1-C_7)$alkyl in which j is one or two;

—$NR_8R_9$ in which $R_8$ is a hydrogen or a $(C_1-C_7)$alkyl and $R_9$ is a $(C_3-C_7)$cyclo-alkylmethyl or a benzyl; or $R_8$ and $R_9$, together with the nitrogen atom to which they are bonded, form a heterocycle selected from azetidine, thiomorpholine, perhydroazepine and piperazine which is unsubstituted or substituted in the 4-position by a $(C_1-C_4)$alkyl;

—$(CH_2)_p$—$NR_{10}R_{11}$ in which p is one or two, $R_{10}$ is a hydrogen or a $(C_1-C_7)$alkyl and $R_{11}$ is a hydrogen, a $(C_1-C_7)$alkyl, a $(C_3-C_7)$cycloalkylmethyl or a benzyl;

—$NR_{12}COR_{13}$ in which $R_{12}$ is a hydrogen or a $(C_1-C_7)$alkyl and $R_{13}$ is a $(C_3-C_7)$-cycloalkyl which is unsubstituted or substituted by one or more methyls; a phenyl; a benzyl; a vinyl; a pyridyl; a furyl; a thienyl; a pyrrolyl; or an imidazolyl; or $R_{12}$ and $R_{13}$ together form a group —$(CH_2)_u$— in which u is three or four;

—$NR_{14}COCOR_{15}$ in which $R_{14}$ is a hydrogen or a $(C_1-C_7)$alkyl and $R_{15}$ is a $(C_1-C_4)$alkoxy;

—$(CH_2)_p$—$NR_{14}C(=W_1)R_{16}$ in which p is one or two, $W_1$ is an oxygen atom or a sulfur atom, $R_{14}$ is a hydrogen or a $(C_1-C_7)$alkyl and $R_{16}$ is a hydrogen; a $(C_1-C_7)$alkyl; a $(C_3-C_7)$cycloalkyl which is unsubstituted or substituted by one or more methyls; a phenyl; a benzyl; a vinyl; a pyridyl; a furyl; a thienyl; a pyrrolyl; or an imidazolyl;

—$(CH_2)_m$—$NR_{14}COOR_{17}$ in which m is zero, one or two, $R_{14}$ is a hydrogen or a $(C_1-C_7)$alkyl and $R_{17}$ is a $(C_1-C_7)$alkyl or a phenyl;

—$(CH_2)_m$—$NR_{14}SO_2R_{18}$ in which m is zero, one or two, $R_{14}$ is a hydrogen or a $(C_1-C_7)$alkyl and $R_{18}$ is a $(C_1-C_7)$alkyl; an amino which is free or substituted by one or two $(C_1-C_7)$alkyls; or a phenyl which is unsubstituted or monosubstituted or polysubstituted by a substituent selected from a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$alkylcarbonyloxy, a cyano, a nitro and an amino which is free or substituted by one or two $(C_1-C_7)$alkyls, said substituents being identical or different;

—$(CH_2)_m$—$NR_{14}C(=W_1)NR_{19}R_{20}$ in which m is zero, one or two, $W_1$ is an oxygen atom or a sulfur atom, $R_{14}$ is a hydrogen or a $(C_1-C_7)$alkyl and $R_{19}$ and $R_{20}$ are each independently a hydrogen or a $(C_1-C_7)$alkyl; $R_{20}$ can also be a $(C_3-C_7)$-cycloalkyl; a $(C_3-C_7)$cycloalkylmethyl; a hydroxyl; a $(C_1-C_4)$ alkoxy; a benzyl; a phenyl; or a $(C_1-C_7)$alkyl substituted by a hydroxyl, a $(C_1-C_3)$alkoxy, a phenyl, a carboxyl, a $(C_1-C_3)$alkoxycarbonyl or a carbamoyl which is unsubstituted or substituted by one or two $(C_1-C_7)$alkyls; or $R_{19}$ and $R_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$alkyl;

—$(CH_2)_n$—$COOR_2$, in which n is one and $R_{21}$ is a hydrogen or a $(C_1-C_7)$alkyl;

—$(CH_2)_n$—$C(=W_1)NR_{19}R_{20}$ in which n is zero or one, $W_1$ is an oxygen atom or a sulfur atom and $R_{19}$ and $R_{20}$ are each independently a hydrogen or a $(C_1-C_7)$-alkyl; $R_{20}$ can also be a $(C_3-C_7)$cycloalkyl; a $(C_3-C_7)$cycloalkylmethyl; a hydroxyl; a $(C_1-C_4)$ alkoxy; a benzyl; a phenyl; or a $(C_1-C_7)$alkyl substituted by a hydroxyl, a $(C_1-C_3)$alkoxy, a phenyl, a carboxyl, a $(C_1-C_3)$alkoxycarbonyl or a carbamoyl which is unsubstituted or substituted by one or two $(C_1-C_7)$alkyls; or $R_{19}$ and $R_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$alkyl;

—CO—$NR_{22}$—$NR_{23}R_{24}$ in which $R_{22}$ is a hydrogen or a $(C_1-C_7)$alkyl and $R_{23}$ and $R_{24}$ are each independently a hydrogen or a $(C_1-C_7)$alkyl;

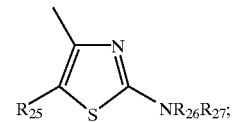

in which $R_{25}$ is a hydrogen or a $(C_1-C_7)$alkyl and $R_{26}$ and $R_{27}$ are each independently a hydrogen or a $(C_1-C_7)$alkyl; $R_{27}$ can also be a formyl or a $(C_1-C_7)$alkylcarbonyl; and

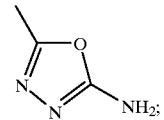

and their salts, especially pharmaceutically acceptable salts, are particularly preferred.

The following compounds:

1-benzoyl-3-(3,4-dichlorophenyl)-3-[3-[4-(pyrrolidin-1-ylcarbonyl)-piperid-1-yl]propyl]piperidine;

1-benzoyl-3-(3,4-dichlorophenyl)-3-[3-(4-piperidinopiperid-1-yl)-propyl]piperidine;

1-benzoyl-3-(3,4-dichlorophenyl)-3-[3-(4-carbamoyl-4-piperidinopiperid-1-yl)propyl]piperidine;

3-[3-[4-(acryloyl-N-methylamino)-4-phenylpiperid-1-yl]propyl-1-benzoyl-3-(3,4-dichlorophenyl)piperidine;

3-[3-[4-(2-aminothiazol-4-yl)-4-phenylpiperid-1-yl]propyl]-1-benzoyl-3-(3,4-dichlorophenyl)piperidine;

3-[3-(4-acetyl-4-benzylpiperid-1-yl)propyl]-1-benzoyl-3-(3,4-dichloro-phenyl)piperidine;

3-[3-[4-(acetylamino)-4-benzylpiperid-1-yl]propyl]-1-benzoyl-3-(3,4-dichlorophenyl)piperidine;

1-benzoyl-3-[3-[4-benzyl-4-(propionylaminomethyl)piperid-1-yl]propyl]-3-(3,4-dichlorophenyl)piperidine;

1-benzoyl-3-[3-[4-benzyl-4-(ethoxycarbonylamino)piperid-1-yl]propyl]-3-(3,4-dichlorophenyl)piperidine;

1-benzoyl-3-[3-[4-benzyl-4-(pyrrolidin-1-ylcarbonyl)piperid-1-yl]propyl]-3-(3,4-dichlorophenyl)piperidine;

1-benzoyl-3-(3,4-dichlorophenyl)-3-[3-[4-(dimethylaminocarbonyl)-4-phenylpiperid-1-yl]propyl]perhydroazepine;

1-benzoyl-3-(3,4-dichlorophenyl)-3-[3-[4-(2-hydroxyethoxy)-4-phenyl-piperid-1-yl]propyl]piperidine;

3-[3-[4-(2-acetoxyethoxy)-4-phenylpiperid-1-yl]propyl]-1-benzoyl-3-(3,4-dichlorophenyl)piperidine;

1-benzoyl-3-(3,4-dichlorophenyl)-3-[3-[4-(2-furoylamino)-4-phenylpiperid-1-yl]propyl]piperidine;

1-benzoyl-3-(3,4-dichlorophenyl)-3-[3-[4-(2-thenoylamino)-4-phenyl-piperid-1-yl]propyl]piperidine;

3-(3,4-dichlorophenyl)-1-isonicotinoyl-3-[3-[4-phenyl-4-(pyrrolidin-1-ylcarbonyl)piperid-1-yl]propyl]piperidine;

1-benzoyl-3-(3,4-dichlorophenyl)-3-[3-spiro(indoline-3,4'-piperid-1'-yl)propyl]piperidine;

1-benzoyl-3-(3,4-dichlorophenyl)-3-[3-[1-acetylspiro(indoline-3,4'-piperid-1-yl)]propyl]piperidine;

3-(3,4-dichlorophenyl)-3-[3-[4-phenyl-4-(pyrrolidin-1-ylcarbonyl)piperid-1-yl]propyl]-1-(2-thenoyl)piperidine;

3-(3,4-dichlorophenyl)-3-[3-[4-phenyl-4-(pyrrolidin-1-ylcarbonyl)piperid-1-yl]propyl]-1-(3-thenoyl)piperidine;

3-(3,4-dichlorophenyl)-1-(2-furoyl)-3-[3-[4-phenyl-4-(pyrrolidin-1-ylcarbonyl)piperid-1-yl]propyl]piperidine;

3-(3,4-dichlorophenyl)-1-(3-furoyl)-3-[3-[4-phenyl-4-(pyrrolidin-1-ylcarbonyl)piperid-1-yl]propyl]piperidine;

3-[3-[4-(2-amino-1,3,4-oxadiazol-5-yl)-4-phenylpiperid-1-yl]propyl]-1-benzoyl-3-(3,4-dichlorophenyl)piperidine;

1-benzoyl-3-(3,4-dichlorophenyl)-3-[3-[4-(ethoxalylamino)-4-phenyl-piperid-1-yl]propyl]piperidine;

1-benzoyl-3-(3,4-dichlorophenyl)-3-[3-(4-carbamoyl-4-morpholinopiperid-1-yl)propyl]piperidine;

1-benzoyl-3-(3,4-dichlorophenyl)-3-[3-[1-(methoxycarbonyl)spiro(indoline-3,4'-piperid-1'-yl)]propyl]piperidine;

1-benzoyl-3-(3,4-dichlorophenyl)-3-[3-[1-(N,N-dimethylcarbamoyl)spiro(indoline-3,4'-piperid-1'-yl)]propyl]piperidine; and 1-benzoyl-3-(3,4-dichlorophenyl)-3-[3-[1-(methanesulfonyl)spiro(indoline-3,4'-piperid-1'-yl)]propyl]piperidine, in the form of racemates or one of their (+) or (−) enantiomers,
and their salts, especially pharmaceutically acceptable salts, are very particularly preferred according to the present invention.

The invention further relates, where they exist, to the solvates of the compounds of the invention and their salts, namely the compounds of formulae (I), (I'), (I''), (I''a), (Ia), (I'a), (I''a), (Ib), (I'b), (I''b), (Ic) and (I'c) and their salts.

The compounds according to the invention are obtained by known methods, particularly those described in patent applications EP-A-474 561 and EP-A-512 901.

One of the methods suitable for obtaining the compounds of formula (I) and their salts is described below.

According to this method:

1) a compound of the formula

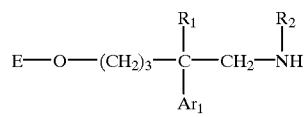
(II)

in which $Ar_1$, $R_1$ and $R_2$ are as defined for a compound of formula (I) and E is hydrogen or an O-protecting group, is treated:

either with a halogenated derivative of the formula

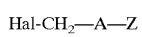 (III)

in which Hal is a halogen atom, preferably bromine, and A and Z are as defined for a compound of formula (I), when it is desired to prepare a compound of formula (I) in which T is a group —CH$_2$—;

or with a functional derivative of an acid of the formula

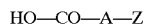 (IIIa)

in which A and Z are as defined above, when it is desired to prepare a compound of formula (I) in which T is a group —CO—;

or with a chloroformate of the formula

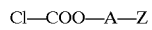 (IIIb)

in which A and Z are as defined above, when it is desired to prepare a compound of formula (I) in which T is group —COO—;

or with an isocyanate of the formula

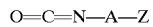 (IIIc)

in which A and Z are as defined above, when it is desired to prepare a compound of formula (I) in which T is a group —CO—NR$_3$— in which R$_3$ is hydrogen;

or with a carbamoyl chloride of the formula

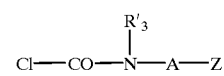 (IIId)

in which A and Z are as defined above and R'$_3$ is a (C$_1$–C$_4$)alkyl, when it is desired to prepare a compound of formula (I) in which T is —CONR$_3$— in which R$_3$ is a (C$_1$–C$_4$)alkyl;

or with a sulfonyl chloride of the formula

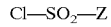 (IIIe)

in which Z is as defined above, when it is desired to prepare a compound of formula (I) in which —T—A— is a group —SO$_2$—, to give a compound of the formula

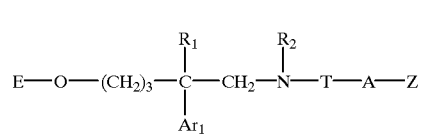
(IV)

2) the O-protecting group, if present, is removed from the compound of formula (IV), by reaction with an acid or a base, to give the alcohol of the formula

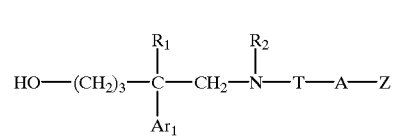
(V)

3) the alcohol (V) is treated with a compound of the formula

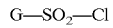 (VI)

in which G is a methyl, phenyl, tolyl or trifluoromethyl group, to give a compound of the formula

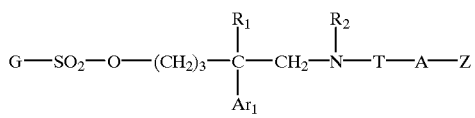 (VII)

4) the compound (VII) is reacted:
either with a cyclic secondary amine of the formula

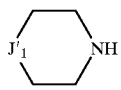 (VIIIa)

in which J'₁ is:
* either a group

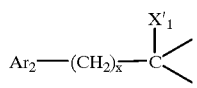

in which Ar₂ and x are as defined for (I) and X'₁ is either X₁ as defined for (I), or a precursor of X₁, it being understood that when X'₁ contains a hydroxyl group or an amino group, these groups can be protected;
* either a group

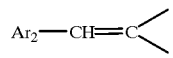

in which Ar₂ is as defined for (I);
* or a group

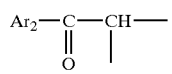

in which Ar₂ is as defined for (I);
* or a group

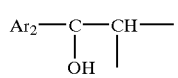

in which Ar₂ is as defined for (I);
* or a group

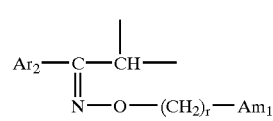

in which Ar₂, Am₁ and r are as defined for (I);
or a group

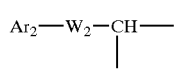

in which Ar₂ and W₂ are as defined for (I);

or with a cyclic secondary amine of the formula

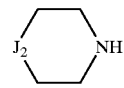 (VIIIb)

in which J₂ is as defined above for (I);

or with a cyclic secondary amine of the formula

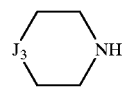 (VIIIc)

in which J₃ is as defined above for (I);

or with a cyclic secondary amine of the formula

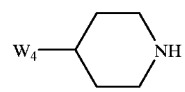 (VIIId)

in which W₄ is as defined above for (I);

or with a cyclic secondary amine of the formula

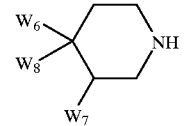 (VIIIe)

in which W₆, W₇ and W₈ are as defined above for (I);
or with a cyclic secondary amine of the formula (VIIIf)

in which J₄ is as defined above for (I);
or with a compound of the formula

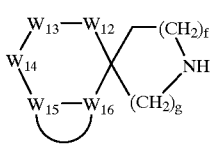 (VIIIg)

in which f, g, W₁₂, W₁₃, W₁₄, W₁₅ and W₁₆ are as defined above for (I);

or with a cyclic secondary amine of the formula

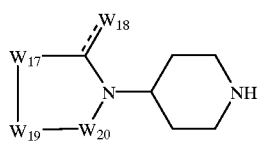
(VIIIh)

in which $W_{17}$, $W_{18}$, $W_{19}$ and $W_{20}$ are as defined above for (I);

or with a cyclic secondary amine of the formula

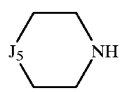
(VIIIi)

in which $J_5$ is as defined above for (I);

or a cyclic secondary amine of the formula

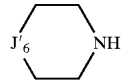
(VIIIj)

in which $J'_6$ is a group

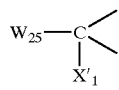

in which $W_{25}$ is as defined above for (I) and $X'_1$ is $X_1$ as defined for (I), or a precursor of $X_1$, it being understood that when $X'_1$ contains a hydroxyl group or an amino group, these groups can be protected; and 5) after deprotection of the hydroxyl groups or amino groups, if appropriate, or conversion of $X'_1$ to $X_1$, if appropriate, the resulting product is optionally converted to one of its salts with a mineral or organic acid.

In one variant of the method:

1') the nitrogen atom of the compound of formula (II) is protected to give a compound of the formula

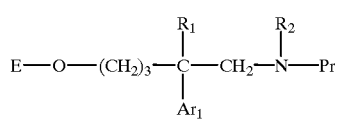
(XVII)

in which $Ar_1$, $R_1$ and $R_2$ are as defined for a compound of formula (I), E is hydrogen or an O-protecting group and Pr is an N-protecting group such as the trityl, tert-butoxycarbonyl or benzyloxycarbonyl group;

2') the O-protecting group is eventually removed from the compound of formula (XVII), by reaction with an acid or a base, to give the alcohol of the formula

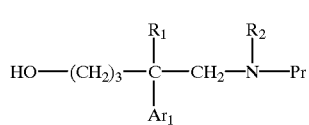
(XVIII)

3') the alcohol (XVUI) is treated with a compound of formula (VI) as defined above to give a compound of the formula

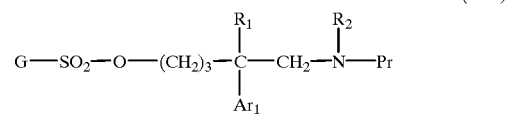
(XIX)

4') the compound (XIX) is reacted with a compound of formula (VIIIa), (VIIIb), (VIIIc), (VIIId), (VIIIe), (VIIIf), (VIIIg), (VIIIh), (VIIIi) or (VIIIj) as defined above to give a compound of the formula

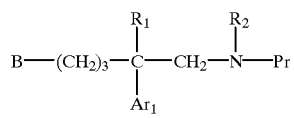
(XX)

in which B is as defined for a compound of formula (I), it being understood that when B contains a hydroxide group or an amino group, these groups can be protected;

5') the protecting group Pr is selectively removed from the compound of formula (XX) to give the compound of the formula

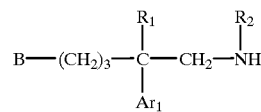
(XXI)

6') the compound of formula (XXI) is treated with a compound of formula (III), (IIIa), (IIIb), (IIIc), (IIId) or (IIIe) as defined above; and 7') after deprotection of the hydroxyl groups or amino groups, if appropriate, the resulting product is optionally converted to one of its salts with a mineral or organic acid.

More particularly, the compounds of formula (I') and their salts, especially pharmaceutically acceptable salts, are prepared by the variant of the general method described above in which:

1") a compound of the formula

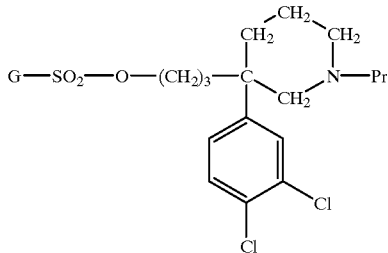

(XIX•)

in which G is a methyl, phenyl, tolyl or trifluoromethyl group and Pr is an N-protecting group such as the trityl, tert-butoxycarbonyl or benzyloxycarbonyl group, is reacted with a compound of the formula

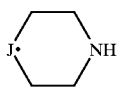

(VIII•)

in which J" is as defined for a compound of formula (I"), to give a compound of the formula

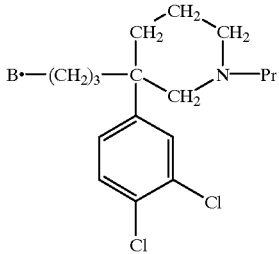

(XX•)

2") the protecting group Pr is selectively removed from the compound of formula (XX") to give the compound of the formula

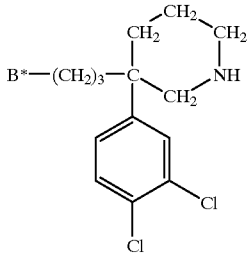

(XXI*)

3") the compound of formula (XXI") is treated with a functional derivative of an acid of the formula

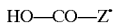

(III)

in which Z" is as defined for a compound of formula (I"); and

4") after deprotection, if appropriate, the resulting product (I") is optionally converted to one of its salts with a mineral or organic acid.

During any one of the steps for the preparation of the compounds of formula (I) or (I"), and more particularly when using compounds of formula (VIIIa), (VIIIb), (VIIIc), (VIIIe), (VIIIf), (VIIIg), (VIIIh), (VIIIi), (VIIIj) or (VIII") or intermediates of formula (II), (IV), (XX), (XXI), (XX") or (XXI"), it may be necessary and/or desirable to protect the reactive or sensitive functional groups, such as the amine, hydroxyl or carboxyl groups, present on any one of the molecules in question. This protection can be effected using the conventional protecting groups such as those described in Protective Groups in Organic Chemistry, J. F. W. McOmie, published by Plenum Press, 1973, and in Protective Groups in Organic Synthesis, T. W. Greene and P. G. M. Wutts, published by John Wiley & Sons, 1991. The protecting groups can be removed in an appropriate subsequent step by using the methods known to those skilled in the art which do not affect the rest of the molecule in question.

Thus, when E is an O-protecting group, it is selected from the conventional O-protecting groups known to those skilled in the art, for example tetrahydropyran-2-yl, benzoyl and a $(C_1-C_4)$alkylcarbonyl.

The O-protecting groups which may be used to obtain a compound of formula (I) in which $X_1$ contains a hydroxyl are the conventional O-protecting groups known to those skilled in the art, as defined above for E.

The N-protecting groups which may be used to obtain a compound of formula (I) in which $X_1$ contains an amino group are the conventional N-protecting groups known to those skilled in the art, for example the trityl, methoxytrityl, tert-butoxycarbonyl or benzyloxycarbonyl group.

In step 1) of the method or in step 6') of the variant, when using a halogenated derivative of formula (III), the reaction is carried out in an inert solvent such as tetrahydrofuran, N,N-dimethylformamide or dimethyl sulfoxide, in the presence of a base such as potassium tert-butylate, sodium hydride or lithium diisopropylamide, at a temperature between 0° C. and 80° C.

In step 1), in step 6') or in step 3"), the functional derivative of the acid (IIIa) or (III") used is the acid itself or one of the functional derivatives which react with amines, for example an anhydride, a mixed anhydride, the acid chloride or an activated ester such as the paranitrophenyl ester.

When using the acid of formula (IIIa) or (III") itself, the reaction is carried out in the presence of a coupling agent used in peptide chemistry, such as 1,3-dicyclohexylcarbodiimide or benzotriazol-1-yloxytris (dimethylamino) phosphonium hexafluorophosphate, in the presence of a base such as triethylamine or N,N-diisopropylethylamine, in an inert solvent such as dichloromethane or N,N-dimethylformamide, at a temperature between 0° C. and room temperature.

When using an acid chloride, the reaction is carried out in an inert solvent such as dichloromethane or benzene, in the presence of a base such as triethylamine or N-methylmorpholine, at a temperature between −60° C. and room temperature.

When using a chloroformate of formula (IIIb), the reaction is carried out in an inert solvent such as dichloromethane, at a temperature between 0° C. and room temperature, in the presence of a base such as triethylamine.

When using an isocyanate of formula (IIIc), the reaction is carried out in an inert solvent such as dichloromethane or benzene, at room temperature.

When using a carbamoyl chloride of formula (IIId), the reaction is carried out in a solvent such as toluene or 1,2-dichloroethane, at a temperature between 0° C. and 110° C., in the presence of a base such as triethylamine.

When using a sulfonyl chloride of formula (IIIe), the reaction is carried out in an inert solvent such as dichloromethane, in the presence of a base such as triethylamine, at a temperature between −20° C. and room temperature.

In step 2) of the method or in step 2') of the variant, the compound of formula (IV) or the compound of formula (XVII) thus obtained is deprotected, if appropriate, by the methods known to those skilled in the art. For example, when E is a tetrahydropyran-2-yl group, the deprotection is effected by acid hydrolysis using hydrochloric acid in a solvent such as ether, methanol or a mixture of these solvents, or using pyridinium p-toluenesulfonate in a solvent such as methanol, or else using an Amberlyst® resin in a solvent such as methanol, The reaction is carried out at a temperature between room temperature and the reflux temperature of the solvent. When E is a benzoyl group or a $(C_1-C_4)$alkylcarbonyl group, the deprotection is effected by hydrolysis in an alkaline medium using, for example, an alkali metal hydroxide such as sodium hydroxide, potassium hydroxide or lithium hydroxide, in an inert solvent such as water, methanol, ethanol, dioxane or a mixture of these solvents, at a temperature between 0° C. and the reflux temperature of the solvent.

In step 3) of the method or in step 3') of the variant, the reaction of the alcohol of formula (V) or the alcohol of formula (XVIII) with a sulfonyl chloride of formula (VI) is carried out in the presence of a base such as triethylamine, pyridine, N,N-diisopropylethylamine or N-methylmorpholine, in an inert solvent such as dichloromethane, benzene or toluene, at a temperature between −20° C. and the reflux temperature of the solvent.

In step 4) or in step 4'), the compound (VII) or the compound (XIX) thus obtained is reacted with a compound of formula (VIIIa), (VIIIb), (VIIIc), (VIIIe), (VIIIf), (VIIIg), (VIIIh), (VIIIi) or (VIIIj); in step 1″), the compound (XIX″) is reacted with a compound of formula (VIII″). The reaction is carried out in an inert solvent such as N,N-dimethylformamide, acetonitrile, methylene chloride, toluene, isopropanol or a mixture of these solvents, in the presence or absence of a base. When using a base, it is selected from organic bases such as triethylamine, N,N-diisopropylethylamine and N-methylmorpholine, or from alkali metal carbonates and bicarbonates such as potassium carbonate, sodium carbonate and sodium bicarbonate. In the absence of a base, the reaction is carried out using an excess of the compound of formula (VIIIa), (VIIIb), (VIIIc), (VIIIe), (VIIIf), (VIIIg), (VIIIh), (VIIIi), (VIIIj) or (VIII″) and optionally in the presence of an alkali metal iodide such as potassium iodide or sodium iodide. The reaction is carried out at a temperature between room temperature and 100° C.

In step 5') of the variant or in step 2″), the compound of formula (XX) obtained or the compound of formula (XX″) obtained is deprotected by the methods known to those skilled in the art.

The compounds of formula (I) according to the invention are finally obtained after deprotection of the hydroxyl groups or amino groups, if appropriate, or conversion of $X'_1$ to $X_1$, if appropriate.

The compounds of formula (I) or (I*) are isolated in the form of the free base or a salt by the conventional techniques.

Thus, when the compound of formula (I) or (I*) is obtained in the form of the free base, salification is effected by treatment with the chosen acid in an organic solvent. Treatment of the free base, dissolved for example in an ether such as diethyl ether, in an alcohol such as propan-2-ol, in acetone, in dichloromethane or in ethyl acetate, with a solution of the chosen acid in the same solvent gives the corresponding salt, which is isolated by the conventional techniques.

The hydrochloride, hydrobromide, sulfate, hydrogensulfate, dihydrogen-phosphate, methanesulfonate, oxalate, maleate, fumarate, naphthalene-2-sulfonate and benzenesulfonate, for example, are prepared in this way.

When the reaction has ended, the compounds of formula (I) or (I*) can be isolated in the form of one of their salts, for example the hydrochloride; in this case, if necessary, the free base can be prepared by neutralization of said salt with a mineral or organic base such as sodium hydroxide or triethylamine, or with an alkali metal carbonate or bicarbonate such as sodium or potassium carbonate or bicarbonate.

The compounds of formula (II) are obtained by known methods, particularly those described in patent applications EP-A-0 428 434, EP-A-0 474 561 and EP-A-0 512 901.

In particular, a compound of formula (II) in which $R_1$ and $R_2$ together form a group —$(CH_2)_3$— and E is a hydrogen can be prepared according to SCHEME 1 below:

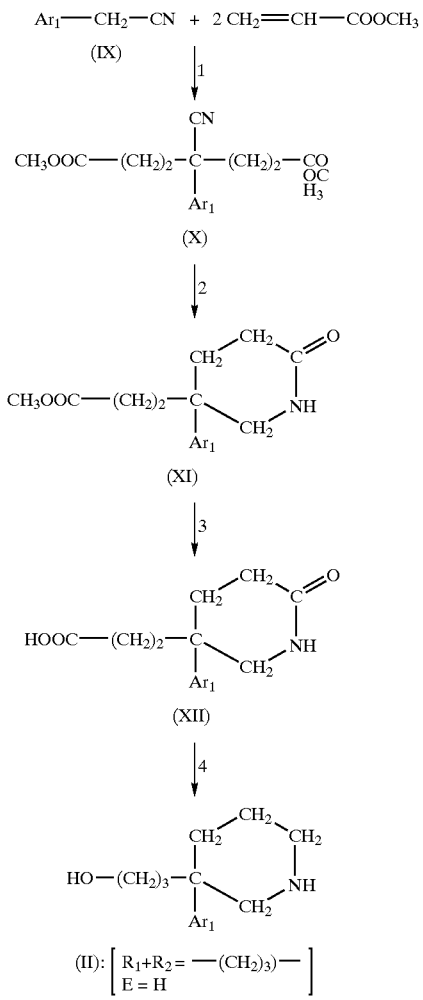

In step 1, the reaction of a compound of formula (IX) with methyl acrylate, in the presence of a base such as Triton® B or 1,8-diazabicyclo[5.4.0]undec-7-ene (DBU), gives the compound of formula (X). The reaction is carried out in an inert solvent such as 1,4-dioxane or tetrahydrofuran, at a temperature between 60° C. and the reflux temperature of the solvent.

In step 2, the compound of formula (X) is hydrogenated in the presence of a catalyst such as Raney® nickel to give the compound of formula (XI). The reaction is carried out in an inert solvent such as an alkanol, preferably ethanol or 2-methoxyethanol, at a temperature between room temperature and 60° C. and at a pressure between atmospheric pressure and 20 bar.

In step 3, the compound of formula (XI) is hydrolyzed in an alkaline medium using, for example, an alkali metal hydroxide such as sodium hydroxide or potassium hydroxide, in a solvent such as water, methanol or a mixture of these solvents, at a temperature between room temperature and the reflux temperature of the solvent.

The resulting compound of formula (XII) is reduced in step 4 to give the expected compound of formula (II). The reduction is effected by means of a reducing agent such as lithium aluminum hydride, diisobutylaluminum hydride or borane in THF, in an inert solvent such as tetrahydrofuran, 1,2-dimethoxyethane or toluene, at a temperature between room temperature and the reflux temperature of the solvent.

In particular, a compound of formula (I) in which $R_1$ and $R_2$ together form a group —$(CH_2)_4$— and E is the O-protecting group tetrahydropyran-2-yl (THP) can be prepared according to SCHEME 2 below:

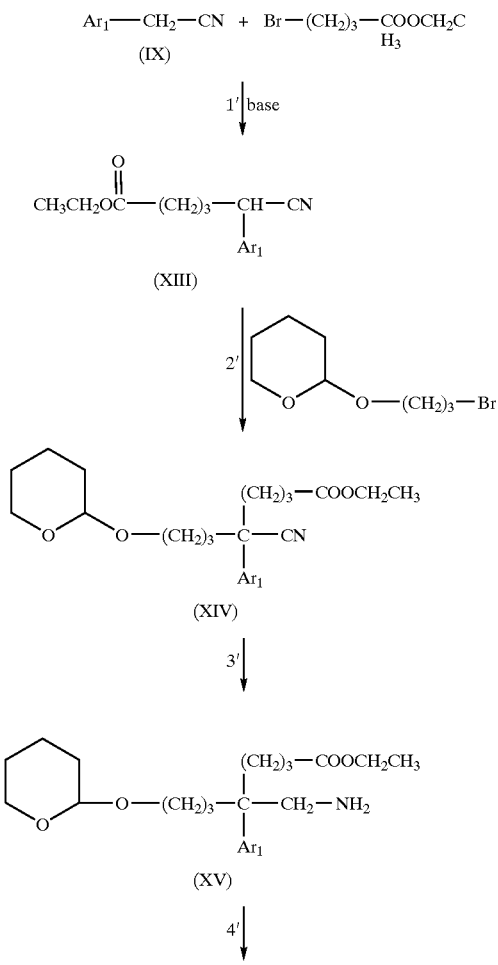

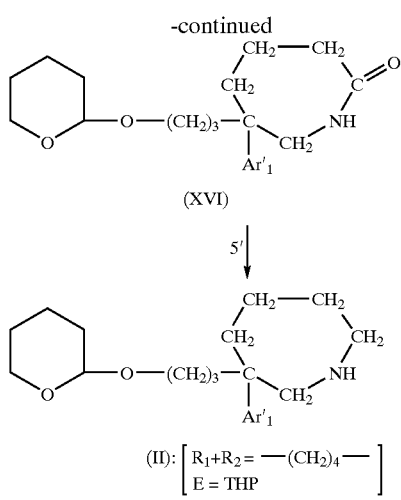

In step 1' of SCHEME 2, a compound of formula (IX) is treated with a strong base, such as sodium hydride, lithium diisopropylamide or potassium tert-butylate, to give a carbanion, which is reacted with ethyl 4-bromobutanoate to give the compound of formula (XIII).

The reaction is carried out in an inert solvent such as an ether (for example tetrahydrofuran or 1,2-dimethoxyethane), an amide (for example N,N-dimethylformamide) or an aromatic hydrocarbon (for example toluene or xylene), at a temperature between −70° C. and +60° C.

In step 2', the reaction of the compound of formula (XIII) with 2-(3-bromo-propoxy)tetrahydropyran, in the presence of a strong base such as sodium hydride, lithium diisopropylamide or potassium tert-butylate, under the operating conditions described in step 1' above, gives the compound of formula (XIV).

The nitrile derivative of formula (XIV) is reduced in step 3' to give the primary amine of formula (XV). The reduction is effected by means of hydrogen, in the presence of a catalyst such as Raney® nickel, in an inert solvent such as an alkanol, for example methanol, by itself or mixed with a saturated solution of ammonia in the same solvent, at a temperature between room temperature and 50° C.

In step 4', the cyclized compound of formula (XVI) is obtained by refluxing a solution of the compound of formula (XV) in an aromatic solvent such as toluene or xylene.

In step 5', the compound of formula (XVI) is reduced to give the expected compound of formula (II). The reduction is effected by means of a reducing agent such as lithium aluminum hydride, diisobutylaluminum hydride, sodium borohydride or borane in THF, in an inert solvent such as tetrahydrofuran, diethyl ether, 1,2-dimethoxyethane or toluene, at a temperature between room temperature and the reflux temperature of the solvent.

The compounds of formula (III), (IIIa), (IIIb), (IIIc), (IIId), (IIIe) or (III*) are known or are prepared by known methods.

The piperidines of formula (VIIIa) are known or are prepared by known methods such as those described in EP-A-0 428 434, EP-A-0 474 561, EP-A-0512901 and EP-A-0 515240.

The piperidines of formula (VIIIa) can also be prepared by methods well known to those skilled in the art, such as those described in the following publications:

J. Heterocyclic Chem., 1986, 23, 73–75;
J. Chem. Soc., 1950, 1469;
J. Chem. Soc., 1945, 917;
J. Pharm. Sci., 1972, 61, 1316–1317;
J. Org. Chem., 1957, 22, 1484–1489;
Chem. Ber., 1975, 108, 3475–3482.

The compounds of formula (VIIIa) are generally prepared in a form protected on the piperidine nitrogen; the compounds of formula (VIIIa) themselves are obtained after a deprotection step.

Different methods of obtaining the compounds of formula (VIIIa), in which the different substituents are as defined for formula (I), unless stipulated otherwise, will be indicated below as examples.

For example, when $Ar_2$ is a pyrid-2-yl group, $X'_1$ is hydroxyl and x is zero in a piperidine of formula (VIIIa), 2-bromopyridine is reacted with N-benzylpiperid-4-one in a solvent, in the presence of butyllithium, in order to prepare N-benzyl-4-hydroxy-4-(pyrid-2-yl)piperidine; 4-hydroxy-4-(pyrid-2-yl)piperidine is then obtained by deprotection in a basic medium.

Furthermore, a compound of formula (VIIIa) in which $X'_1$ is a group —$(CH_2)_m$—$OR_4$ in which $R_4$ is hydrogen and m is one or two is prepared by reducing a compound of formula (VIIIa) in which $X'_1$ is a methoxycarbonyl or, respectively, a methoxycarbonylmethyl by the method described in Chem. Ber., 1975, 108, 3475–3482.

A compound of formula (VIIIa) in which $X'_1$ is a group —$(CH_2)_m$—$OR_4$ in which $R_4$ is a ($C_1$–$C_7$)alkyl can also be prepared by alkylating a compound of formula (VIIIa) in which $X'_1$ is a group —$(CH_2)_m$—OH by the methods known to those skilled in the art.

A compound of formula (VIIIa) in which X'hd 1is a group —O—$CH_2$—$CH_2$—$OR_6$ in which $R_6$ is hydrogen can also be prepared by reacting a compound of formula (VIIIa) in which $X'_1$ is a benzoyloxy- with ethylene glycol in the presence of an acid such as sulfuric acid.

The compounds of formula (VIIIa) in which $X'_1$ is a group —O—$CH_2CH_2$—$OR_6$ in which $R_6$ is a ($C_1$–$C_7$)alkyl are prepared by an identical reaction using a 2-($C_1$ –$C_7$) alkoxyethanol.

The compounds of formula (VIIIa) in which X'hd 1is a group —O—$CH_2CH_2$—$OR_6$ in which $R_6$ is a formyl are prepared by reacting formic acid with a compound of formula (VIIIa) in which $X'_1$ is a group —O—$CH_2CH_2$—OH. The compounds of formula (VIIIa) in which $X'_1$ is a group —O—$CH_2CH_2$—$OR_6$ in which $R_6$ is a ($C_1$–$C_7$)-alkylcarbonyl are prepared by reaction with a $C_2$–$C_8$ acid chloride in the presence of a base such as triethylamine.

The compounds of formula (VIIIa) in which $X'_1$ is a group —$(CH_2)_n$—$SR_7$ or a group —$CH_2$—$S(O)_j$—($C_1$–$C_7$)alkyl are known or are prepared by known methods such as those described in WO 95/12577.

The compounds of formula (VIIIa) in which $X'_1$ is a group —$(CH_2)_m$—$OCOR_5$ ($R_5$ other than hydrogen) are prepared by reacting an acid chloride $R_5COCl$ ($R_5$ other than hydrogen) with a compound of formula (VIIIa) in which $X'_1$ is a group —$(CH_2)_m$—OH, in the presence of a base such as triethylamine.

The compounds of formula (VHIa) in which $X'_1$ is a group —$(CH_2)_m$—$OCOR_5$ in which $R_5$ is hydrogen are prepared by reacting formic acid with a compound of formula (VIIIa) in which $X'_1$ is a group —$(CH_2)_m$—OH.

The compounds of formula (VIIIa) in which $X'_1$ is a group ($C_1$–$C_7$)alkyl-NHCOO—$(CH_2)_m$— are obtained by reacting a carbamoyl chloride, ($C_1$–$C_7$)alkyl-NHCOCl, with the compounds of formula (VIIIa) in which $X'_1$ is a group —$(CH_2)_m$—OH. The same compounds are prepared by reacting an isocyanate, ($C_1$–$C_7$)alkyl-N=C=O, with the compounds of formula (VIIIa) in which $X'_1$ is a group —$(CH_2)_m$—OH.

The compounds of formula (VIIIa) in which $X'_1$ is a hydroxyl and which carry a protecting group on the piperidine nitrogen can undergo a Ritter reaction with acetonitrile in order to prepare the compounds of formula (VIIIa) in which $X'_1$ is an acetamido. The compounds of formula (VIIIa) in which $X'_1$ is a group —$NR_8R_9$ in which $R_8$ and $R_9$ are each hydrogen are then prepared by hydrolysis in an acid medium.

A compound of formula (VIIIa) in which $X'_1$ is a group —$NR_8R_9$ in which $R_8$ and $R_9$ are each hydrogen can also be prepared by hydrolyzing in a strong acid medium, for example hydrochloric acid, a compound of formula (VIIIa) in which $X'_1$ is an isocyanato group.

A compound of formula (VIIIa) in which $X'_1$ is a group —$NR_8R_9$ in which $R_8$ is hydrogen and $R_9$ is a ($C_1$–$C_7$)alkyl, or a ($C_3$–$C_7$)cycloalkylmethyl or a benzyl, can be prepared by reducing a compound of formula (VIIIa) in which $X'_1$ is a group —$NR_{12}COR_{13}$ in which $R_{12}$ is hydrogen and $R_{13}$ is a hydrogen or a ($C_1$–$C_6$)alkyl or, respectively, a ($C_3$–$C_7$) cycloalkyl or a phenyl. The reaction is carried out by means of a reducing agent such as lithium aluminum hydride, in a solvent such as tetra-hydrofuran, at the reflux temperature of the solvent.

The compounds of formula (VIIIa) in which $X'_1$ is a group —$NR_8R_9$ in which $R_8$ is a ($C_1$–$C_7$)alkyl can be prepared by an identical reaction from the compounds of formula (VIIIa) in which $X'_1$ is a group —$NR_{12}COR_{13}$ in which $R_{12}$ is a ($C_1$–$C_7$)alkyl.

A compound of formula (VIIIa) in which $X'_1$ is a group —$NR_8R_9$ in which $R_8$ and $R_9$, together with the nitrogen atom to which they are bonded, form a hetero-cycle is prepared by applying or adapting Bruylants' reaction (Bull. Soc. Chim. Belges, 1924, 33 467, and Tetrahedron Letters, 1988, 29 (52), 6827–6830).

A compound of formula (VIIIa) in which $X'_1$ is a group —$CH_2$—$NR_{10}R_{11}$ in which $R_{10}$ and $R_{11}$ are each hydrogen is prepared by reducing a compound of formula (VIIIa) in which $X'_1$ is a cyano. This reduction is effected by the methods well known to those skilled in the art.

A compound of formula (VIIIa) in which $X'_1$ is a group —$CH_2$—$CH_2$—$NR_1OR_{11}$ in which $R_{10}$ and $R_{11}$ are each a hydrogen is prepared from a compound of formula (VIIIa) in which $X'_1$ is a group —$CH_2$—$CH_2$—OH by applying or adapting the method described in J. Med. Chem., 1989, 32, 391–396.

The compounds of formula (VIIIa) in which $X'_1$ is a group —$(CH_2)_p$—$NR_1OR_{11}$ in which $R_{10}$ is a hydrogen or a ($C_1$–$C_7$)alkyl and $R_{11}$ is a ($C_1$–$C_7$)alkyl, a ($C_3$–$C_7$)-cycloalkylmethyl or a benzyl can be prepared by reducing a compound of formula (VIIIa) in which $X'_1$ is a group —$(CH_2)_p$—$NR_{14}C(=W_1)R_{16}$ in which $R_{14}$ is a hydrogen or a ($C_1$–$C_7$)alkyl, $R_{16}$ is a hydrogen, a ($C_1$–$C_6$)alkyl, a ($C_3$–$C_7$)cycloalkyl or a phenyl and $W_1$ is an oxygen atom.

The compounds of formula (VIIIa) in which $X'_1$ is a group —$NR_{12}COR_{13}$ in which $R_{12}$ is a hydrogen or a ($C_1$–$C_7$)alkyl and $R_{13}$ is hydrogen or respectively a ($C_1$–$C_7$)alkyl, an optionally substituted ($C_3$–$C_7$)cycloalkyl, a phenyl, a benzyl, a vinyl, a pyridyl, a furyl, a thienyl, a pyrrolyl or an imidazolyl are obtained by reacting formic acid in acetic anhydride or, respectively, an appropriate acid chloride $R_{13}COCl$, in the presence of a base such as triethylamine, with a compound of formula (VIIIa) in which $X'_1$ is a group —$NHR_{12}$. In particular, a compound of formula (VIIIa) in which $X'_1$ is a group —$NR_{12}COR_{13}$ in which $R_{13}$ is an ethyl radical can be prepared by hydrogenating, in the presence of a catalyst such as palladium on charcoal, a compound of formula (VIIIa) in which $X'_1$ is an acryloylamino or acryloyl-N-($C_1$–$C_7$)alkylamino group.

A compound of formula (VIIIa) in which $X'_1$ is a group —$NR_{12}COR_{13}$ in which $R_{12}$ and $R_{13}$ together are a group —$(CH_2)_3$— or —$(CH_2)_4$— is prepared by applying or adapting the method described in J. Med. Chem., 1985, 28, 46–50.

A compound of formula (VIIIa) in which $X'_1$ is a group —$NR_{14}COCOR_{15}$ in which $R_{15}$ is a ($C_1$–$C_4$)alkoxy is prepared by reacting a compound of the formula Cl—$COCOR_{15}$ with a compound of formula (VIIIa) in which $X'_1$ is a group —$NHR_{14}$.

The compounds of formula (VIIIa) in which $X'_1$ is a group —$(CH_2)_p$—$NR_{14}C(=W_1)R_{16}$ in which $W_1$ is an oxygen atom, p is 1 or 2, $R_{14}$ is a hydrogen or a ($C_1$–$C_7$)alkyl and $R_{16}$ is a hydrogen or respectively a ($C_1$–$C_7$)alkyl, a phenyl, a benzyl, a pyridyl, an optionally substituted ($C_3$–$C_7$) cycloalkyl, a vinyl, a furyl, a thienyl, a pyrrolyl or an imidazolyl are obtained by reacting formic acid in acetic anhydride or, respectively, an appropriate acid chloride $R_{16}COCl$, in the presence of a base such as triethylamine, with a compound of formula (VIIIa) in which $X'_1$ is a group —$CH_2$—$NHR_{14}$ or —$CH_2$—$CH_2$—$NHR_{14}$.

A compound of formula (VIIIa) in which $X'_1$ is a group —$(CH_2)_p$—$NR_{14}C(=W_1)R_{16}$ in which $W_1$ is a sulfur atom is obtained from a corresponding compound of formula (VIIIa) which is protected on the piperidine nitrogen and in which $W_1$ is an oxygen atom by reaction with phosphorus pentasulfide or with Lawesson's reagent, 2,4-bis(4-methoxyphenyl)-1,3-dithia-2,4-disphosphetane-2,4-disulfide, followed by deprotection of the piperidine nitrogen.

A compound of formula (VIIIa) in which $X'_1$ is a group —$(CH_2)_m$—$NR_{14}COOR_{17}$ is prepared by reacting a chloroformate of the formula $ClCOOR_{17}$ with a compound of formula (VIIIa) in which $X'_1$ is a group $(CH_2)_m NHR_{14}$, in the presence of a base such as triethylamine.

It is also possible to prepare a compound of formula (VIIIa) in which $X'_1$ is a group $(CH_2)_m$—$NR_{14}COOR_{17}$ in which m=0 and $R_{14}$ is hydrogen by reacting a compound $R_{17}OH$ with a compound of formula (VIIIa) in which $X'_1$ is an isocyanato group (—N=C=O).

A compound of formula (VIIIa) in which $X'_1$ is an isocyanato group is prepared from a compound of formula (VIIIa) in which $X'_1$ is a carboxyl group by the method described in Organic Synthesis, 51, 48–52.

A compound of formula (VIIIa) in which $X'_1$ is a group $(CH_2)_m$—$NR_{14}SO_2R_{18}$ is prepared by reacting a sulfonyl chloride $ClSO_2R_{18}$ with a compound of formula (VIIIa) in which $X'_1$ is a group —$(CH_2)_m$—$NHR_{14}$, in the presence of a base such as triethylamine.

Likewise, the compounds of formula (VIIIa) in which $X'_1$ is a group —$(CH_2)_m$—$NR_{14}CONR_{19}R_{20}$ in which $R_{19}$ is a hydrogen and $R_{20}$ is a ($C_1$–$C_7$)alkyl are prepared by reaction with an isocyanate of the formula $R_{20}N=C=O$ in which $R_{20}$ is a ($C_1$–$C_7$)alkyl.

The compounds of formula (VIIIa) in which $X'_1$ is a group —$(CH_2)_m$—N—$R_{14}CONR_{19}R_{20}$ in which $R_{19}$ is a ($C_1$–$C_7$) alkyl are prepared by reaction with a carbamoyl chloride of the formula $ClCONR_{19}R_{20}$.

A compound of formula (VIIIa) in which $X'_1$ is a group —$(CH_2)_m$—$NR_{14}CONR_{19}R_{20}$ can also be obtained by reacting a compound $HNR_{19}R_{20}$ with a compound of formula (VIIIa) in which $X'_1$ is a group —$(CH_2)_m$—$NR_{14}COOR_{17}$ in which $R_{17}$ is a phenyl.

A compound of formula (VIIIa) in which $X'_1$ is a group —$(CH_2)_m$—$NR_{14}CONR_{19}R_{20}$ in which m=0 and $R_{14}$ is hydrogen can also be prepared by reacting a compound $NHR_{19}R_{20}$ with a compound of formula (VIIIa) in which $X'_1$ is an isocyanato group.

A compound of formula (VIIIa) in which $X'_1$ is a group —$(CH_2)_m$—$NR_{14}C(=W_1)NR_{19}R_{20}$ in which $W_1$ is a sulfur atom is prepared by reacting a compound of formula (VIIIa), protected on the piperidine nitrogen, in which $X'_1$ is a group —$(CH_2)_m$—$NR_{14}CONR_{19}R_{20}$ with phosphorus pentasulfide or with Lawesson's reagent.

A compound of formula (VIIIa) in which $X'_1$ is a group —$CONR_{19}R_{20}$ is prepared by reacting a compound of formula (VIIIa) in which $X'_1$ is a carboxyl with a compound of formula $HNR_{19}R_{20}$ by the methods well known to those skilled in the art.

Likewise, the compounds of formula (VIIIa) in which $X'_1$ is a group —$CH_2$—$CONR_{19}R_{20}$ are prepared by reacting a compound of formula (VIIIa) in which $X'_1$ is a group —$CH_2$—$COOR_2$ in which $R_{21}$ is hydrogen with a compound $HNR_{19}R_{20}$.

A compound of formula (VIIIa) in which $X'_1$ is a group $(CH_2)_n$—$C(=W_1)NR_{19}R_{20}$ in which $W_1$ is a sulfur atom is prepared, by the above-mentioned methods, from a compound of corresponding formula (VIIIa) in which $W_1$ is an oxygen atom.

A compound of formula (VIIIa) in which $X'_1$ is a carboxyl can be prepared by hydrolyzing a compound of formula (VIIIa) in which $X'_1$ is a cyano by the methods known to those skilled in the art.

A compound of formula (VIIIa) in which $X'_1$ is a carboxymethyl can be prepared by the method described in Chem. Ber., 1975, 108, 3475–3482.

A compound of formula (VIIIa) in which $X'_1$ is a ($C_1$–$C_7$) alkoxycarbonyl or a ($C_1$–$C_7$)alkoxycarbonylmethyl can be prepared from a compound of formula (VIIIa) in which $X'_1$ is a carboxyl or, respectively, a carboxymethyl by means of an esterification reaction by the methods well known to those skilled in the art.

In particular, a compound of formula (VIIIa) in which $Ar_2$ is an optionally substituted phenyl radical, x is one and $X'_1$ is a ($C_1$–$C_7$)alkoxycarbonyl is prepared by reacting a protected 4-($C_1$–$C_7$)alkoxycarbonylpiperidine with an optionally substituted benzyl halide in the presence of a base such as sodium hydride, potassium tert-butylate or sodium diisopropylamide, in a solvent such as tetra-hydrofuran, N,N-dimethylformamide or dimethyl sulfoxide, at a temperature between −78° C. and room temperature. The expected compound of formula (VIIIa) is obtained after a deprotection step.

A compound of formula (VIIIa) in which $X'_1$ is a group —CO—$NR_{22}$—$NR_{23}R_{24}$ is prepared by reacting a hydrazine $HNR_{22}$—$NR_{23}R_{24}$ with a compound of formula (VIIIa) in which $X'_1$ is a chloroformyl.

A compound of formula (VIIIa) in which $X'_1$ is a group

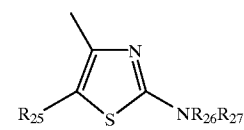

in which $R_{26}$ and $R_{27}$ are each independently a hydrogen or a ($C_1$–$C_7$)alkyl is prepared by reacting a compound of formula (VIIIa) in which $X'^1$ is a group

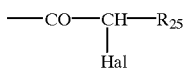

in which Hal is a halogen atom, preferably bromine, with a thiourea in which one of the amino groups is free or substituted by one or two ($C_1$-$C_7$)alkyls.

A compound of formula (VIIIa) in which $X'_1$ is a group

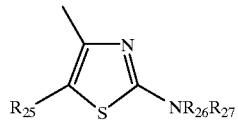

in which $R_{27}$ is a formyl or respectively a ($C_1$-$C_7$) alkylcarbonyl is prepared by reacting formic acid in acetic anhydride or, respectively, an acid chloride ($C_1$-$C_7$)alkyl-COCl, in the presence of a base such as triethylamine, with the above compound of formula (VIIIa), protected on the piperidine nitrogen, in which $R_{27}$ is hydrogen. The expected compound is obtained after a deprotection step.

The compound of formula (VIIIa) in which $X'_1$ is a group

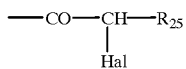

in which Hal is a bromine atom is obtained by the bromination, by the conventional methods, of a compound of formula (VIIIa) in which $X'_1$ is a group —CO—$CH_2$—$R_{25}$.

A compound of formula (VIIIa) in which $X'_1$ is a group

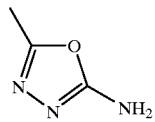

can be prepared by reacting a protected compound of formula (VIIIa) in which $X'_1$ is a carbazoyl group (—CONH—$NH_2$) with cyanogen bromide by the method described in J. Org. Chem., 1961, 26, 88–95. The compound of formula (VIIIa) in which $X'_1$ is a carbazoyl group is obtained by reacting hydrazine with a compound of formula (VIIIa) in which $X'_1$ is a chloroformyl, which is itself obtained by reacting thionyl chloride with a compound of formula (VIIIa) in which $X'_1$ is a carboxyl.

The piperazines of formula (VIIIb) are known or are prepared by known methods such as those described in EP-A-0 428 434.

The piperidines of formula (VIIIc) are known or are prepared by known methods such as those described in WO 94/10146.

The piperidines of formula (VIIId) are known or are prepared by known methods such as those described in EP-A-0 625 509.

The piperidines of formula (VIIIe) are known or are prepared by known methods such as those described in EP-A-0 630 887.

The piperidines of formula (VIIIf) are known or are prepared by known methods such as those described in WO 94/26735.

The compounds of formula (VIIIg) are known or are prepared by known methods such as those described in WO 94/29309.

The piperidines of formula (VIIIh) are known or are prepared by known methods such as those described in WO 95/05377.

The piperidines of formula (VIIIi) are known or are prepared by known methods such as those described in WO 95/12577.

The piperidines of formula (VIIIj) are known or are prepared by known methods.

In particular, the piperidines of formula (VIIIj) in which $J'_6$ is a group

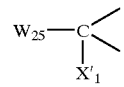

in which $X'_1$ is other than hydrogen and $W_{25}$ is a ($C_1$-$C_7$) alkyl or a ($C_3$-$C_7$)cycloalkyl are prepared by the procedures described above for the preparation of the piperidines of formula (VIIIa).

A piperidine of formula (VIIIj) in which $J'_6$ is a group

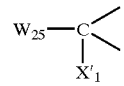

in which $W_{25}$ is a group —$NR_{79}R_{80}$ and $X'_1$ is a cyano is prepared by means of a Strecker reaction between a 1-benzylpiperid-4-one and a compound of the formula $NHR_{79}R_{80}$ in the presence of sodium cyanide. The compound of expected formula (VIIIj) is obtained after a deprotection step. Hydrolysis of the cyano group in a strong medium by the methods known to those skilled in the art gives the corresponding piperidines of formula (VIIIj) in which $X'_1$ is a carboxyl. The latter compounds can be used to obtain the corresponding piperidines of formula (VIIIj) in which $X'_1$ is a ($C_1$-$C_7$)alkoxycarbonyl or a group —$CONR_{19}R_{20}$ by the methods known to those skilled in the art, for example by means of esterification or, respectively, by the methods of peptide coupling.

The piperidines of formula (VIII*) are also known or can be prepared by known methods. In particular, when J* is a group of the structure

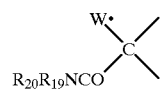

the piperidine of formula (VIII*) is prepared by one of the methods described above for the compounds of formula (VIIIa) in which $X'_1$ is a group —$CONR_{19}R_{20}$, especially by reacting a carboxylic acid of the formula

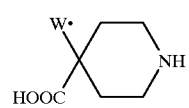

(VIIIa*)

with an amine of the formula $NHR_{19}R_{20}$.

When J˙ is a group of the structure

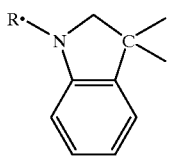

the piperidine of formula (VIII˙) is prepared by methods described in WO 94/29309.

The enantiomers of the compounds according to the invention, of the formula

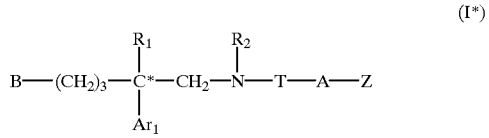

in which:
"*" denotes that the carbon atom carrying this label has the determined (+) or (−) absolute configuration; and
$R_1$, $R_2$, $Ar_1$, T, A, Z and B are as defined for the compounds of formula (I), and their salts with mineral or organic acids, are novel compounds which form part of the invention.

The enantiomers of formula (I*) can be isolated by resolution of the racemic mixtures of the compounds of formula (I). It is preferable, however, to resolve the racemic mixtures at the stage of an intermediate which can be used to prepare a compound of formula (I), as described in patent applications EP-A-0 474 561, EP-A-0 512 901, EP-A-0 591 040 and EP-A-0 612 716.

The compounds of formula (I) above also include those in which one or more hydrogen, carbon or iodine atoms have been replaced by their radioactive isotope, for example tritium, carbon 14 or iodine 125. Such labeled compounds are useful in research, metabolic or pharmacokinetic studies and in biochemical assays as receptor ligands.

The affinity of the compounds of formula (I) for the tachykinin receptors was evaluated in vitro by means of several biochemical assays using radioligands:

1˙) The binding of $[^{125}I]$BH-SP (substance P labeled with iodine 125 using Bolton-Hunter's reagent) to the $NK_1$ receptors of rat cortex, guinea-pig ileum and human lymphoblastic cells.

2˙) The binding $[^{125}I]$His-$NK_A$ to the $NK_2$ receptors of rat bladder or the binding $[^{125}I]$NPγ to the $NK_2$ receptors of guinea-pig ileum.

3˙) The binding $[^{125}I]$His[MePhe$^7$]$NK_B$ to the $NK_3$ receptors of rat cerebral cortex, guinea-pig cerebral cortex and gerbil cerebral cortex and to the human $NK_3$ cloned receptors expressed by CHO cells (Buell et al., FEBS Letters, 1992, 299, 90–95).

The assays were performed according to X. Emonds-Alt et al. (Eur. J. Pharmacol., 1993, 250, 403–413).

The compounds according to the invention strongly inhibit the binding of $[^{125}I]$His[MePhe$^7$]$NK_B$ to the $NK_3$ receptors of guinea-pig and gerbil cerebral cortex and to the human $NK_3$ cloned receptors: the inhibition constant Ki is generally less than $5.10^{-9}$ M. For the same compounds, it was found that the inhibition constant (Ki) for the $NK_3$ receptors of rat cerebral cortex is generally greater than $10^{-9}$ M and that the inhibition constant (Ki) for the $NK_2$ receptor of rat duodenum and the $NK_1$ receptors of rat cortex is generally greater than or equal to $10^{-7}$ M.

The compounds according to the present invention were also evaluated in vivo on two animal models.

In the gerbil, a rotational behavior is induced by the intrastriatal administration of the specific $NK_3$ receptor agonist senktide; it was found that a unilateral administration of senktide to gerbil striatum leads to strong contralateral rotations which are inhibited by the compounds according to the invention, administered either intraperitoneally or orally.

This result shows that the compounds according to the invention pass through the blood-brain barrier and that they are capable of blocking the characteristic action of the $NK_3$ receptors in the central nervous system. They may thus be used for the treatment of any $NK_B$-dependent pathological condition of the central nervous system, such as psychiatric diseases, or any pathological condition mediated by the $NK_3$ receptor in the central nervous system, such as psychosomatic diseases.

In the guinea-pig, an intravenous or intracerebroventricular injection of senktide induces hypertension which is suppressed by the oral or intravenous administration of the compounds according to the invention.

This result shows that the compounds according to the invention act on the cardiovascular system and that they are capable of blocking the characteristic action of the $NK_3$ receptors in said system, especially hypertension (Nakayama et al., Brain Res., 1992, 595, 339–342; Takano and Kamiya, Asia Pacific J. Pharmacol., 1991, 6, 341–346; Saigo et al., Neuroscience Letters, 1993, 159, 187–190).

In the guinea-pig, the inhalation of substance P, for example, induces bronchial hyperreactivity to acetylcholine and hypersensitivity to histamine, for example in the plasmic extravasation. An $NK_3$ antagonist blocks these two characteristic processes of respiratory pathological conditions like asthma.

In these tests, the compounds according to the invention are active at doses varying from 0.1 mg to 30 mg per kg, administered orally, intravenously or intraperitoneally.

The compounds of the present invention are generally administered in dosage units. Said dosage units are preferably formulated into pharmaceutical compositions in which the active principle is mixed with a pharmaceutical excipient.

According to another of its aspects, the present invention relates to pharmaceutical compositions containing, as the active principle, a compound of formula (I) or one of its pharmaceutically acceptable salts which has a very high affinity for the human $NK_3$ receptor, said affinity being characterized by an inhibition constant Ki generally of less than $5.10^{-9}$ M in ligand binding studies.

The compounds of formula (I) and their pharmaceutically acceptable salts can be used in daily doses of 0.01 to 100 mg per kilogram of body weight of the mammal to be treated, preferably in daily doses of 0.1 to 50 mg/kg. In humans the dose can preferably vary from 0.5 to 4000 mg per day, more particularly from 2.5 to 1000 mg, depending on the age of the subject to be treated or the type of treatment: prophylactic or curative.

Examples of diseases which can be treated using the compounds and their pharmaceutically acceptable salts are diseases associated with a dysfunction of the dopaminergic systems, such as schizophrenia and Parkinson's disease, diseases associated with a dysfunction of the noradrenergic and serotoninergic systems, such as anxiety, vigilance disorders and humor disorders, all forms of epileptic disease, particularly grand mal, dementia, neurodegenerative diseases, peripheral diseases in which the central nervous system and/or the peripheral nervous system participate via neurokinin B acting as a neurotransmitter or neuromodulator, such as pain, migraine and acute or chronic inflammation, cardiovascular disorders, particularly hypertension, cardiac insufficiency and rhythm disorders, respiratory disorders (asthma, rhinitis, cough, bronchitis, allergy, hypersensitivity), disorders of the gastrointestinal system, such as esophageal ulcer, colitis, stress-related disorders, irritable bowel syndrome (IBS) and acidic secretion, emesis/nausea (following chemotherapy, postoperative, due to travel sickness or due to vestibular disorders), disorders of the urinary system (incontinence, nervous bladder), diseases of the immune system (rheumatoid arthritis) and, more generally, any neurokinin B-dependent pathological condition.

In the pharmaceutical compositions of the present invention for oral, sublingual, inhalational, subcutaneous, intramuscular, intravenous, transdermal, local or rectal administration, the active principles can be administered to animals and humans in unit forms of administration, mixed with conventional pharmaceutical carriers. The appropriate unit forms of administration include forms for oral administration, such as tablets, gelatin capsules, powders, granules and solutions or suspensions to be taken orally, forms for sublingual and buccal administration, forms for subcutaneous, intramuscular, intravenous, intranasal or intraocular administration and forms for rectal administration.

When a solid composition in the form of tablets is prepared, the main active principle is mixed with a pharmaceutical vehicle such as silica, gelatin, starch, lactose, magnesium stearate, talcum, gum arabic or the like. The tablets can be coated with sucrose various polymers or other appropriate substances or else they can be treated so as to have a sustained or delayed activity and so as to release a predetermined amount of active principle continuously.

A preparation in the form of gelatin capsules is obtained by mixing the active principle with a diluent, such as a glycol or a glycerol ester, and introducing the mixture obtained into soft or hard gelatin capsules.

A preparation in the form of a syrup or elixir can contain the active principle together with a sweetener, which is preferably calorie-free, methylparaben and propylparaben as antiseptics, a flavoring and an appropriate color.

The water-dispersible granules or powders can contain the active principle mixed with dispersants or wetting agents or with suspending agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral, intranasal or intraocular administration is effected using aqueous suspensions, isotonic saline solutions or injectable solutions which contain pharmacologically compatible dispersants and/or wetting agents, for example propylene glycol or butylene glycol.

Administration by inhalation is effected using an aerosol which also contains, for example, sorbitan trioleate or oleic acid, as well as trichlorofluoromethane, dichlorofluoromethane, dichlorotetrafluoroethane or any other biologically compatible propellant gas; it is also possible to use a system containing the active principle, by itself or in association with an excipient, in powder form.

The active principle can also be presented in the form of a complex with a cyclodextrin, for example α-, β- or γ-cyclodextrin, 2-hydroxypropyl-β-cyclodextrin or methyl-β-cyclodextrin.

The active principle can also be formulated as microcapsules, with one or more carriers or additives if appropriate.

In each dosage unit, the active principle of formula (I) is present in the amounts commensurate with the daily doses envisaged. In general, each dosage unit is appropriately adjusted according to the dosage and the intended type of administration, for example tablets, gelatin capsules and the like, sachets, ampoules, syrups and the like, or drops, so that said dosage unit contains from 0.5 to 1000 mg of active principle, preferably from 2.5 to 250 mg, for administration one to four times a day.

The above-mentioned compositions can also contain other active products which are useful for the desired therapeutics, such as, for example, bronchodilators, antitussives or antihistamines.

By virtue of their very high affinity for the human $NK_3$ receptor and their high selectivity, the compounds according to the invention may be used in radio-labeled form as laboratory reagents.

For example, they make it possible to characterize, identify and locate the human $NK_3$ receptor in tissue sections or the $NK_3$ receptor in the whole animal by autoradiography.

The compounds according to the invention also make it possible to sort or screen molecules as a function of their affinity for the human $NK_3$ receptor. This is carried out by means of a reaction in which the radiolabeled ligand forming the subject of the present invention is displaced from its human $NK_3$ receptor.

The following abbreviations are used in the Preparations and in the

EXAMPLES

Me, OMe: methyl, methoxy

Et, OEt: ethyl, ethoxy

EtOH: ethanol

MeOH: methanol

Ether: diethyl ether

Iso ether: diisopropyl ether

DMF: dimethylformamide

DMSO: dimethyl sulfoxide

DCM: dichloromethane

THF: tetrahydrofuran

AcOEt: ethyl acetate $K_2CO_3$: potassium carbonate $Na_2CO_3$: sodium carbonate $KHCO_3$: potassium hydrogencarbonate $NaHCO_3$: sodium hydrogencarbonate NaCl: sodium chloride $Na_2SO_4$: sodium sulfate $MgSO_4$: magnesium sulfate NaOH: sodium hydroxide AcOH: acetic acid $H_2SO_4$: sulfuric acid HCl: hydrochloric acid Ethereal hydrogen chloride: saturated solution of hydrochloric acid in ether BOP: benzotriazol-1-yloxytris(dimethylamino) phosphonium hexafluorophosphate KCN: potassium cyanide DBU: 1,8-diazabicyclo[5.4.0]undec-7-ene NH$_4$Cl: ammonium chloride M.p.: melting point B.p.: boiling point RT: room temperature Silica H: silica gel 60H marketed by Merck (DARMSTADT)

NMR: nuclear magnetic resonance

δ: chemical shift s: singlet bs: broad singlet rs: resolved singlet d: doublet t: triplet qd: quadruplet sept: septuplet mt: multiplet us: unresolved signals

PREPARATION 1.1

4-(Pyrrolidin-1-ylcarbonyl)piperidine Hydrochloride

A) 1-tert-Butoxycarbonyl-4-carboxypiperidine 8.6 g of triethylamine and 20 ml of water are added to a solution of 10 g of isonipecotic acid in 100 ml of dioxane and the mixture is heated to 60° C. 20.25 g of di-tert-butyl carbonate are then added dropwise and the mixture is stirred for 1 hour at 60° C. and refluxed for 30 minutes. It is concentrated under vacuum, the residue is taken up with water and acidified to pH 3 by the addition of 2 N HCl solution and the precipitate formed is filtered off to give 17 g of the expected product.

B) 1-tert-Butoxycarbonyl-4-(pyrrolidin-1-ylcarbonyl)piperidine 1.32 g of triethylamine, 2.5 g of the compound obtained in the previous step and then 5.31 g of BOP are added to a solution of 0.77 g of pyrrolidine in 20 ml of DCM and the mixture is stirred for 1 hour at RT. It is concentrated under vacuum, the residue is taken up with water and extracted with ether, the organic phase is washed with water, with 10% NaOH solution, with water, with a buffer solution of pH 2, with water and with saturated NaCl solution and dried over MgSO$_4$ and the solvent is evaporated off under vacuum to give 2.25 g of the expected product.

C) 4-(Pyrrolidin-1-ylcarbonyl)piperidine hydrochloride p 20 ml of 6 N HCl solution are added to a solution of 2.25 g of the compound obtained in the previous step in 40 ml of MeOH and the mixture is stirred for 1 hour at RT. The solvent is concentrated under vacuum, the residue is taken up with acetone and the solvent is evaporated off under vacuum to give 1.75 g of the expected product after crystallization from AcOEt.

PREPARATION 1.2

4-Carbamoyl-4-(piperid-1-yl)piperidine Dihydrochloride

A) 1-Benzyl-4-cyano-4-(piperid-1-yl)piperidine

A solution of 5.3 g of sodium cyanide in 20 ml of water is added dropwise at RT to a solution of 18.9 g of 1-benzylpiperid-4-one and 12.16 g of piperidine hydrochloride in 25 ml of MeOH and 25 ml of water and the mixture is stirred for 48 hours at RT. The precipitate formed is filtered off, washed with water and dried under vacuum to give 27 g of the expected product.

B) 1-Benzyl-4-carbamoyl-4-(piperid-1-yl)piperidine 10 g of the compound obtained in the previous step are added to 50 ml of 95% sulfuric acid and the mixture is heated at 100° C. for 45 minutes. After cooling to RT, the reaction mixture is poured onto 100 g of ice, 250 ml of DCM are added, with cooling, the organic phase is dried over MgSO$_4$ and the solvent is evaporated off under vacuum. The solid product obtained is recrystallized from 300 ml of an acetonitrile/toluene mixture (65/35; v/v) to give 9.7 g of the expected product, m.p.=150–160° C.

C) 4-Carbamoyl-4-(piperid-1-yl)piperidine Dihydrochloride 10 g of ammonium formate and 2.5 g of 5% palladium on charcoal are added to a solution of 9.7 g of the compound obtained in the previous step in 200 ml of MeOH and the mixture is stirred for 2 hours at RT. It is filtered on Célite® and the filtrate is evaporated under vacuum. The residue is dissolved in 2 N HCl solution, rendered alkaline to pH 13 by the addition of 40% NaOH solution and extracted with chloroform, the organic phase is dried over MgSO$_4$ and the solvent is evaporated off under vacuum. The product obtained is dissolved in an MeOH/DCM mixture, acidified to pH 1 by the addition of ethereal hydrogen chloride and evaporated under vacuum to give 5 g of the expected product, m.p.=185° C.

PREPARATION 1.3

4-(Acryloyl-N-methylamino)-4-phenylpiperidine Hydrochloride

A) 1-Benzyl-4-hydroxy-4-phenylpiperidine

This compound is prepared by reacting phenyllithium with 1-benzylpiperid-4-one by the method described in EP-A-474 561.

B) 4-Acetamido-1-benzyl-4-phenylpiperidine

This compound is prepared by reacting acetonitrile with the compound obtained in the previous step by the method described in EP-A-474 561.

C) 4-Amino-1-benzyl-4-phenylpiperidine Dihydrochloride

A mixture of 50 g of the compound obtained in the previous step, 90 ml of concentrated HCl solution and 210 ml of water is refluxed for 48 hours. The reaction mixture is concentrated under vacuum, the residue is taken up with an EtOH/toluene mixture and the solvents are evaporated off under vacuum. The residue is dissolved in 100 ml of hot MeOH, 500 ml of acetone are added and the mixture is stirred, with cooling in an ice bath. The crystals formed are filtered off, washed with acetone and then with ether and dried to give 48.9 g of the expected product.

D) 1-Benzyl-4-(formylamino)-4-phenylpiperidine 110 ml of acetic anhydride are added dropwise to a solution of 48.9 g of the compound obtained in the previous step and 25 g of sodium formate in 340 ml of formic acid and the reaction mixture is then left to stand overnight at RT, with stirring. It is concentrated under vacuum, the residue is taken up with water, rendered alkaline by the addition of concentrated NaOH solution and extracted with DCM, the organic phase is dried over MgSO$_4$ and the solvent is evaporated off under vacuum to give 38.8 g of the expected product after crystallization from an iso ether/pentane mixture, m.p.=140° C.

E) 1-Benzyl-4-(methylamino)-4-phenylpiperidine

A solution of 38.8 g of the compound obtained in the previous step in 400 ml of THF is added slowly to a suspension of 12.5 g of lithium aluminum hydride in 100 ml of THF and the reaction mixture is refluxed for 3 hours. After cooling, a solution of 5 ml of concentrated NaOH in 45 ml of water is added, the inorganic salts are filtered off and the filtrate is concentrated under vacuum to give 38 g of the expected product.

F) 4-(Acryloyl-N-methylamino)-1-benzyl-4-phenylpiperidine

A solution of 1.5 g of the compound obtained in the previous step and 1.5 ml of triethylamine in 40 ml of DCM is cooled to 0–5° C., 0.5 ml of acryloyl chloride is added dropwise and the reaction mixture is stirred, the temperature being allowed to rise to RT. It is poured into water, the resulting mixture is decanted, the organic phase is washed with water and with 2 N NaOH solution and dried over $MgSO_4$ and the solvent is evaporated off under vacuum to give 1.3 g of the expected product after crystallization from an ether/pentane mixture.

G) 4-(Acryloyl-N-methylamino)-4-phenylpiperidine Hydrochloride

A solution of 1.3 g of the compound obtained in the previous step in 30 ml of 1,2-dichloroethane is cooled to 0° C., 0.5 ml of 1-chloroethyl chloroformate is added dropwise and the reaction mixture is then refluxed for 2 hours. It is concentrated under vacuum and the residue is taken up with 15 ml of MeOH, refluxed for 30 minutes and concentrated under vacuum to give 0.65 g of the expected product after crystallization from AcOEt.

PREPARATION 1.4

4-(2-Aminothiazol-4-yl)-4-phenylpiperidine p-toluenesulfonate Monohydrate

A) 4-(2-Bromoacetyl)-4-phenylpiperidine Hydrobromide 8 g of bromine are added rapidly at RT to a suspension of 11.98 g of 4-acetyl-4-phenylpiperidine hydrochloride in 200 ml of DCM and the reaction mixture is left to stand overnight at RT, with stirring. It is diluted by the addition of 200 ml of ether and the precipitate formed is filtered off and washed with ether to give 17.88 g of the expected product after drying under vacuum.

B) 4-(2-Aminothiazol-4-yl)-4-phenylpiperidine p-toluenesulfonate Monohydrate

A mixture of 7.26 g of the compound obtained in the previous step, 1.52 g of thiourea and 150 ml of EtOH is refluxed for 3 hours. The reaction mixture is concentrated under vacuum, the residue is taken up with water and rendered alkaline to pH 13 by the addition of 10% NaOH solution and the precipitate formed is filtered off and washed with water and then with ether to give 4.46 g of the expected product in the form of the free base after recrystallization from EtOH. 1 g of the base is dissolved in acetone and 0.73 g of p-toluenesulfonic acid mono-hydrate is added to give 1.5 g of the expected product in the form of crystals, m.p.=220–222° C.

PREPARATION 1.5

4-Acetyl-4-benzylpiperidine Hydrochloride

A) 4-Cyanopiperidine 25 g of isonipecotamide (or piperidine-4-carboxamide) are added in small portions to 70 ml of $POCl_3$ and the reaction mixture is refluxed for 4 hours. It is concentrated under vacuum, the residue is taken up with ice, rendered alkaline to pH 13 by the addition of concentrated NaOH solution and extracted with DCM and then 4 times with ether, the combined organic phases are dried over $MgSO_4$ and the solvents are evaporated off under vacuum. The oil obtained is distilled under reduced pressure to give 6.4 g of the expected product, b.p.=108–110° C. under 18 mm of mercury.

B) 4-Cyano-1,4-dibenzylpiperidine

A solution of 15 g of the compound obtained in the previous step in 250 ml of THF is cooled to −50° C., 190 ml of a 1.5 M solution of lithium diisopropylamide in cyclohexane are added dropwise and the mixture is stirred for 30 minutes at −50° C. 34 ml of benzyl bromide are then added and the reaction mixture is stirred, the temperature being allowed to rise to RT. After 3 hours at RT, it is poured into a mixture of ice and concentrated HCl, ether is added and the precipitate formed is filtered off and washed with water. The precipitate is taken up with water, rendered alkaline to pH 13 by the addition of concentrated NaOH solution and extracted with ether, the organic phase is dried over $MgSO_4$ and the solvent is evaporated off under vacuum to give 31.7 g of the expected product after crystallization from pentane, m.p.= 92° C.

C) 4-Acetyl-1,4-dibenzylpiperidine Hydrochloride 55 ml of a 1.6 M solution of methyllithium in ether are added to a solution of 20 g of the compound obtained in the previous step in 400 ml of ether and the reaction mixture is stirred for 3 hours at RT. It is poured into iced water, the resulting mixture is decanted, the organic phase is dried over $MgSO_4$ and the solvent is evaporated off under vacuum. The residue is taken up with 400 ml of water, 40 ml of concentrated HCl are added and the mixture is refluxed for 2 hours. After one night at RT, the crystalline product formed is filtered off and washed with a small amount of acetone and then with ether to give 17.6 g of the expected product after drying, m.p.=246° C.

D) 4-Acetyl-4-benzylpiperidine Hydrochloride

A mixture of 3 g of the compound obtained in the previous step, 0.3 g of 10% palladium on charcoal, 50 ml of EtOH and 10 ml of water is hydrogenated at RT and at atmospheric pressure. The catalyst is filtered off and the filtrate is evaporated under vacuum to give 1.8 g of the expected product after crystallization from acetone, m.p.=195° C.

PREPARATION 1.6

4-(Acetylamino)-4-benzylpiperidine p-toluenesulfonate

A) 1,4-Dibenzyl-4-carboxypiperidine 6 g of the compound obtained in step B of PREPARATION 1.5 are added to a solution of 25 ml of water, 25 ml of concentrated $H_2SO_4$ and 25 ml of AcOH and the reaction mixture is heated at 140° C. for 5 hours. After cooling, it is poured onto ice, the pH is brought to 6.5 by the addition of concentrated NaOH solution and the mixture is stirred until crystallization takes place. The crystalline product is filtered off and washed with water. The product is taken up with MeOH, filtered off and washed with ether to give 3 g of the expected product, m.p.=262° C.

B) 1,4-Dibenzyl-4-isocyanatopiperidine

A mixture of 2 g of the compound obtained in the previous step and 1.6 g of phosphorus pentachloride in 40 ml of chloroform is heated at 60° C. for 1 hour. The reaction mixture is concentrated under vacuum, the residue is taken up with 40 ml of acetone, a solution of 2 g of sodium azide in 5 ml of water is added and the mixture is stirred for 30 minutes at RT. It is concentrated under vacuum at RT, the residue is taken up with ether, the organic phase is washed with saturated $Na_2CO_3$ solution and with water and dried over $MgSO_4$ and the solvent is evaporated off under vacuum. The residue is taken up with 40 ml of toluene and refluxed for 1 hour. It is concentrated under vacuum to give 2 g of the expected product in the form of an oil.

C) 4-Amino-1,4-dibenzylpiperidine Hihydrochloride

A mixture of 1 g of the compound obtained in the previous step and 20 ml of 8 N HCl is refluxed for 45 minutes. It is concentrated under vacuum and the residue is dissolved in the minimum amount of EtOH and poured into ether. The precipitate formed is filtered off, washed with ether and dried to give 1 g of the expected product, m.p.=199° C. (dec.).

D) 4-Acetylamino-1,4-dibenzylpiperidine 0.23 ml of acetyl chloride is added to a solution of 1 g of the compound obtained in the previous step and 1.4 ml of triethylamine in 20 ml of DCM and the reaction mixture is stirred for 15 minutes at RT. It is washed with water and with saturated $Na_2SO_4$ solution and dried over $MgSO_4$ and the solvent is evaporated off under vacuum to give 0.75 g of the expected product after crystallization from iso ether, m.p.= 134° C.

E) 4-(Acetylamino)-4-benzylpiperidine p-toluenesulfonate

A mixture of 0.746 g of the compound obtained in the previous step, 0.44 g of p-toluenesulfonic acid monohydrate, 0.2 g of 10% palladium on charcoal and 30 ml of EtOH is stirred for 48 hours under a hydrogen atmosphere. The catalyst is filtered off and the filtrate is concentrated under vacuum to give 0.88 g of the expected product in the form of a foam.

PREPARATION 1.7

4-Benzyl-4-cyanopiperidine

A) 4-Cyano-1-tritylpiperidine

A solution of 6.4 g of the compound obtained in step A of PREPARATION 1.5 in 60 ml of DCM is cooled to 5° C., 10.8 ml of triethylamine are added, 18 g of trityl chloride are then added slowly and the reaction mixture is stirred, the temperature being allowed to rise to RT. It is washed with water and with a buffer solution of pH 2, the organic phase is dried over $MgSO_4$ and the solvent is evaporated off under vacuum to give 19 g of the expected product after crystallization from iso ether, m.p.=206° C.

B) 4-Benzyl-4-cyano-1-tritylpiperidine

A solution of 5 g of the compound obtained in the previous step in 50 ml of THF is cooled to −50° C., 9.5 ml of a 1.5 M solution of lithium diisopropylamide in cyclohexane are added dropwise and the mixture is stirred for 30 minutes at −50° C. 1.7 ml of benzyl bromide are then added and the reaction mixture is stirred for 30 minutes. It is poured into a mixture of ice and a buffer solution of pH 2 and extracted with ether, the extract is washed with saturated NaCl solution and dried over $MgSO_4$ and the solvent is evaporated off under vacuum to give 5.69 g of the expected product after crystallization from iso ether.

C) 4-Benzyl-4-cyanopiperidine

A mixture of 5.7 g of the compound obtained in the previous step, 25 ml of formic acid and 25 ml of water is heated at 60° C. for 1 hour. After cooling to RT, the insoluble material is filtered off and washed with water and the filtrate is evaporated under vacuum. The residue is taken up with water, rendered alkaline to pH 13 by the addition of concentrated NaOH solution and extracted with ether, the organic phase is dried over $MgSO_4$ and the solvent is evaporated off under vacuum to give 2.5 g of the expected product.

PREPARATION 1.8

4-Benzyl-4-(ethoxycarbonylamino)piperidine p-toluenesulfonate

A) 1,4-Dibenzyl-4-(ethoxycarbonylamino)piperidine p-toluenesulfonate

A mixture of 1 g of the compound obtained in step B of PREPARATION 1.6 and 20 ml of EtOH is refluxed for 24 hours. It is concentrated under vacuum, the oil obtained is dissolved in 5 ml of acetone, 0.55 g of para-toluenesulfonic acid monohydrate is added and ether is then added until crystallization takes place. The crystals formed are filtered off, washed with ether and dried to give 1.38 g of the expected product, m.p.=154° C.

B) 4-Benzyl-4-(ethoxycarbonylamino)piperidine p-toluenesulfonate

A mixture of 1.3 g of the compound obtained in the previous step, 0.15 g of 10% palladium on charcoal and 20 ml of EtOH is stirred for 24 hours under a hydrogen atmosphere. The catalyst is filtered off and the filtrate is concentrated under vacuum to give 1 g of the expected product in the form of a foam.

PREPARATION 1.9

4-Benzyl-4-(pyrrolidin-1-ylcarbonyl)piperidine p-toluenesulfonate

A) 1,4-Dibenzyl-4-(pyrrolidin-1-ylcarbonyl)piperidine 0.5 g of pyrrolidine and then 3.8 g of BOP are added to a solution of 2.2 g of the compound obtained in step A of PREPARATION 1.6 and 2.5 ml of triethylamine in 50 ml of DCM and the reaction mixture is stirred for 1 hour at RT. It is concentrated under vacuum, the residue is extracted with AcOEt, the organic phase is washed with water, with 1 N NaOH solution, with water and with saturated NaCl solution and dried over $MgSO_4$ and the solvent is evaporated off under vacuum. The residue is chromatographed on silica using DCM and then a DCM/MeOH mixture (90/10; v/v) as the eluent. The product obtained is taken up with an ether/1 N HCl mixture, the resulting mixture is decanted, the aqueous phase is rendered alkaline to pH 13 by the addition of 1 N NaOH and extracted with DCM, the organic phase is dried over $MgSO_4$ and the solvent is evaporated off under vacuum to give 0.64 g of the expected product after crystallization from iso ether, m.p.=129° C.

B) 4-Benzyl-4-pyrrolidin-1-ylcarbonyl)piperidine p-toluenesulfonate

A mixture of 0.64 g of the compound obtained in the previous step, 0.33 g of p-toluenesulfonic acid monohydrate, 0.1 g of 10% palladium on charcoal and 10 ml of EtOH is hydrogenated at RT and at atmospheric pressure. The catalyst is filtered off and the filtrate is evaporated under vacuum to give 0.75 g of the expected product in the form of a foam.

PREPARATION 1.10

4-(Acetyl-N-methylamino)-4-phenylpiperidine p-toluenesulfonate

A) 4-(Acetyl-N-methylamino)-1-benzyl-4-phenylpiperidine

A solution of 30 g of the compound obtained in step E of PREPARATION 1.3 and 16.5 ml of triethylamine in 300 ml of DCM is cooled to 0–5° C., 8 ml of acetyl chloride are added dropwise and the reaction mixture is stirred for 30 minutes at RT. It is washed twice with water and with 2 N NaOH solution, the organic phase is dried over $MgSO_4$ and the solvent is evaporated off under vacuum to give 31.6 g of the expected product after crystallization from an iso ether/ pentane mixture, m.p.=104° C.

B) 4-(Acetyl-N-methylamino)-4-phenylpiperidine p-toluenesulfonate

A mixture of 5 g of the compound obtained in the previous step, 2.9 g of p-toluenesulfonic acid monohydrate, 0.5 g of 10% palladium on charcoal and 80 ml of EtOH is hydrogenated for 3 hours at 25° C. and at atmospheric pressure. The catalyst is filtered off and the filtrate is concentrated under vacuum to give 5.7 g of the expected product after crystallization from acetone, m.p.=165° C.

PREPARATION 1.11

4-Phenyl-4-(pyrrolidin-1-ylcarbonyl)piperidine Hemihydrate

A) 1-tert-Butoxycarbonyl-4-carboxy-4-phenylpiperidine 30 ml of water and 32.9 g of $K_2CO_3$ are added to a mixture of 30 g of 4-carboxy-4-phenylpiperidine p-toluenesulfonate and 300 ml of dioxane, the resulting mixture is then heated to 60° C. and 18.2 g of di-tert-butyl dicarbonate are added dropwise. The reaction mixture is subsequently heated for 2 hours at 60° C. and then for 30 minutes under reflux. After cooling to RT, it is concentrated under vacuum, the residue is extracted with DCM, the organic phase is washed with a buffer solution of pH 2, acidified to pH 4 by the addition of 2 N HCl, washed with a buffer solution of pH 2, with water and with saturated NaCl solution and dried over $MgSO_4$ and the solvent is evaporated off under vacuum to give 23.7 g of the expected product.

B) 1-tert-Butoxycarbonyl-4-(pyrrolidin-1-ylcarbonyl)-4-phenylpiperidine 9.29 g of triethylamine and then 3.27 g of pyrrolidine are added to a solution of 14 g of the compound obtained in the previous step in 200 ml of DCM. The mixture is cooled in an ice bath, 22.4 g of BOP are added and the reaction mixture is stirred, the temperature being allowed to rise to RT. It is concentrated under vacuum, the residue is extracted with DCM, the organic phase is washed with water, three times with 10% NaOH solution, with water, three times with a buffer solution of pH 2, with water and with saturated NaCl solution and dried over $MgSO_4$ and the solvent is evaporated off under vacuum to give 16.4 g of the expected product.

C) 4-Phenyl-4-(pyrrolidin-1-ylcarbonyl)piperidine Hemihydrate

Concentrated HCl solution is added to a solution of 16.4 g of the compound obtained in the previous step in 200 ml of MeOH until the pH is 1, and the reaction mixture is stirred for 5 hours at RT. It is concentrated under vacuum, the residue is taken up with acetone and the solvent is evaporated off under vacuum to give a white solid, which is recrystallized from propan-2-ol. The product obtained is taken up with 10% NaOH solution and extracted with DCM, the organic phase is washed with 10% NaOH solution and with saturated NaCl solution and dried over $MgSO_4$ and the solvent is evaporated off under vacuum to give 7 g of the expected product after crystallization from ether, m.p.=126° C.

PREPARATION 1.12

4-(N,N-Dimethylaminocarbonyl)-4-phenylpiperidine

A) 1-tert-Butoxycarbonyl-4-(N,N-dimethylaminocarbonyl)-4-phenylpiperidine 8.1 g of triethylamine and then 4.9 g of dimethylamine hydrochloride are added to a solution of 6.11 g of the compound obtained in step A of PREPARATION 1.11 in 20 ml of DCM and 20 ml of DMF. The mixture is cooled in an ice bath, 9.73 g of BOP are added and the resulting mixture is stirred for 3 hours, the temperature being allowed to rise to RT. It is concentrated under vacuum, the residue is extracted with ether, the organic phase is washed with water, with a buffer solution of pH 2, with 10% NaOH solution, with water and with saturated NaCl solution and dried over $MgSO_4$ and the solvent is evaporated off under vacuum to give 6.45 g of the expected product.

B) 4-(N,N-Dimethylaminocarbonyl)-4-phenylpiperidine

Concentrated HCl solution is added to a solution of 6.4 g of the compound obtained in the previous step in 80 ml of MeOH until the pH is 1, and the mixture is stirred for 4 hours at RT. It is concentrated under vacuum, the residue is extracted with DCM, the organic phase is washed three times with 10% NaOH solution and with saturated NaCl solution and dried over $MgSO_4$ and the solvent is evaporated off under vacuum to give 3.2 g of the expected product after crystallization from ether, m.p.=95° C.

PREPARATION 1.13

4-(2-Hydroxyethoxy)-4-phenylpiperidine Hydrochloride

A) 1-Benzyl-4-hydroxy-4-phenylpiperidine

This compound is prepared by reacting phenyllithium with 1-benzylpiperid-4-one by the method described in EP-A-474 561.

B) 4-(Benzoyloxy)-1-benzyl-4-phenylpiperidine

A solution of 2.67 g of the compound prepared in the previous step and 2.5 ml of triethylamine in 30 ml of DCM is cooled to 0–5° C., 1.22 ml of benzoyl chloride are added and the reaction mixture is stirred for 1 hour, the temperature being allowed to rise to RT. It is concentrated under vacuum, the residue is extracted with AcOEt, the organic phase is washed with water and with 1 N NaOH solution and dried over $MgSO_4$ and the solvent is evaporated off under vacuum to give 2.4 g of the expected product after crystallization from pentane.

C) 1-Benzyl-4-(2-hydroxyethoxy)-4-phenylpiperidine Hydrochloride

A mixture of 2.3 g of the compound obtained in the previous step, 7 ml of $H_2SO_4$ and 60 ml of ethylene glycol is heated at 60° C. for 5 hours. The reaction mixture is poured onto ice, rendered alkaline by the addition of concentrated $NH_4OH$ solution and extracted with DCM, the organic phase is washed with water and dried over $MgSO_4$ and the solvent is evaporated off under vacuum. The residue is chromatographed on silica using DCM and then a DCM/MeOH mixture (96/4; v/v) as the eluent. The product obtained is dissolved in DCM and acidified to pH 1 by the addition of ethereal hydrogen chloride and the precipitate formed is filtered off to give 1 g of the expected product.

D) 4-(2-Hydroxyethoxy)-4-phenylpiperidine Hydrochloride

A mixture of 3.3 g of the compound obtained in the previous step, 0.4 g of 10% palladium on charcoal and 100 ml of EtOH is hydrogenated at RT and at atmospheric pressure. The catalyst is filtered off on Célite® and the filtrate is concentrated under vacuum to give 2.2 g of the expected product, m.p.=168–172° C.

PREPARATION 1.14

4-Amino-4-phenylpiperidine Dibenzenesulfonate 26.95 g of the compound obtained in step C of PREPARATION 1.3 are dissolved in 50 ml of water, rendered alkaline to pH 12 by the addition of concentrated NaOH solution and extracted with DCM, the organic phase is washed with saturated NaCl solution and dried over $Na_2SO_4$ and the solvent is evaporated off under vacuum. The oil obtained is taken up with 300 ml of EtOH, 25 g of benzenesulfonic acid and 2.2 g of 5% palladium on charcoal are added and the mixture is then hydrogenated at 40° C. and at atmospheric pressure. The catalyst is filtered off on Célite and washed with MeOH and the filtrate is concentrated under vacuum. The residue is taken up with acetone and the precipitate formed is filtered off to give 29.7 g of the expected product, m.p.=276–278° C.

PREPARATION 1.15

4-(2-Amino-1,3,4-oxadiazol-5-yl)-4-phenylpiperidine p-toluenesulfonate

A) 1-(Benzyloxycarbonyl)-4-carboxy-4-phenylpiperidine

A mixture of 37.7 g of 4-carboxy-4-phenylpiperidine p-toluenesulfonate, 53.3 g of 30% aqueous NaOH solution and 250 ml of water is cooled to 5° C. A solution of 18 g of benzyl chloroformate in 60 ml of acetone is added rapidly at 5° C. and the reaction mixture is stirred overnight, the temperature being allowed to rise to RT. It is washed twice with ether and, after decantation, the aqueous phase is acidified to pH 1 by the addition of concentrated HCl and then 2 N HCl. The precipitate formed is filtered off, dried, taken up with ether and filtered off again to give 30.6 g of the expected product, m.p.=142–144° C.

B) 1-(Benzyloxycarbonyl)-4-(chloroformyl)-4-phenylpiperidine

A mixture of 17.1 g of the compound obtained in the previous step, 24 g of thionyl chloride and 150 ml of 1,2-dichloroethane is refluxed for 1 hour. It is concentrated under vacuum, the residue is taken up with chloroform and the solvent is evaporated off under vacuum. The residue is taken up with an ether/pentane mixture and the solvents are evaporated off again under vacuum to give 20 g of the expected product in the form of a gum, which is used as such.

C) 1-(Benzyloxycarbonyl)-4-carbazoyl-4-phenylpiperidine

A solution of 16 g of hydrazine monohydrate in 40 ml of EtOH is cooled to −50° C., a solution of 11.44 g of the compound obtained in the previous step in 20 ml of 1,2-dimethoxyethane is added dropwise and the mixture is stirred, the temperature being allowed to rise to RT. It is concentrated under vacuum, the residue is taken up with water and extracted with DCM, the organic phase is washed with water and with saturated NaCl solution and dried over MgSO$_4$ and the solvent is evaporated off under vacuum. The residue is taken up with an EtOH/benzene mixture and the solvents are evaporated off under vacuum to give 11.2 g of the expected product in the form of a gum, which is used as such.

D) 4-(2-Amino-1,3,4-oxadiazol-5-yl)-1-(benzyloxycarbonyl)-4-phenylpiperidine

A solution of 3.39 g of cyanogen bromide in 10 ml of EtOH is added at RT to a solution of 11.2 g of the compound obtained in the previous step in 60 ml of EtOH and the reaction mixture is refluxed for 1 hour. It is concentrated to 50 ml of EtOH and water is then added dropwise until the volume of the reaction mixture is 400 ml. The crystalline product formed is filtered off, washed with water, then with DCM, with AcOEt and with ether to give 8 g of the expected product.

E) 4-(2-Amino-1,3,4-oxadiazol-5-yl)-4-phenylpiperidine p-toluenesulfonate

A mixture of 7.85 g of the compound obtained in the previous step, 3.95 g of p-toluenesulfonic acid monohydrate, 0.8 g of 10% palladium on charcoal, 350 ml of 95° EtOH and 10 ml of water is hydrogenated at 50° C. and at atmospheric pressure. After 3 hours, the catalyst is filtered off on Célite® and the filtrate is concentrated under vacuum. The residue is taken up with acetone and the crystalline product formed is filtered off and washed with acetone and then with ether to give 7.65 g of the expected product, m.p.=183–185° C.

PREPARATION 1.16

4-Carbamoyl-4-(morpholin-4-yl)piperidine

A) 1-Benzyl-4-cyano-4-(morpholin-4-yl)piperidine 2.5 ml of morpholine and then 5.1 g of Na$_2$S$_2$O$_5$ are added to a mixture of 5 g of 1-benzylpiperid-4-one and 1.9 g of potassium cyanide in 50 ml of an EtOH/water mixture (50/50; v/v) and the resulting mixture is heated at 60° C. for 2 hours. A further 2.5 ml of morpholine are added and the reaction mixture is stirred overnight at RT. Water is added and the crystalline product formed is filtered off to give 5.5 g of the expected product.

B) 1-Benzyl-4-carbamoyl-4-(morpholin-4-yl)piperidine

A mixture of 14 g of the compound obtained in the previous step and 50 ml of 95% sulfuric acid is heated at 100° C. for 2 hours. After cooling to RT, the reaction mixture is poured onto 100 g of ice, the pH is brought to 7 by the addition of concentrated NOH solution, the mixture is extracted with DCM, the organic phase is washed with water and dried over Na$_2$SO$_4$ and the solvent is evaporated off under vacuum. The residue is chromatographed on silica H using a DCM/MeOH mixture (100/5; v/v to 100/10; v/v) as the eluent to give 3.4 g of the expected product after crystallization from iso ether.

C) 4-Carbamoyl-4-(morpholin-4-yl)piperidine 3.1 g of ammonium formate and 0.8 g of 5% palladium on charcoal are added to a solution of 3.4 g of the compound obtained in the previous step in 50 ml of MeOH and the mixture is stirred for 2 hours at RT. The catalyst is filtered off on Célite® and the filtrate is evaporated under vacuum to give 2.2 g of the expected product after crystallization from propan-2-ol.

PREPARATIONS 1.17 to 1.21

The following are obtained by carrying out the procedure described in PREPARATION 1.16 and replacing the morpholine in step A with thiomorpholine, azetidine, pyrrolidine, perhydroazepine, di-n-heptylamine and di-n-butylamine:

4-carbamoyl-4-(thiomorpholin-4-yl)piperidine (1.17);
4-carbamoyl-4-(azetidin-1-yl)piperidine (1.18);
4-carbamoyl-4-(perhydroazepin-1-yl)piperidine (1.19);
4-carbamoyl-4-(di-n-heptylamino)piperidine (1.20);
4-carbamoyl-4-(di-n-butylamino)piperidine (1.21).

PREPARATIONS 1.22 to 1.26

The following are obtained by carrying out the procedure described in PREPARATION 1.9, starting from the 1,4-dibenzyl-4-carboxypiperidine obtained in step A of PREPARATION 1.6 and replacing the pyrrolidine with azetidine, piperidine, morpholine, perhydroazepine and 1-methylpiperazine:

4-benzyl-4-(azetidin-1-ylcarbonyl)piperidine p-toluenesulfonate (1.22);
4-benzyl-4-(piperidin-1-ylcarbonyl)piperidine p-toluenesulfonate (1.23);
4-benzyl-4-(morpholin-4-ylcarbonyl)piperidine p-toluenesulfonate (1.24);
4-benzyl-4-(perhydroazepin-1-ylcarbonyl)piperidine p-toluenesulfonate (1.25);
4-benzyl-4-(4-methylpiperazin-1-ylcarbonyl)piperidine p-toluenesulfonate (1.26).

PREPARATIONS 1.27 to 1.31

The following are obtained by carrying out the procedure described in PREPARATION 1.11, steps B and C, and replacing the pyrrolidine in step B with azetidine, piperidine, morpholine, perhydroazepine and 1-methylpiperazine:

4-(azetidin-1-ylcarbonyl)-4-phenylpiperidine (1.27);

4-(piperidin-1-ylcarbonyl)-4-phenylpiperidine (1.28);

4-(morpholin-4-ylcarbonyl)-4-phenylpiperidine (1.29);

4-(perhydroazepin-1-ylcarbonyl)-4-phenylpiperidine (1.30);

4-(4-methylpiperazin-1-ylcarbonyl)-4-phenylpiperidine (1.31).

PREPARATION 1.32

4-(N-Methylcarbamoyl)-4-phenylpiperidine

A) 1-tert-Butoxycarbonyl-4-(N-methylcarbamoyl)-4-phenylpiperidine 1.98 g of triethylamine and then 0.49 g of methylamine hydrochloride are added to a solution of 1.5 g of the compound obtained in step A of PREPARATION 1.11 in 5 ml of DCM and 5 ml of DMF. The mixture is cooled in an ice bath, 2.39 g of BOP are added and the reaction mixture is stirred for 24 hours, the temperature being allowed to rise to RT. It is concentrated under vacuum and the residue is extracted with ether, washed with water and with saturated NaCl solution, dried over $MgSO_4$ and evaporated under vacuum to give 1.4 g of the expected product.

B) 4-(N-Methylcarbamoyl)-4-phenylpiperidine 4 ml of concentrated HCl are added to a solution of 1.4 g of the compound obtained in the previous step in 30 ml of MeOH and the mixture is stirred for 1 hour at RT. It is concentrated under vacuum, the residue is extracted with DCM, washed with water and twice with 10% NaOH solution and dried over $MgSO_4$ and the solvent is evaporated off under vacuum to give 0.6 g of the expected product.

PREPARATION 1.33

4-(N-n-Butylcarbamoyl)-4-phenylpiperidine

A) 1-tert-Butoxycarbonyl-4-(N-n-butylcarbamoyl)-4-phenylpiperidine

This compound is prepared by the procedure described in step A of PREPARATION 1.32, starting from 1.0 g of the compound obtained in step A of PREPARATION 1.11 and 0.24 g of n-butylamine. This gives 1.3 g of the expected product, which is used as such in the next step.

B) 4-(N-n-Butylcarbamoyl)-4-phenylpiperidine

This compound is prepared by the procedure described in step B of PREPARATION 1.32. This gives 0.4 g of the expected product.

PREPARATION 1.34

4-(N,N-Diethylcarbamoyl)-4-phenylpiperidine trifluoroacetate

A) 1-tert-Butoxycarbonyl-4-(N,N-diethylcarbamoyl)-4-phenylpiperidine

This compound is prepared by the procedure described in step A of PREPARATION 1.32, starting from 1.5 g of the compound obtained in step A of PREPARATION 1.11 and 0.8 g of diethylamine hydrochloride. This gives 1.7 g of the expected product.

B) 4-(N,N-Diethylcarbamoyl)-4-phenylpiperidine Trifluoroacetate 1.7 g of the compound obtained in the previous step are dissolved in 20 ml of trifluoroacetic acid and the solution is stirred at RT for 30 minutes. It is concentrated under vacuum, the residue is taken up with ether and the mixture is evaporated under vacuum to give 2.8 g of the expected product in the form of an oil.

PREPARATION 1.35

4-Carbamoyl-4-phenylpiperidine

A) 1-tert-Butoxycarbonyl-4-carbamoyl-4-phenylpiperidine

A solution of 1.5 g of the compound obtained in step A of PREPARATION 1.11, 0.99 g of triethylamine and 2.39 g of BOP in 10 ml of DCM is cooled to $-20°$ C. and ammonia gas is then bubbled into the solution. The temperature is allowed to rise to RT and the reaction mixture is stirred for 2 hours. It is concentrated under vacuum, the residue is extracted with ether, the organic phase is washed with water, with a buffer solution of pH 2, with water, with 10% NaOH solution, with water and with saturated NaCl solution and dried over $MgSO_4$ and the solvent is evaporated off under vacuum to give 1.32 g of the expected product.

B) 4-Carbamoyl-4-phenylpiperidine

This compound is prepared by the procedure described in step B of PREPARATION 1.32, starting from 1.32 g of the compound obtained in the previous step. This gives 0.41 g of the expected product.

PREPARATION 1.36

4-(N-Isopropylcarbamoyl)-4-phenylpiperidine

A) 1-tert-Butoxycarbonyl-4-(N-isopropylcarbamoyl)-4-phenylpiperidine

This compound is prepared by the procedure described in step A of PREPARATION 1.32, starting from 1.5 g of the compound obtained in step A of PREPARATION 1.11 and 0.29 g of isopropylamine. This gives 1.61 g of the expected product.

B) 4-(N-Isopropylcarbamoyl)-4-phenylpiperidine

This compound is prepared by the procedure described in step B of PREPARATION 1.32, starting from 1.61 g of the compound obtained in the previous step. This gives 1.1 g of the expected product.

PREPARATION 2.1

3-(3,4-Dichlorophenyl)-3-(3-hydroxypropyl) piperidine Hydrochloride

A) Methyl 4-cyano-4-(3,4-dichlorophenyl)heptanedioate

In a three-necked flask, 37.2 g of 3,4-dichlorophenylacetonitrile and 34.43 g of methyl acrylate are dissolved in 20 ml of dioxane; 1 ml of DBU is added and the mixture is heated for 2 hours at $60°$ C., evaporated, diluted with 400 ml of ethyl acetate, then washed with dilute HCl and NaCl solution, dried over $MgSO_4$ and evaporated. The expected product is crystallized from 100 ml of ethyl acetate and 100 ml of ether with 100 ml of heptane to give 47 g of product.

B) Methyl 3-[5-(3,4-dichlorophenyl)-2-oxopiperid-5-yl] propionate 40 g of the compound prepared in step A are dissolved in 500 ml of 2-methoxyethanol, 2 g of Raney nickel are added and the mixture is hydrogenated at $40°$ C. under atmospheric pressure for 3 days. It is filtered and evaporated to give the expected product in the form of an oil (39 g).

C) 3-[5-(3,4-Dichlorophenyl)-2-oxopiperid-5-yl]propanoic Acid 17 g of the compound prepared in the previous step are dissolved in 250 ml of methanol, 2.8 g of potassium hydroxide and 10 ml of water are added and the mixture is then refluxed for 2 hours. It is evaporated to dryness and the oil obtained is taken up with 200 ml of water and washed with 100 ml of ethyl acetate. The aqueous phase is acidified with 30% HCl solution and the precipitate formed is then filtered off and dried. It is recrystallized from hot methanol to give 18.3 g of the expected compound.

D) 3-(3,4-Dichlorophenyl)-3-(3-hydroxypropyl)piperidine Hydrochloride 5 g of the compound obtained in the previous step are dissolved in 20 ml of THF, 75 ml of borane (concentration: 1 M in THF) are added and the mixture is refluxed for 24 hours under nitrogen. 25 ml of methanol and 50 ml of 4 N HCl are added, the mixture is stirred for 30 minutes and 40% sodium hydroxide is then added until the pH exceeds 10. The mixture is extracted 3 times with 150 ml of DCM and the organic phase is dried over $MgSO_4$ and evaporated. The residue is dissolved in DCM with a 4 N solution of HCl in ether. After evaporation, a foam is obtained and the expected product (4.5 g) crystallizes from an AcOEt/ether mixture.

PREPARATION 2.2

3-(3,4-Dichlorophenyl)-3-[3-tetrahydropyran-2-yloxy)propyl]perhydroazepine

A) Ethyl 5-cyano-5-(3,4-dichlorophenyl)pentanoate 11.8 g of a 55% dispersion of sodium hydride in oil are suspended in 100 ml of THF and cooled in an ice bath, a solution of 50 g of 3,4-dichlorophenylaceto-nitrile in 50 ml of THF is added dropwise and the reaction mixture is stirred for 3 hours at RT. It is cooled again in an ice bath, a solution of 52.4 g of ethyl 4-bromobutanoate in 50 ml of THF is added dropwise and the mixture is stirred overnight at RT. It is concentrated under vacuum, the residue is taken up with water and extracted with ether, the organic phase is washed with water, with a buffer solution of pH 2, with water and with saturated NaCl solution and dried over $MgSO_4$ and the solvent is evaporated off under vacuum. The residue is chromatographed on silica using toluene and then a toluene/AcOEt mixture (100/5; v/v) as the eluent to give 36.9 g of the expected product.

B) Ethyl 5-cyano-5-(3,4-dichlorophenyl)-8-(tetrahydropyran-2-yloxy)octanoate 5 g of a 55% dispersion of sodium hydride in oil are suspended in 100 ml of DMF and cooled to –20° C., a solution of 25.4 g of 2-(3-bromopropoxy)tetrahydropyran and 34.2 g of the compound obtained in the previous step in 100 ml of DMF is added dropwise and the reaction mixture is stirred overnight at RT. It is concentrated under vacuum, the residue is taken up with a mixture of water and a buffer solution of pH 4 and extracted with AcOEt, the organic phase is washed with a buffer solution of pH 4, with water and with saturated NaCl solution and dried over $MgSO_4$ and the solvent is evaporated off under vacuum. The residue is chromatographed on silica using toluene and then a toluene/AcOEt mixture (100/10; v/v) as the eluent to give 36 g of the expected product.

C) Ethyl 5-(aminomethyl)-5-(3,4-dichlorophenyl)-8-(tetrahydropyran-2-yloxy)-octanoate 30 ml of a saturated solution of ammonia in MeOH and 2 g of Raney® nickel are added to a solution of 16.7 g of the compound obtained in the previous step in 200 ml of MeOH and the mixture is then hydrogenated at 40° C. and at atmospheric pressure. The catalyst is filtered off on Célite® and the filtrate is concentrated under vacuum. The residue is extracted with ether, the organic phase is washed with water and with saturated NaCl solution and dried over $MgSO_4$ and the solvent is evaporated off under vacuum to give 15.1 g of the expected product.

D) 6-(3,4-Dichlorophenyl)-6-[3-(tetrahydropyran-2-yloxy)propyl]perhydroazepin-2-one A solution of 15.1 g of the compound obtained in the previous step in 150 ml of xylene is refluxed for 48 hours. After cooling to RT, the reaction mixture is concentrated under vacuum to give 13.5 g of the expected product.

E) 3-(3,4-Dichlorophenyl)-3-[3-tetrahydropyran-2-yloxy)propyl]perhydroazepine

A solution of 14 g of the compound obtained in the previous step in 200 ml of THF is added dropwise to a suspension of 4 g of lithium aluminum hydride in 100 ml of THF and the mixture is then refluxed for 2 hours. After cooling to RT, 4 ml of water, 12 ml of 10% NaOH solution and 4 ml of water are added in succession. The inorganic salts are filtered off on Célite® and the filtrate is concentrated under vacuum. The residue is extracted with DCM, the organic phase is dried over $MgSO_4$ and the solvent is evaporated off under vacuum to give 13 g of the expected product.

EXAMPLE 1

1-Benzoyl-3-(3,4-dichlorophenyl)-3-[3-[4-(pyrrolidin-1-ylcarbonyl)piperid-1-yl]propyl] piperidine Hydrochloride 1.5 Hydrate A) 1-Benzoyl-3-(3,4-dichlorophenyl)-3-(3-hydroxypropyl) piperidine A solution of 16.22 g of the compound obtained in PREPARATION 2.1 and 18.2 g of triethylamine in 250 ml of DCM is cooled in an ice bath and a solution of 14.06 g of benzoyl chloride in 10 ml of DCM is added dropwise. The mixture is stirred for 1 hour, the temperature being allowed to rise to RT. The excess benzoyl chloride is removed by the addition of MeOH and the reaction mixture is then concentrated under vacuum. The residue is taken up with MeOH and the solvent is evaporated off under vacuum. The residue is extracted with ether, washed with water, with 2 N HCl solution, with 5% $NaHCO_3$ solution and with saturated NaCl solution, dried over $MgSO_4$ and evaporated under vacuum. The 1-benzoyl-3-(3,4-dichlorophenyl)-3-(3-benzoyloxypropyl)piperidine thus obtained as an intermediate is dissolved in 150 ml of MeOH, 10% NaOH solution is added and the mixture is heated for 1 hour at 50–60° C. and concentrated under vacuum. The residue is extracted with ether, washed with water, with 2 N HCl solution, with 5% $NaHCO_3$ solution and with saturated NaCl solution and dried over $MgSO_4$ and the solvent is evaporated off under vacuum to give 18 g of the expected product in the form of an oil.

B) 1-Benzoyl-3-(3,4-dichlorophenyl)-3-[3-methanesulfonyloxy)propyl]piperidine

A solution of 16.8 g of the compound obtained in the previous step and 5.18 g of triethylamine in 100 ml of DCM is cooled in an ice bath, a solution of 5.40 g of methanesulfonyl chloride in 10 ml of DCM is added dropwise and the mixture is then stirred for 30 minutes, the temperature being allowed to rise to RT. It is concentrated under vacuum, the residue is extracted with AcOEt, washed with water, with 2 N HCl solution and with saturated NaCl solution and dried over $MgSO_4$ and the solvent is evaporated off under vacuum to give 19.6 g of the expected product in the form of an oil.

Proton NMR spectrum at 200 MHz in DMSO-$d_6$
1 to 2.35 ppm: us: 8H
3.15 ppm: s: 3H
3.2 to 4.6 ppm: us: 6H
6.8 to 7.8 ppm us: 8H C) 1-Benzoyl-3-(3,4-dichlorophenyl)-3-[3-[4-pyrrolidin-1-ylcarbonyl)piperid-1-yl]propyl]piperidine Hydrochloride 1.5 Hydrate 0.56 g of 4-(pyrrolidin-1-ylcarbonyl)piperidine hydrochloride is dissolved in water, the solution is rendered alkaline by the addition of 10% NaOH solution and extracted with DCM, the organic phase is washed with saturated NaCl solution and dried over $MgSO_4$ and the solvent is evaporated off under vacuum. The residue is taken up with 5 ml of DMF and 5 ml of acetonitrile, 1 g of the compound obtained in the previous step and then 0.88 g of $K_2CO_3$ are added and the reaction mixture is heated at 100° C. for 4 hours. It is concentrated under vacuum, the residue is taken up with water and extracted with AcOEt, the organic phase is washed with water and with saturated NaCl solution and dried over $MgSO_4$ and the solvent is evaporated off under vacuum. The residue is chromatographed on silica H using DCM and then a DCM/MeOH mixture (95/5; v/v) as the eluent. The product obtained is taken up with AcOEt and acidified by the addition of ethereal hydrogen chloride and the precipitate formed is filtered off to give 0.8 g of the expected product, m.p.=146° C.

EXAMPLE 2

1-Benzoyl-3-(3,4-dichlorophenyl)-3-[3-(4-piperidinopiperid-1-yl)propyl]-piperidine Dihydrochloride Hemihydrate A mixture of 0.55 g of 4-piperidinopiperidine, 1.3 g of the compound obtained in step B of EXAMPLE 1 and 1.14 g of $K_2CO_3$ in 10 ml of a DMF/acetonitrile mixture (50/50; v/v) is heated at 100° C. for 3 hours. The reaction mixture is poured into water and extracted with AcOEt, the organic phase is washed twice with water and with saturated NaCl solution and dried over $MgSO_4$ and the solvent is evaporated off under vacuum. The residue is chromatographed on silica H using DCM and then a DCM/MeOH mixture (98/2; v/v) as the eluent. The product obtained is dissolved in AcOEt, a stream of HCl gas is bubbled into the solution until the pH is 1, and ether is added until precipitation occurs. This gives 0.53 g of the expected product after filtration and drying, m.p.=265° C. (dec.).

EXAMPLE 3

1-Benzoyl-3-(3,4-dichlorophenyl)-[3-[4-carbamoyl-4-(piperid-1-yl)piperid-1-yl]propyl]piperidine Dihydrochloride 1.5 Hydrate 2.6 g of 4-carbamoyl-4-(piperid-1-yl)piperidine dihydrochloride are dissolved in water, the solution is rendered alkaline by the addition of concentrated NaOH solution and extracted with DCM, the extract is dried over $MgSO_4$ and the solvent is evaporated off under vacuum. The residue is taken up with 10 ml of acetonitrile, 1.55 g of the compound obtained in step B of EXAMPLE 1 are added and the reaction mixture is refluxed for 2 hours. It is concentrated under vacuum, the residue is extracted with AcOEt, the organic phase is washed with water, with 1 N NaOH solution and with saturated NaCl solution and dried over $MgSO_4$ and the solvent is evaporated off under vacuum. The residue is chromatographed on silica H using a gradient of a DCM/MeOH mixture (99/1; v/v to 93/7; v/v) as the eluent. The product obtained is taken up with DCM and acidified by the addition of ethereal hydrogen chloride and the mixture is evaporated under vacuum to give 2 g of the expected product, m.p.=210° C.

EXAMPLE 4

3-[3-[4-(Acryloyl-N-methylamino)-4-phenylpiperid-1-yl]propyl]-1-benzoyl-3-(3,4-dichlorophenyl) piperidine Hydrochloride A mixture of 0.27 g of 4-(acryloyl-N-methylamino)-4-phenylpiperidine hydrochloride, 0.45 g of the compound obtained in step B of EXAMPLE 1 and 0.3 g of $K_2CO_3$ in 3 ml of DMF is heated at 80° C. for 2 hours. The reaction mixture is poured into water and extracted with AcOEt, the organic phase is washed with water and with saturated NaCl solution and dried over $MgSO_4$ and the solvent is evaporated off under vacuum. The residue is chromatographed on silica using a gradient of a DCM/MeOH mixture (99/1; v/v to 95/5; v/v) as the eluent. The product obtained is dissolved in DCM and acidified by the addition of ethereal hydrogen chloride and the precipitate formed is filtered off to give 0.2 g of the expected product, m.p.=128° C.

EXAMPLE 5

3-[3-[4-(2-Aminothiazol-4-yl)-4-phenylpiperid-1-yl] propyl]-1-benzoyl-3-(3,4-dichlorophenyl)piperidine Dihydrochloride Monohydrate A mixture of 1.04 g of 4-(2-aminothiazol-4-yl)-4-phenylpiperidine (compound of PREPARATION 1.4 in the form of the free base), 1.88 g of the compound obtained in step B of EXAMPLE 1 and 1.1 g of $K_2CO_3$ in 20 ml of a DMF/acetonitrile mixture (50/50; v/v) is refluxed for 2 hours. The reaction mixture is concentrated under vacuum, the residue is taken up with water and extracted with AcOEt, the organic phase is washed with water and dried over $MgSO_4$ and the solvent is evaporated off under vacuum. The residue is chromatographed on silica using a gradient of a DCM/MeOH mixture (98/2; v/v to 95/5; v/v) as the eluent. The product obtained is taken up with ethereal hydrogen chloride and the precipitate formed is filtered off to give 1.2 g of the expected product after crystallization from AcOEt, m.p.=162–164° C.

EXAMPLE 6

3-[3-(4-Acetyl-4-benzylpiperid-1-yl)propyl]-1-benzoyl-3-(3,4-dichlorophenyl)piperidine Hydrochloride Hemihydrate 1.2 g of 4-acetyl-4-benzylpiperidine hydrochloride are dissolved in the minimum amount of water, the solution is rendered alkaline to pH 13 by the addition of concentrated NaOH solution and extracted with ether and the organic phase is dried over $MgSO_4$ and filtered. 1 g of the compound obtained in step B of EXAMPLE 1 is added to the filtrate and the mixture is concentrated under vacuum. The residue is taken up with 5 ml of DMF and heated at 70° C. for 3 hours. The reaction mixture is poured into iced water and extracted with ether, the organic phase is washed with water and with saturated NaCl solution and dried over $MgSO_4$ and the solvent is evaporated off under vacuum. The residue is chromatographed on silica H using DCM and then a DCM/MeOH mixture (95/5; v/v) as the eluent. The product obtained is taken up with DCM and acidified to pH 1 by the addition of ethereal hydrogen chloride and the mixture is evaporated under vacuum to give 0.84 g of the expected product after crystallization from iso ether.

Proton NMR spectrum at 200 MHz in DMSO-$d_6$
0.9 to 2.4 ppm: us: 15H
2.5 to 4.6 ppm: us: 12H
6.8 to 7.9 ppm: us: 13H
9.9 to 10.6 ppm: 2 bs: 1H

EXAMPLE 7

3-[3-[4-(Acetylamino)-4-benzylpiperid-1-yl]propyl]-1-benzoyl-3-(3,4-dichlorophenyl)piperidine Hydrochloride Dihydrate A mixture of 0.44 g of 4-(acetylamino)-4-benzylpiperidine p-toluene-sulfonate, 0.50 g of the compound obtained in step B of EXAMPLE 1 and 0.53 g of K$_2$CO$_3$ in 5 ml of DMF is heated at 90° C. for 2 hours. The reaction mixture is poured into water and extracted with AcOEt, the organic phase is washed with 2 N NaOH and with saturated NaCl solution and dried over MgSO$_4$ and the solvent is evaporated off under vacuum. The residue is chromatographed on silica H using a gradient of a DCM/MeOH mixture (99/1; v/v to 93/7; v/v) as the eluent. The product obtained is dissolved in DCM and acidified by the addition of ethereal hydrogen chloride and the precipitate formed is filtered off to give 0.38 g of the expected product, m.p=158° C. (dec.).

EXAMPLE 8

1-Benzoyl-3-[3-(4-benzyl-4-cyanopiperid-1-yl) propyl]-3-(3,4-dichloro-phenyl)piperidine Hydrochloride Monohydrate This compound is prepared by the procedure described in EXAMPLE 4, starting from 2.5 g of 4-benzyl-4-cyanopiperidine, 5 g of the compound obtained in step B of EXAMPLE 1, 3.7 g of K$_2$CO$_3$ and 50 ml of DMF. The product obtained is chromatographed on silica H using DCM and then a DCM/MeOH mixture (97/3; v/v) as the eluent. The product obtained is taken up with ethereal hydrogen chloride and the solvent is evaporated off under vacuum to give 2.8 g of the expected product after crystallization from iso ether.

EXAMPLE 9

3-[3-[4-(Aminomethyl)-4-benzylpiperid-1-yl] propyl]-1-benzoyl-3-(3,4-dichlorophenyl)piperidine Dihydrochloride Hemihydrate A mixture of 2.3 g of the compound obtained in EXAMPLE 8 and 0.3 g of Raney® nickel in 100 ml of EtOH is hydrogenated for 72 hours at RT and at atmospheric pressure. The catalyst is filtered off and the filtrate is concentrated under vacuum. The residue is chromatographed on silica H using DCM and then a DCM/MeOH mixture (85/15; v/v) as the eluent. The product obtained is taken up with ethereal hydrogen chloride and the precipitate formed is filtered off to give 1.08 g of the expected product.

Proton NMR spectrum at 200 MHz in DMSO-d$_6$
0.8 to 2.3 ppm: us: 12H
2.6 to 4.5 ppm: us: 14H
6.9 to 8.0 ppm: us: 13H
8.4 ppm:bs:3H

EXAMPLE 10

1-Benzoyl-3-[3-[4-benzyl-4-(propionylaminomethyl) piperid-1-yl]propyl]-3-(3,4-dichlorophenyl) piperidine Hydrochloride A solution of 0.6 g of the compound obtained in EXAMPLE 9 and 0.18 ml of triethylamine in 10 ml of DCM is cooled to 0° C., 0.1 ml of propionyl chloride is added dropwise and the mixture is stirred for 5 minutes. It is concentrated under vacuum, the residue is extracted with AcOEt, the organic phase is washed twice with water and dried over MgSO$_4$ and the solvent is evaporated off under vacuum. The residue is chromatographed on silica H using DCM and then a DCM/MeOH mixture (9515; v/v) as the eluent. The product obtained is taken up with ethereal hydrogen chloride and the precipitate formed is filtered off to give 0.37 g of the expected product.

Proton NMR spectrum at 200 MHz in DMSO-d6
0.7 to 2.3 ppm: us: 17H
2.55 to 4.5 ppm: us: 14H
6.8 to 8.0 ppm: us: 14H
9.0to 10 ppm:2bs: 1H

EXAMPLE 11

1-Benzoyl-3-[3-[4-benzyl-4-(ethoxycarbonylamino) piperid-1-yl]propyl]-3-(3,4-dichlorophenyl) piperidine Hydrochloride Hemihydrate This compound is prepared by the procedure described in EXAMPLE 7, starting from 0.5 g of 4-benzyl-4-(ethoxycarbonylamino)piperidine p-toluene-sulfonate, 0.5 g of the compound obtained in step B of EXAMPLE 1 and 0.52 g of K$_2$CO$_3$ in 5 ml of DMF. This gives 0.32 g of the expected product, m.p.=142° C. (dec.).

EXAMPLE 12

1-Benzoyl-3-[3-[4-benzyl-4-(pyrrolidin-1-ylcarbonyl)piperid-1-yl]propyl]-3-(3,4-dichlorophenyl)piperidine Hydrochloride Hemihydrate A mixture of 4-benzyl-4-(pyrrolidin-1-ylcarbonyl) piperidine p-toluene-sulfonate, 0.65 g of the compound obtained in step B of EXAMPLE 1 and 0.7 g of K$_2$CO$_3$ in 6 ml of DMF is heated at 80° C. for 3 hours. The reaction mixture is poured into iced water and the precipitate formed is filtered off and washed with water. The precipitate is dissolved in AcOEt, the organic phase is dried over MgSO$_4$ and the solvent is evaporated off under vacuum. The residue is chromatographed on silica H using DCM and then a DCM/MeOH mixture (95/5; v/v) as the eluent. The product obtained is taken up with ethereal hydrogen chloride and the precipitate formed is filtered off to give 0.56 g of the expected product.

Proton NMR spectrum at 200 MHz in DMSO-d$_6$
0.9 to 2.45 ppm: us: 16H
2.5 to 4.6 ppm: us: 16H
6.8 to 7.8 ppm: us: 13H
9.9 to 10.6 ppm: rs: 1H

EXAMPLE 13

3-[3-[4-(Acetyl-N-methylamino)-4-phenylpiperid-1-yl]propyl]-1-benzoyl-3-(3,4-dichlorophenyl) perhydroazepine Hydrochloride 0.3 Hydrate A) 1-Benzoyl-3-(3,4-dichlorophenyl)-3-[3-(tetrahydropyran-2-yloxy)propyl]-perhydroazepine A solution of 13 g of the compound obtained in PREPARATION 2.2 and 6.8 g of triethylamine in 200 ml of DCM is cooled in an ice bath, a solution of 4.96 g of benzoyl chloride in 30 ml of DCM is added dropwise and the reaction mixture is stirred for 5 minutes. It is concentrated under vacuum, the residue is taken up with water and extracted with AcOEt, the organic phase is washed with water, with 5% NaHCO$_3$ solution, with water and with saturated NaCl solution and dried over MgSO$_4$ and the solvent is evaporated off under vacuum to give 16.5 g of the expected product.

B) 1-Benzoyl-3-(3,4-dichlorophenyl)-3-(3-hydroxypropyl) perhydroazepine

A stream of HCl gas is bubbled into a solution of 16.5 g of the compound obtained in the previous step in 200 ml of MeOH until the pH is <1, and the reaction mixture is stirred for 10 minutes. It is concentrated under vacuum, the residue is taken up with a saturated solution of HCl gas in MeOH and the solvent is evaporated off under vacuum. The residue is extracted with DCM, the organic phase is washed with 5% NaHCO₃ solution and with saturated NaCl solution and dried over MgSO₄ and the solvent is evaporated off under vacuum to give 13.7 g of the expected product.

C) 1-Benzoyl-3-(3,4-dichlorophenyl)-3-[3-methanesulfonyloxy)propyl]-perhydroazepine A solution of 5 g of the compound obtained in the previous step and 1.5 g of triethylamine in 100 ml of DCM is cooled in an ice bath, a solution of 1.55 g of methanesulfonyl chloride in 20 ml of DCM is added dropwise and the mixture is stirred for 5 minutes. It is concentrated under vacuum, the residue is taken up with water and extracted with AcOEt, the organic phase is washed with water, with 5% NaHCO₃ solution, with water and with saturated NaCl solution and dried over MgSO₄ and the solvent is evaporated off under vacuum to give 5.7 g of the expected product.

D) 3-[3-[4-(Acetyl-N-methylamino)-4-phenylpiperid-1-yl]propyl]-1-benzoyl-3-(3,4-dichlorophenyl)perhydroazepine Hydrochloride 0.3 Hydrate A mixture of 1.2 g of 4-(acetyl-N-methylamino)-4-phenylpiperidine p-toluenesulfonate, 1.2 g of the compound obtained in the previous step and 1.2 g of K₂CO₃ in 20 ml of a DMF/acetonitrile mixture (50150; v/v) is refluxed for 3 hours. After cooling to RT, the reaction mixture is poured into water and extracted with AcOEt, the organic phase is washed three times with water and with saturated NaCl solution and dried over MgSO₄ and the solvent is evaporated off under vacuum. The residue is chromatographed on silica using DMC and then a DCM/MeOH mixture (96/4; v/v) as the eluent. The product obtained is taken up with ethereal hydrogen chloride and the solvent is evaporated off under vacuum to give 0.63 g of the expected product after solidification in ether, m.p.=125° C.

EXAMPLE 14

1-Benzoyl-3-(3,4-dichlorophenyl)-3-[3-[4-(N,N-dimethylaminocarbonyl)-4-phenylpiperid-1-yl]propyl]perhydroazepine Hydrochloride Hemihydrate This compound is prepared by the procedure described in step D of EXAMPLE 13, starting from 0.69 g of 4-(N,N-dimethylaminocarbonyl)-4-phenyl-piperidine, 1.2 g of the compound obtained in step C of EXAMPLE 13 and 1.2 g of K₂CO₃ in 20 ml of a DMF/acetonitrile mixture (50/50; v/v). This gives 0.65 g of the expected product, m.p.=150° C.

EXAMPLE 15

1-Benzoyl-3-(3,4-dichlorophenyl)-3-[3-[4-phenyl-4-(pyrrolidin-1-yl-carbonyl)piperid-1-yl]propyl]perhydroazepine Hydrochloride Hemihydrate This compound is prepared by the procedure described in step D of EXAMPLE 13, starting from 0.96 g of 4-phenyl-4-(pyrrolidin-1-ylcarbonyl)-piperidine, 1.5 g of the compound obtained in step C of EXAMPLE 13 and 1.5 g of K₂CO₃ in 10 ml of a DMF/acetonitrile mixture (50/50; v/v). This gives 0.34 g of the expected product, m.p.=135° C.

EXAMPLE 16

3-[3-[4-(2-Aminothiazol-4-yl)-4-phenylpiperid-1-yl]propyl]-1-benzoyl-3-(3,4-dichlorophenyl)perhydroazepine Dihydrochloride 1.5 Hydrate This compound is prepared by the procedure described in step D of EXAMPLE 13, starting from 0.77 g of 4-(2-aminothiazol-4-yl)-4-phenylpiperidine (compound of PREPARATION 1.4 in the form of the free base), 1.2 g of the compound obtained in step C of EXAMPLE 13 and 1.2 g of K₂CO₃ in 20 ml of a DMF/acetonitrile mixture (50/50; v/v). This gives 0.8 g of the expected product after crystallization from AcOEt, m.p.=178° C.

EXAMPLE 17

1-Benzoyl-3-(3,4-dichlorophenyl)-3-[3-[4-(2-hydroxyethoxy)-4-phenyl-piperid-1-yl]propyl]piperidine Hydrochloride Monohydrate A mixture of 1 g of 4-(2-hydroxyethoxy)-4-phenylpiperidine hydrochloride, 1.7 g of the compound obtained in step B of EXAMPLE 1 and 0.65 g of K₂CO₃ in 15 ml of DMF is heated at 60° C. for 2 hours and the reaction mixture is then stirred overnight at RT. It is poured into water and extracted with DCM, the organic phase is washed with water and dried over Na₂SO₄ and the solvent is evaporated off under vacuum. The residue is chromatographed on silica H using DCM and then a DCM/MeOH mixture (96/4; v/v) as the eluent. The product obtained is dissolved in DCM and acidified by the addition of ethereal hydrogen chloride and the precipitate formed is filtered off to give 1.2 g of the expected product, m.p.=120–123° C.

EXAMPLE 18

3-[3-[4-(2-Acetoxyethoxy)-4-phenylpiperid-1-yl]propyl]-1-benzoyl-3-(3,4-dichlorophenyl)piperidine Hydrochloride 1.5 Hydrate A solution of 0.6 g of the compound obtained in EXAMPLE 17 and 0.5 ml of triethylamine in 25 ml of DCM is cooled to 0–5° C., 0.085 ml of acetyl chloride is added and the mixture is stirred for 3 hours, the temperature being allowed to rise to RT. It is concentrated under vacuum, the residue is taken up with water and extracted with AcOEt, the organic phase is washed with water and dried over Na₂SO₄ and the solvent is evaporated off under vacuum. The residue is chromatographed on silica using DCM and then a DCM/MeOH mixture (98/2; v/v) as the eluent. The product obtained is dissolved in DCM and acidified by the addition of ethereal hydrogen chloride and the precipitate formed is filtered off to give 1.2 g of the expected product, m.p.= 105–107° C.

EXAMPLE 19

1-Benzoyl-3-(3,4-dichlorophenyl)-3-[3-[4-(2-furoylamino)-4-phenylpiperid-1-yl]propyl]piperidine Hydrochloride Hemihydrate A) 3-[3-(4-Amino-4-phenylpiperid-1-yl)propyl]-1-benzoyl-3-(3,4-dichlorophenyl)-piperidine A mixture of 6.81 g of 4-amino-4-phenylpiperidine dibenzenesulfonate, 5.2 g of the compound obtained in step B of EXAMPLE 1 and 6.1 g of K₂CO₃ in 30 ml of a DMF/acetonitrile mixture (50/50; v/v) is heated at 100° C. for 5 hours. It is concentrated under vacuum, the residue is taken up with water and extracted with AcOEt, the organic phase is washed with water and with saturated NaCl solution and dried over MgSO₄ and the solvent is evaporated off under vacuum. The residue is chromatographed on silica H using a DCM/MeOH mixture (from 99/1; v/v to 85/15; v/v) as the eluent to give 3.6 g of the expected product.

B) 1-Benzoyl-3-(3,4-dichlorophenyl)-3-[3-[4-(2-furoylamino)-4-phenylpiperid-1-yl]propyl]piperidine Hydrochloride Hemihydrate A solution of 1.5 g of the compound obtained in the previous step and 0.54 g of triethylamine in 10 ml of DCM is cooled to 0–5° C., 0.35 g of 2-furoyl chloride is added and the mixture is stirred for 2 hours 30 minutes, the temperature being allowed to rise to RT. It is concentrated under vacuum, the residue is extracted with DCM, the organic phase is washed with water, with 5% NaHCO₃ solution, with water and with saturated NaCl solution and dried over MgSO₄ and the solvent is evaporated off under vacuum. The residue is chromatographed on silica H using DCM and then a DCM/MeOH mixture (97/3; v/v) as the eluent. The product obtained is dissolved in AcOEt, a stream of HCl gas is bubbled into the solution until the pH is 1, and ether is added until precipitation occurs. This gives 1.27 g of the expected product after filtration and drying, m.p.=180–182° C.

EXAMPLE 20

1-Benzoyl-3-(3,4-dichlorophenyl)-3-[3-[4-(2-thenoylamino)-4-phenyl-piperid-1-yl]propyl]piperidine Hydrochloride Monohydrate This compound is prepared by the procedure described in step B of EXAMPLE 19, starting from 1.5 g of the compound obtained in step A of EXAMPLE 19, 0.55 g of triethylamine and 0.4 g of 2-thenoyl chloride in 10 ml of DCM. The residue is chromatographed on silica H using DCM and then a DCM/MeOH mixture (95/5; v/v) as the eluent. The product obtained is taken up with DCM and acidified to pH I by the addition of ethereal hydrogen chloride and the precipitate obtained is filtered off to give 0.99 g of the expected product, m.p.=198–200° C.

EXAMPLE 21

3-(3,4-Dichlorophenyl)-1-isonicotinoyl-3-[3-[4-phenyl-4-(pyrrolidin-1-ylcarbonyl)piperid-1-yl]propyl]piperidine Dihydrochloride Trihydrate, (+) Isomer (Compound of Formula I"a, Z"=4-Pyridyl)

A) 3-(3,4-Dichlorophenyl)-3-(3-hydroxypropyl)piperidine Hydrochloride, (+) Isomer 5 ml of 40% NaOH solution are added to a solution of 10 g of the compound obtained in PREPARATION 2.1 in 20 ml of water, the mixture is extracted with DCM, the organic phase is dried over MgSO₄ and the solvent is evaporated off under vacuum to give 9 g of an oil. 2.7 g of the oil obtained are dissolved in 50 ml of propan-2-ol, 2.36 g of 10-camphosulfonic acid, (+) isomer, are added and the mixture is heated to the reflux temperature. After cooling, crystallization and filtration of the crystals formed (3.86 g), the latter are dissolved in 10% NaOH solution and extracted with chloroform, the organic phase is dried over MgSO₄ and the solvent is evaporated off under vacuum to give 2.3 g of product in the form of an oil, from which the hydrochloride is prepared. The optical rotation of the hydrochloride is measured.

$[\alpha]_D^{25}$=+5.5° (c=0.1; MeOH)

A second crystallization is carried out using 2.12 g of the oil obtained and 1.84 g of 10-camphosulfonic acid, (+) isomer, in 40 ml of propan-2-ol. After alkalization with NaOH, extraction with chloroform, drying over MgSO₄ and evaporation, 2.1 g of the expected product are obtained in the form of an oil, from which the hydrochloride is prepared.

$[\alpha]_D^{25}$=+6.5° (c=0.1; MeOH)

B) 1-(tert-Butoxycarbonyl)-3-(3,4-dichlorophenyl)-3-(3-hydroxypropyl)piperidine, (+) isomer 0.61 g of di-tert-butyl dicarbonate is added to a solution of 0.9 g of the compound obtained in the previous step and 0.6 g of triethylamine in 100 ml of DCM and the mixture is stirred for 30 minutes at RT. It is concentrated under vacuum, the residue is extracted with AcOEt, the organic phase is washed with a buffer solution of pH 2, with 1 N NaOH solution and with saturated NaCl solution and dried over MgSO₄ and the solvent is evaporated off under vacuum to give 1.1 g of the expected product in the form of an oil.

C) 1-(tert-Butoxycarbonyl)-3-(3,4-dichlorophenyl)-3-[3-(methanesulfonyloxy)-propyl]piperidine, (+) Isomer A solution of 22 g of the compound obtained in the previous step and 6.86 g of triethylamine in 150 ml of DCM is cooled to 0–5° C., 7.13 g of methanesulfonyl chloride are added and the mixture is stirred for 1 hour at 0–5° C. and then for 2 hours at RT. It is concentrated under vacuum, the residue is extracted with AcOEt, the organic phase is washed with water and with saturated NaCl solution and dried over MgSO₄ and the solvent is evaporated off under vacuum. The product obtained is taken up with ether and the mixture is then evaporated under vacuum to give 26.4 g of the expected product in the form of an oil.

D) 1-(tert-Butoxycarbonyl)-3-(3,4-dichlorophenyl)-3-[3-[4-phenyl-4-(pyrrolidin-1-ylcarbonyl)piperid-1-yl]propyl]piperidine, (+) Isomer A mixture of 17 g of 4-phenyl-4-(pyrrolidin-1-ylcarbonyl)piperidine, 25.5 g of the compound obtained in the previous step and 22.7 g of K₂CO₃ in 100 ml of a DMF/acetonitrile mixture (50/50; v/v) is heated at 100° C. for 3 hours 30 minutes. It is concentrated under vacuum, the residue is extracted with AcOEt, the organic phase is washed with water and with saturated NaCl solution and dried over MgSO₄ and the solvent is evaporated off under vacuum. The residue is taken up with pentane and the precipitate formed is filtered off to give 33 g of the expected product, m.p.=133–137° C.

$[\alpha]_D^{20}$=+33.2° (c=0.5; MeOH)

E) 3-(3,4-Dichlorophenyl)-3-[3-[4-phenyl-4-(pyrrolidin-1-ylcarbonyl)piperid-1-yl]propyl]piperidine Dihydrochloride, (+) Isomer Concentrated HCl solution is added to a solution of 25.8 g of the compound obtained in the previous step in 200 ml of MeOH until the pH is 1, and the mixture is heated at 40° C. for 3 hours. It is concentrated under vacuum and the product obtained is crystallized from an AcOEt/ether mixture to give 17 g of the expected product, m.p.=170° C.

$[\alpha]_D^{20}$=+13° (c=0.5; MeOH)

F) 3-(3,4-Dichlorophenyl)-1-isonicotinoyl-3-[3-[4-phenyl-4-(pyrrolidin-1-yl-carbonylpiperid-1-yl]propyl]piperidine Dihydrochloride Trihydrate, (+) Isomer A solution of 1.7 g of the compound obtained in the previous step and 0.9 g of triethylamine in 10 ml of DCM is cooled to 0–5° C., 0.6 g of isonicotinoyl chloride hydrochloride is added and the mixture is stirred for 1 hour at RT. It is concentrated under vacuum, the residue is extracted with AcOEt, the organic phase is washed with water and with saturated NaCl solution and dried over Na₂SO₄ and the solvent is evaporated off under vacuum. The residue is chromatographed on silica H using DCM and then a DCM/MeOH mixture (93/7; v/v) as the eluent. The product obtained is dissolved in AcOEt, a stream of HCl gas is bubbled into the solution until the pH is 1, and ether is added until precipitation occurs. This gives 0.27 g of the expected product after filtration and drying, m.p.=140–142° C.

$[\alpha]_D^{20}$=+11.6° (c=0.5; MeOH)

EXAMPLE 22

1-Benzoyl-3-(3,4-dichlorophenyl)-3-[3-[spiro (indoline-3,4'-piperid-1'-yl)-propyl]piperidine Dihydrochloride 1.5 Hydrate A mixture of 1 g of the compound obtained in step B of EXAMPLE 1, 0.7 g of spiro(indoline-3,4'-piperidine) dihydrochloride and 0.8 g of $K_2CO_3$ in 10 ml of DMF is heated at 70–80° C. for 3 hours. The reaction mixture is poured into water and the precipitate formed is filtered off and dried. The precipitate is chromatographed on silica using DCM and then a DCM/MeOH mixture (94/6; v/v) as the eluent. The product obtained is dissolved in DCM and acidified to pH 1 by the addition of ethereal hydrogen chloride and the precipitate formed is filtered off to give 0.5 g of the expected product, m.p.=192–195° C.

EXAMPLE 23

1-Benzoyl-3-(3,4-dichlorophenyl)-3-[3-[1-acetylspiro(indoline-3,4'-piperid-1'-yl)propyl] piperidine Hydrochloride Monohydrate A mixture of 1 g of the compound obtained in step B of EXAMPLE 1, 1 g of 1-acetylspiro(indoline-3,4'-piperidine) hydrochloride and 0.6 g of $K_2CO_3$ in 10 ml of DMF is heated at 70° C. for 2 hours. The reaction mixture is poured into water and the precipitate formed is filtered off. The precipitate is dissolved in DCM, the organic phase is dried over $MgSO_4$ and the solvent is evaporated off under vacuum. The residue is chromatographed on silica using DCM and then a DCM/MeOH mixture (97/3; v/v) as the eluent. The product obtained is dissolved in DCM and acidified to pH 1 by the addition of ethereal hydrogen chloride and the precipitate formed is filtered off to give 0.7 g of the expected product, m.p.=189–191° C.

The compounds according to the invention collated in TABLE I below are prepared by following the procedure described in step F of EXAMPLE 21, starting from the compound obtained in step E of EXAMPLE 21 and the appropriate acid chlorides.

TABLE I (I'a)

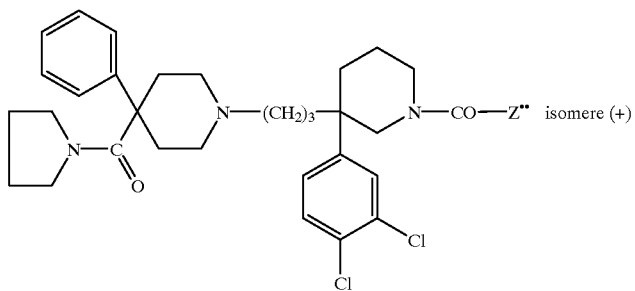

| Example | Z' | Salt, solvate; m.p. °C.; $[\alpha]_D^{20}$ |
|---|---|---|
| 24 | (2-thienyl) | HCl, 1H$_2$O; 134–136; +31° (c = 0.5; MeOH) |
| 25 | (3-thienyl) | HCl, 0.5H$_2$O; 172; +35.6° (c = 0.5; MeOH) |
| 26 | (2-furyl) | HCl, 1.25H$_2$O; 120–122; +47° (c = 0.5; MeOH) |
| 27 | (3-furyl) | HCl, 2H$_2$O; 175; +32.6° (c = 0.5; MeOH) |

The compounds according to the invention collated in TABLE II below are prepared by following the procedures described in the previous EXAMPLES, starting from the compound obtained in step B of EXAMPLE 1 and the piperidines described in the REPARATIONS.

TABLE II (I)

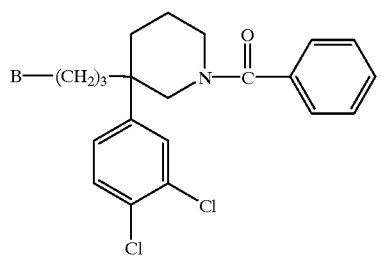

| Example | B- | Salt, solvate; m.p. ° C. or NMR |
|---|---|---|
| 28 (a) | (4-phenyl-1-methylpiperidine linked via 5-amino-1,3,4-oxadiazole) | 2HCl, 2.5H$_2$O; 202–204 |
| 29 (b) | EtO—C(O)—C(O)—HN—(4-phenyl-1-methylpiperidine) | HCl, H$_2$O; 160–162 |
| 30 (a) | (4-morpholino-4-carbamoyl-1-methylpiperidine) | 2HCl, H$_2$O; 165 |
| 31 (c) | MeO—C(O)—N—(spiroindoline-1-methylpiperidine) | HCl, 1.2H$_2$O; 175–180 |
| 32 (c) | Me$_2$N—C(O)—N—(spiroindoline-1-methylpiperidine) | HCl, 0.5H$_2$O; 155–157 |

TABLE II-continued (I)

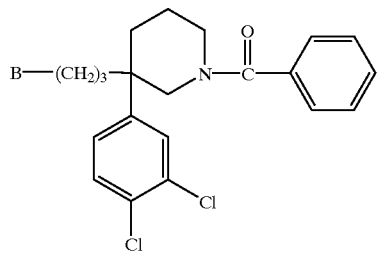

| Example | B- | Salt, solvate; m.p. ° C. or NMR |
|---|---|---|
| 33 (c) | 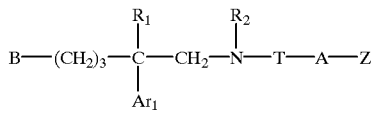 | HCl, 1.3H$_2$O; 158–160 |

(a) This compound is prepared by the procedure described in EXAMPLE 2.
(b) This compound is prepared by the procedure described in step B of EXAMPLE 19, starting from the compound obtained in step A of EXAMPLE 19 and ethyloxalyl chloride.
(c) This compound is prepared by the procedure described in EXAMPLE 23, starting from the compound obtained in step B of EXAMPLE 1 and the appropriate spiro(indoline-3,4'-piperidines).

What is claimed is:

1. A compound of the formula $$B-(CH_2)_3-\underset{\underset{Ar_1}{|}}{\overset{\overset{R_1}{|}}{C}}-CH_2-\underset{}{\overset{\overset{R_2}{|}}{N}}-T-A-Z$$ (I)

in which:

R$_1$ and R$_2$ together form a group —(CH$_2$)$_4$—;

AR$_1$ is a phenyl which is unsubstituted or monosubstituted or polysubstituted by a substituent selected from a halogen atom, a hydroxyl, a (C$_1$-C$_4$)alkoxy, a (C$_1$-C$_4$)alkyl, a trifluoromethyl and a methylenedioxy, said substituents being identical or different; a thienyl which is unsubstituted or substituted by a halogen atom; a benzothienyl which is unsubstituted or substituted by a halogen atom; a naphthyl which is unsubstituted or substituted by a halogen atom; an indolyl which is unsubstituted or N-substituted by a (C$_1$-C$_4$) alkyl or a benzyl; an imidazolyl which is unsubstituted or substituted by a halogen atom; a pyridyl which is unsubstituted or substituted by a halogen atom; or a biphenyl;

T is a group —CH$_2$—; a group —CO—; a group —COO—; or a group —CONR$_3$— in which R$_3$ is a hydrogen or a (C$_1$-C$_4$)alkyl;

A is a direct bond; a group —(CH$_2$)$_t$—, in which t is one, two or three; or a vinylene group;

or —T—A— is the group —SO$_2$—;

Z is an optionally substituted, mono-, di- or tri-cyclic aromatic or heteroaromatic group; and B is a group B$_1$ of the formula

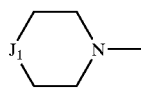

in which J$_1$ is:

i- either a group Ar$_2$—(CH$_2$)$_x$—C$\underset{X_1}{\overset{}{<}}$ in which:

x is zero or one;

AR$_2$ is a phenyl which is unsubstituted or monosubstituted or polysubstituted by a substituent selected from a halogen atom, a nitro, a hydroxyl, a trifluoromethyl, a (C$_1$-C$_4$)alkyl, a (C$_1$-C$_4$)alkoxy and a methylenedioxy, said substituents being identical or different; a pyridyl; a thienyl; a pyrimidyl; or an imidazolyl which is unsubstituted or substituted by a (C$_1$-C$_4$)alkyl; and X$_1$ is a group selected from:
(1) hydrogen;
(2) (C$_1$—C$_7$)alkyl;
(3) formyl;
(4) (C$_1$-C$_7$)alkylcarbonyl;
(5) —(CH$_2$)$_m$—R$_4$;
(6) —(CH$_2$)$_m$—OCOR$_5$;
(7) —(CH$_2$)$_m$—OCONH—(C$_1$-C$_7$)alkyl;
(8) —O—CH$_2$CH$_2$—OR$_6$;
(9) —(CH$_2$)$_n$—SR$_7$;
(10) —CH$_2$—S(O)$_j$—(C$_1$-C$_7$)alkyl;
(11) —NR$_8$R$_9$;
(12) —(CH$_2$)$_p$—NR$_{10}$R$_{11}$;
(13) —NR$_{12}$COR$_{13}$;

(14) —NR$_{14}$COCOR$_{15}$;
(15) —(CH$_2$)$_p$—NR$_{14}$C(=W$_1$)R$_{16}$;
(16) —(CH$_2$)$_m$—NR$_{14}$COOR$_{17}$;
(17) —(CH$_2$)$_m$—NR$_{14}$SO$_2$R$_{18}$;
(18) —(CH$_2$)$_m$—NR$_{14}$C(=W$_1$)NR$_{19}$R$_{20}$;
(19) —(CH$_2$)$_n$—COOR$_{21}$;
(20) —(CH$_2$)$_n$—C(=W$_1$)NR$_{19}$R$_{20}$;
(21) —CO—NR$_{22}$—NR$_{23}$R$_{24}$;
(22) —CN;

(23)
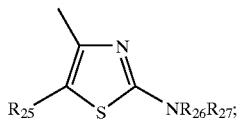

(24)
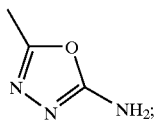

or X$_1$ forms a double bond between the carbon atom to which it is bonded and the adjacent carbon atom of the piperidine ring;

in which groups:

m is zero, one or two;

n is zero or one;

p is one or two;

j is one or two;

W$_1$ is an oxygen atom or a sulfur atom;

R$_4$ is a hydrogen or a (C$_1$–C$_7$)alkyl;

R$_5$ is a hydrogen; a (C$_1$–C$_7$)alkyl; a (C$_3$–C$_7$)cycloalkyl which is unsubstituted or substituted by one or more methyls; a phenyl; or a pyridyl;

R$_6$ is a hydrogen; a (C$_1$–C$_7$)alkyl; a formyl; or a (C$_1$–C$_7$)alkylcarbonyl;

R$_7$ is a hydrogen or a (C$_1$–C$_7$)alkyl;

R$_8$ and R$_9$ are each independently a hydrogen or a (C$_1$–C$_7$)alkyl; R$_9$ can also be a (C$_3$–C$_7$)cycloalkylmethyl, a benzyl or a phenyl;

or R$_8$ and R$_9$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a (C$_1$–C$_4$)alkyl;

R$_{10}$ and R$_{11}$ are each independently a hydrogen or a (C$_1$–C$_7$)alkyl; R$_{11}$ can also be a (C$_3$–C$_7$)cycloalkylmethyl or a benzyl;

R$_{12}$ is a hydrogen or a (C$_1$–C$_7$)alkyl;

R$_{13}$ is a hydrogen; a (C$_1$–C$_7$)alkyl; a (C$_3$–C$_7$)cycloalkyl which is unsubstituted or substituted by one or more methyls; a phenyl; a benzyl; a vinyl; a pyridyl; a furyl; a thienyl; a pyrrolyl; or an imidazolyl;

or R$_{12}$ and R$_{13}$ together are a group —(CH$_2$)$_u$—, in which u is three or four;

R$_{14}$ is a hydrogen or a (C$_1$–C$_7$)alkyl;

R$_{15}$ is a (C$_1$–C$_4$)alkoxy;

R$_{16}$ is a hydrogen; a (C$_1$–C$_7$)alkyl; a (C$_3$–C$_7$)cycloalkyl which is unsubstituted or substituted by one or more methyls; a phenyl; a benzyl; a vinyl; a pyridyl; a furyl; a thienyl; a pyrrolyl; or an imidazolyl;

R$_{17}$ is a (C$_1$–C$_7$)alkyl or a phenyl;

R$_{18}$ is a (C$_1$–C$_7$)alkyl; an amino which is free or substituted by one or two (C$_1$–C$_7$)alkyls; or a phenyl which is unsubstituted or monosubstituted or polysubstituted by a substituent selected from a halogen atom, a (C$_1$–C$_7$)alkyl, a trifluoromethyl, a hydroxyl, a (C$_1$–C$_7$)alkoxy, a carboxyl, a (C$_1$–C$_7$)alkoxycarbonyl, a (C$_1$–C$_7$)alkylcarbonyloxy, a cyano, a nitro and an amino which is free or substituted by one or two (C$_1$–C$_7$)alkyls, said substituents being identical or different;

R$_{19}$ and R$_{20}$ are each independently a hydrogen or a (C$_1$–C$_7$)alkyl; R$_{20}$ can also be a (C$_3$–C$_7$)cycloalkyl; a (C$_3$–C$_7$)cycloalkylmethyl; a hydroxyl; a (C$_1$–C$_4$)alkoxy; a benzyl; a phenyl; or a (C$_1$–C$_7$)alkyl substituted by a hydroxyl, a (C$_1$–C$_3$)alkoxy, a phenyl, a carboxyl, a (C$_1$–C$_3$)alkoxycarbonyl or a carbamoyl which is unsubstituted or substituted by one or two (C$_1$–C$_7$)alkyls;

or R$_{19}$ and R$_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a (C$_1$–C$_4$)alkyl;

R$_{21}$ is a hydrogen or a (C$_1$–C$_7$)alkyl;

R$_{22}$ is a hydrogen or a (C$_1$–C$_7$)alkyl;

R$_{23}$ and R$_{24}$ are each independently a hydrogen or a (C$_1$–C$_7$)alkyl;

R$_{25}$ is a hydrogen or a (C$_1$–C$_7$)alkyl; and

R$_{26}$ and R$_{27}$ are each independently a hydrogen or a (C$_1$–C$_7$)alkyl; R$_{27}$ can also be a formyl or a (C$_1$–C$_7$)alkylcarbonyl;

i$_2$- or a group 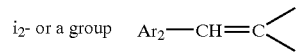

in which AR$_2$ is as defined above;

i$_3$- or a group 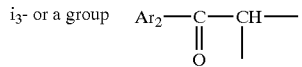

in which AR$_2$ is as defined above;

i$_4$- or a group 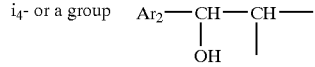

in which AR$_2$ is as defined above;

i$_5$- or a group 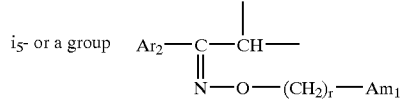

in which:

AR$_2$ is as defined above;

Am$_1$ is an amino group substituted by two (C$_1$–C$_4$)alkyls; and r is two or three;

i₆ - or a group 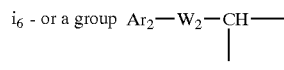

in which:

AR₂ is as defined above;

W₂ is an oxygen atom; a sulfur atom; a sulfinyl; a sulfonyl; or a group —NL₁—;

L₁ is a hydrogen; a $(C_1-C_4)$alkyl; a $(C_1-C_4)$alkylcarbonyl; or a group —$(CH_2)_v$—Am₂;

v is one, two or three; and

Am₂ is an amino group which is unsubstituted or monosubstituted or disubstituted by a $(C_1-C_4)$alkyl; Am₂ can also be a pyrrolidino, piperidino or morpholino group;

or an acid-addition salt thereof.

2. A compound according to claim 1 of the formula

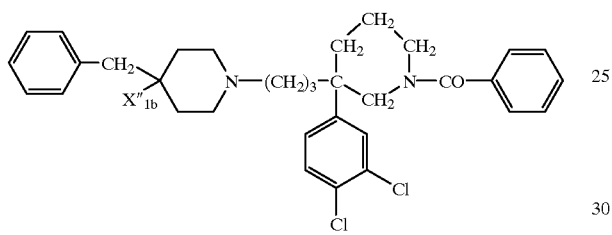

(I"b)

in which:

Ar'₁ is a phenyl which is unsubstituted or monosubstituted or polysubstituted by a substituent selected from a halogen atom, a hydroxyl, a $(C_1-C_4)$alkoxy, a $(C_1-C_4)$alkyl, a trifluoromethyl and a methylenedioxy, said substituents being identical or different;

A' is a direct bond or a group —CH₂—;

Z' is
a phenyl which is unsubstituted or monosubstituted or polysubstituted by a substituent selected from a halogen atom; a trifluoromethyl; a cyano; a hydroxyl; a nitro; an amino which is unsubstituted or monosubstituted or disubstituted by a $(C_1-C_4)$alkyl; a benzylamino; a carboxyl; a $(C_1-C_{10})$alkyl; a $(C_3-C_8)$cycloalkyl which is unsubstituted or monosubstituted or polysubstituted by a methyl; a $(C_1-C_{10})$alkoxy; a $(C_3-C_8)$cycloalkoxy which is unsubstituted or monosubstituted or polysubstituted by a methyl; a mercapto; a $(C_1-C_{10})$alkylthio; a formyloxy; a $(C_1-C_6)$alkylcarbonyloxy; a formylamino; a $(C_1-C_6)$alkylcarbonylamino; a benzoylamino; a $(C_1-C_4)$alkoxycarbonyl; a $(C_3-C_7)$cycloalkoxycarbonyl; a carbamoyl which is unsubstituted or monosubstituted or disubstituted by a $(C_1-C_4)$alkyl; a ureido which is unsubstituted or monosubstituted or disubstituted in the 3-position by a $(C_1-C_4)$alkyl or a $(C_3-C_7)$cycloalkyl; and a (pyrrolidin-1-yl)carbonylamino, said substituents being identical or different;

a naphthyl which is unsubstituted or monosubstituted or polysubstituted by a halogen, a trifluoromethyl, a $(C_1-C_4)$alkyl, a hydroxyl or a $(C_1-C_4)$alkoxy; or a pyridyl; a thienyl; an indolyl; a quinolyl; a benzothienyl; or an imidazolyl; and Bc is a group B1c of the formula

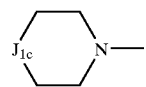

in which $J_{1c}$ is a group

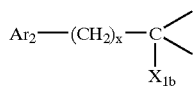

in which:

x is zero or one;

$AR_{2a}$ is a phenyl which is unsubstituted or mono substituted or polysubstituted by a substituent selected from a halogen atom, a hydroxyl, a $(C_1-C_4)$alkoxy, a $(C_1-C_4)$alkyl, a trifluoromethyl and a methylenedioxy, said substituents being identical or different; and $X_{1b}$ is a group selected from:
hydrogen;
$(C_1-C_7)$alkyl;
formyl;
$(C_1-C_7)$alkylcarbonyl;
—$(CH_2)_m$—OR₄;
—$(CH_2)_m$—OCOR₅;
$(CH_2)_m$—OCONH—$(C_1-C_7)$alkyl;
—O—CH₂CH₂—OR₆;
—$(CH_2)_n$—SR₇;
—CH₂—S(O)$_j$—$(C_1-C_7)$alkyl;
—NR₈R₉;
—$(CH_2)_p$—NR₁₀R₁₁;
—NR₁₂COR₁₃;
—NR₁₄COCOR₁₅;
—$(CH_2)_p$—NR₁₄C(=W₁)R₁₆;
—$(CH_2)_m$—NR₁₄COOR₁₇;
—$(CH_2)_m$—NR₁₄SO₂R₁₈;
—$(CH_2)_m$—NR₁₄C(=W₁)NR₁₉R₂₀;
—$(CH_2)_n$—COOR₂₁;
—$(CH_2)_n$—C(=W₁)NR₁₉R₂₀;
—CO—NR₂₂—NR₂₃R₂₄;
—CN;

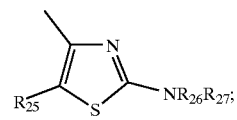

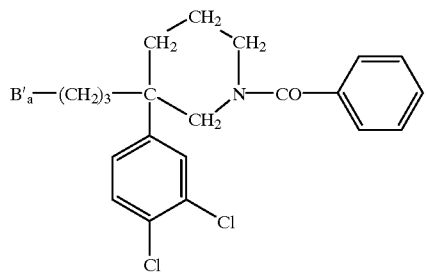

(I'a)

or $X_{1b}$ forms a double bond between the carbon atom to which it is bonded and the adjacent carbon atom of the piperidine ring, in which groups:

m is zero, one or two;

n is zero or one;

p is one or two;

j is one or two;

$W_1$ is an oxygen atom or a sulfur atom;

$R_4$ is a hydrogen or a $(C_1-C_7)$alkyl;

$R_5$ is a hydrogen; a $(C_1-C_7)$alkyl; a $(C_3-C_7)$cycloalkyl which is unsubstituted or substituted by one or more methyls; a phenyl; or a pyridyl;

$R_6$ is a hydrogen; a $(C_1-C_7)$alkyl; a formyl; or a $(C_1-C_7)$alkylcarbonyl;

$R_7$ is a hydrogen or a $(C_1-C_7)$alkyl;

$R_8$ and $R_9$ are each independently a hydrogen or a $(C_1-C_7)$alkyl; $R_9$ can also be a $(C_3-C_7)$cycloalkylmethyl, a benzyl or a phenyl;

or $R_8$ and $R_9$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$alkyl;

$R_{10}$ and $R_{11}$ are each independently a hydrogen or a $(C_1-C_7)$alkyl; $R_{11}$ can also be a $(C_3-C_7)$cycloalkylmethyl or a benzyl;

$R_{12}$ is a hydrogen or a $(C_1-C_7)$alkyl;

$R_{13}$ is a hydrogen; a $(C_1-C_7)$alkyl; a $(C_3-C_7)$cycloalkyl which is unsubstituted or substituted by one or more methyls; a phenyl; a benzyl; a vinyl; a pyridyl; a furyl; a thienyl; a pyrrolyl; or an imidazolyl;

or $R_{12}$ and $R_{13}$ together are a group —$(CH_2)_u$— in which u is three or four;

$R_{14}$ is a hydrogen or a $(C_1-C_7)$alkyl;

$R_{15}$ is a $(C_1-C_4)$alkoxy;

$R_{16}$ is a hydrogen; a $(C_1-C_7)$alkyl; a $(C_3-C_7)$cycloalkyl which is unsubstituted or substituted by one or more methyls; a phenyl; a benzyl; a vinyl; a pyridyl; a furyl; a thienyl; a pyrrolyl; or an imidazolyl;

$R_{17}$ is a $(C_1-C_7)$alkyl or a phenyl;

$R_{18}$ is a $(C_1-C_7)$alkyl; an amino which is free or substituted by one or two $(C_1-C_7)$alkyls; or a phenyl which is unsubstituted or monosubstituted or polysubstituted by a substituent selected from a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$alkylcarbonyloxy, a cyano, a nitro and an amino which is free or substituted by one or two $(C_1-C_7)$alkyls, said substituents being identical or different;

$R_{19}$ and $R_{20}$ are each independently a hydrogen or a $(C_1-C_7)$alkyl; $R_{20}$ can also be a $(C_3-C_7)$cycloalkyl; a $(C_3-C_7)$cycloalkylmethyl; a hydroxyl; a $(C_1-C_4)$alkoxy; a benzyl; a phenyl; or a $(C_1-C_7)$alkyl substituted by a hydroxyl, a $(C_1-C_3)$alkoxy, a phenyl, a carboxyl, a $(C_1-C_3)$alkoxycarbonyl or a carbamoyl which is unsubstituted or substituted by one or two $(C_1-C_7)$alkyls;

or $R_{19}$ and $R_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a $(C_1-C_4)$alkyl;

$R_{21}$ is a hydrogen or a $(C_1-C_7)$alkyl;

$R_{22}$ is a hydrogen or a $(C_1-C_7)$alkyl;

$R_{23}$ and $R_{24}$ are each independently a hydrogen or a $(C_1-C_7)$alkyl;

$R_{25}$ is a hydrogen or a $(C_1-C_7)$alkyl; and $R_{26}$ and $R_{27}$ are each independently a hydrogen or a $(C_1-C_7)$alkyl; $R_{27}$ can also be a formyl or a $(C_1-C_7)$alkylcarbonyl.

3. A compound according to claim 1 in which:

Z is Z' and is:

a phenyl which is unsubstituted or monosubstituted or polysubstituted by a substituent selected from a halogen atom; a trifluoromethyl; a cyano; a hydroxyl; a nitro; an amino which is unsubstituted or monosubstituted or disubstituted by a $(C_1-C_4)$alkyl; a benzylamino; a carboxyl; a $(C_1-C_{10})$alkyl; a $(C_3-C_8)$cycloalkyl which is unsubstituted or monosubstituted or polysubstituted by a methyl; a $(C_1-C_{10})$alkoxy; a $(C_3-C_8)$cycloalkoxy which is unsubstituted or monosubstituted or polysubstituted by a methyl; a mercapto; a $(C_1-C_{10})$alkylthio; a formyloxy; a $(C_1-C_6)$alkylcarbonyloxy; a formylamino; a $(C_1-C_6)$alkylcarbonylamino; a benzoylamino; a $(C_1-C_4)$alkoxycarbonyl; a $(C_3-C_7)$cycloalkoxycarbonyl; a carbamoyl which is unsubstituted or monosubstituted or disubstituted by a $(C_1-C_4)$alkyl; a ureido which is unsubstituted or monosubstituted or disubstituted in the 3-position by a $(C_1-C_4)$alkyl or a $(C_3-C_7)$cycloalkyl; and a (pyrrolidin-1-yl)carbonylamino, said substituents being identical or different;

a naphthyl which is unsubstituted or monosubstituted or polysubstituted by a halogen, a trifluoromethyl, a $(C_1-C_4)$alkyl, a hydroxyl or a $(C_1-C_4)$alkoxy; or a pyridyl; a thienyl; an indolyl; a quinolyl; a benzothienyl; or an imidazolyl;

$Ar_1$ is a 3,4-dichlorophenyl; and $R_1$ and $R_2$ together form a group —$(CH_2)_4$—.

4. A compound according to claim 2 of the formula

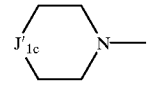

in which:

$B'_c$ is a group $B'_{1c}$ of the formula

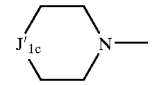

in which $J'_{1c}$ is a group

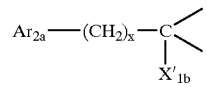

in which:

x is zero or one;

$Ar_{2a}$ is a phenyl which is unsubstituted or monosubstituted or polysubstituted by a substituent selected from a halogen atom, a hydroxyl, a $(C_1-C_4)$alkoxy, a $(C_1-C_4)$alkyl, a trifluoromethyl and a methylenedioxy, said substituents being identical or different; and $X'_{1b}$ is a group selected from:

(C$_1$–C$_7$)alkyl;

—(CH$_2$)$_m$—OR$_4$ in which m is one or two and R$_4$ is a hydrogen or a (C$_1$–C$_7$)alkyl;

—(CH$_2$)$_m$—OCOR$_5$ in which m is zero and R$_5$ is a (C$_3$–C$_7$)cycloalkyl which is unsubstituted or substituted by one or more methyls; a phenyl; or a pyridyl; and m is one or two and R$_5$ is a hydrogen; a (C$_1$–C$_7$)alkyl; a (C$_3$–C$_7$)cycloalkyl which is unsubstituted or substituted by one or more methyls; a phenyl; or a pyridyl;

—(CH$_2$)$_m$—OCONH—(C$_1$–C$_7$)alkyl in which m is zero, one or two;

—O—CH$_2$—CH$_2$—OR$_6$ in which R$_6$ is a hydrogen; a (C$_1$–C$_7$)alkyl; a formyl; or a (C$_1$–C$_7$)alkylcarbonyl;

—(CH$_2$)$_n$—SR$_7$ in which n is zero or one and R$_7$ is a hydrogen or a (C$_1$–C$_7$)alkyl;

—CH$_2$—S(O)$_j$—(C$_1$–C$_7$)alkyl in which j is one or two;

—NR$_8$R$_9$ in which R$_8$ is a hydrogen or a (C$_1$–C$_7$)alkyl and R$_9$ is a (C$_3$–C$_7$)cycloalkylmethyl or a benzyl; or R$_8$ and R$_9$, together with the nitrogen atom to which they are bonded, form a heterocycle selected from azetidine, thiomorpholine, perhydroazepine and piperazine which is unsubstituted or substituted in the 4-position by a (C$_1$–C$_4$)alkyl;

—(CH$_2$)$_p$—NR$_{10}$R$_{11}$ in which p is one or two, R$_{10}$ is a hydrogen or a (C$_1$–C$_7$)alkyl and R$_{11}$ is a hydrogen, a (C$_1$–C$_7$)alkyl, a (C$_3$–C$_7$)cycloalkylmethyl or a benzyl;

—NR$_{12}$COR$_{13}$ in which R$_{12}$ is a hydrogen or a (C$_1$–C$_7$) alkyl and R$_{13}$ is a (C$_3$–C$_7$)cycloalkyl which is unsubstituted or substituted by one or more methyls; a phenyl; a benzyl; a vinyl; a pyridyl; a furyl; a thienyl; a pyrrolyl; or an imidazolyl; or R$_{12}$ and R$_{13}$ together form a group —(CH$_2$)$_u$ in which u is three or four;

—NR$_{14}$COCOR$_{15}$ in which R$_{14}$ is a hydrogen or a (C$_1$–C$_7$)alkyl and R$_{15}$ is a (C$_1$–C$_4$)alkoxy;

—(CH$_2$)$_p$—NR$_{14}$C(=W$_1$)R$_{16}$ in which p is one or two, W$_1$ is an oxygen atom or a sulfur atom, R$_{14}$ is a hydrogen or a (C$_1$–C$_7$)alkyl and R$_{16}$ is a hydrogen or a (C$_1$–C$_7$)alkyl; a (C$_3$–C$_7$)cycloalkyl which is unsubstituted or substituted by one or more methyls; a phenyl; a benzyl; a vinyl; a pyridyl; a furyl; a thienyl; a pyrrolyl; or an imidazolyl;

—(CH$_2$)$_m$—NR$_{14}$COOR$_{17}$ in which m is zero, one or two, R$_{14}$ is a hydrogen or a (C$_1$–C$_7$)alkyl and R$_{17}$ is a (C$_1$–C$_7$)alkyl or a phenyl;

—(CH$_2$)$_m$—NR$_{14}$SO$_2$R$_{18}$ in which m is zero, one or two, R$_{14}$ is a hydrogen or a (C$_1$–C$_7$)alkyl and R$_{18}$ is a (C$_1$–C$_7$)alkyl; an amino which is free or substituted by one or two (C$_1$–C$_7$)alkyls; or a phenyl which is unsubstituted or monosubstituted or polysubstituted by a substituent selected from a halogen atom, a (C$_1$–C$_7$)alkyl, a trifluoromethyl, a hydroxyl, a (C$_1$–C$_7$)alkoxy, a carboxyl, a (C$_1$–C$_7$) alkoxycarbonyl, a (C$_1$–C$_7$)alkylcarbonyloxy, a cyano, a nitro and an amino which is free or substituted by one or two (C$_1$–C$_7$)alkyls, said substituents being identical or different;

—(CH$_2$)$_m$NR$_{14}$C(=W$_1$)NR$_{19}$R$_{20}$ in which m is zero, one or two, W$_1$ is an oxygen atom or a sulfur atom, R$_{14}$ is a hydrogen or a (C$_1$–C$_7$)alkyl and R$_{19}$ and R$_{20}$ are each independently a hydrogen or a (C$_1$–C$_7$) alkyl; R$_{20}$ can also be a (C$_3$–C$_7$)cycloalkyl; a (C$_3$–C$_7$)cycloalkylmethyl; a hydroxyl; a (C$_1$–C$_4$) alkoxy; a benzyl; a phenyl; or a (C$_1$–C$_7$)alkyl substituted by a hydroxyl, a (C$_1$–C$_3$)alkoxy, a phenyl, a carboxyl, a (C$_1$–C$_3$)alkoxycarbonyl or a carbamoyl which is unsubstituted or substituted by one or two (C$_1$–C$_7$)alkyls; or R$_{19}$ and R$_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a (C$_1$–C$_4$)alkyl;

—(CH$_2$)$_n$—COOR$_{21}$ in which n is one and R$_{21}$ is a hydrogen or a (C$_1$–C$_7$)alkyl;

—(CH$_2$)$_n$—C(=W$_1$)NR$_{19}$R$_{20}$ in which n is zero or one, W$_1$ is an oxygen atom or a sulfur atom and R$_{19}$ and R$_{20}$ are each independently a hydrogen or a (C$_1$–C$_7$)alkyl; R$_{20}$ can also be a (C$_3$–C$_7$)cycloalkyl; a (C$_3$–C$_7$)cycloalkylmethyl; a hydroxyl; a (C$_1$–C$_4$) alkoxy; a benzyl; a phenyl; or a (C$_1$–C$_7$)alkyl substituted by a hydroxyl, a (C$_1$–C$_3$)alkoxy, a phenyl, a carboxyl, a (C$_1$–C$_3$)alkoxycarbonyl or a carbamoyl which is unsubstituted or substituted by one or two (C$_1$–C$_7$)alkyls; or R$_{19}$ and R$_{20}$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a (C$_1$–C$_4$)alkyl;

—CO—NR$_{22}$—NR$_{23}$R$_{24}$ in which R$_{22}$ is a hydrogen or a (C$_1$–C$_7$)alkyl and R$_{23}$ and R$_{24}$ are each independently a hydrogen or a (C$_1$–C$_7$)alkyl;

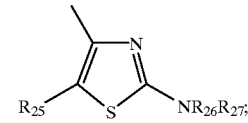

in which R$_{25}$ is a hydrogen or a (C$_1$–C$_7$)alkyl and R$_{26}$ and R$_{27}$ are each independently a hydrogen or a (C$_1$–C$_7$)alkyl; R$_{27}$ can also be a formyl or a (C$_1$–C$_7$) alkylcarbonyl; and

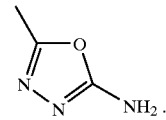

5. An enantiomer of a compound according to claim 1 of the formula

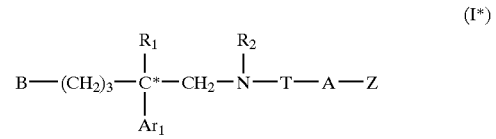

in which the carbon atom carrying the asterisk * has the determined (+) or (−) absolute configuration.

6. A pharmaceutical composition comprising a compound according to claim 1 together with a pharmaceutically acceptable excipient.

7. A pharmaceutical composition according to claim 6 containing 0.5 to 1000 mg of active principle.

8. A pharmaceutical composition according to claim 7 containing 2.5 to 250 mg of active principle.

9. A compound selected from the group consisting of:
3-[3-[4-(acetyl-N-methylamino)-4-phenylpiperid-1-yl]propyl-1-benzoyl-3-(3,4-dichlorophenyl)perhydroazepine;
1-benzoyl-3-(3,4-dichlorophenyl)-3-[3-[4-(phenyl-4-pyrrolidin-1-ylcarbonyl)-piperid-1-yl]perhydroazepine;
3-[3-[4-(2-aminothiazol-4-yl)-4-phenylpiperid-1-yl]propyl]-1-benzoyl-3-(3,4-dichlorophenyl)perhydroazepine; and
acid addition salts thereof.

10. A method for the treatment of diseases in which the $NK_3$ receptor is involved which comprises administering to a patient in need of such treatment a therapeutically effective amount of a compound according to claim 1.

11. A pharmaceutical composition comprising a compound according to claim 9 together with a pharmaceutically acceptable excipient.

12. A method for the treatment of diseases in which the $NK_3$ receptor is involved which comprises administering to a patient in need of such treatment a therapeutically effective amount of a compound according to claim 9.

* * * * *